United States Patent
Kosmeder et al.

(10) Patent No.: US 8,445,191 B2
(45) Date of Patent: May 21, 2013

(54) POLYMERIC CARRIERS FOR IMMUNOHISTOCHEMISTRY AND IN SITU HYBRIDIZATION

(75) Inventors: Jerome W. Kosmeder, Tucson, AZ (US); Casey A. Kernag, Tucson, AZ (US); Donald Johnson, Tucson, AZ (US); Christopher Bieniarz, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 13/068,144

(22) Filed: May 2, 2011

(65) Prior Publication Data

US 2011/0244544 A1    Oct. 6, 2011

Related U.S. Application Data

(62) Division of application No. 12/154,472, filed on May 22, 2008, now Pat. No. 7,985,557.

(60) Provisional application No. 60/931,546, filed on May 23, 2007.

(51) Int. Cl.
   *C12Q 1/70* (2006.01)
   *C12Q 1/68* (2006.01)
   *C07H 19/04* (2006.01)
   *C07K 1/00* (2006.01)
   *C07K 16/00* (2006.01)

(52) U.S. Cl.
   USPC ............... 435/5; 435/6.1; 435/7.1; 435/7.2; 536/26.6; 530/300; 530/350; 530/387.1

(58) Field of Classification Search
   USPC ......... 425/5, 6.1, 7.1, 7.2; 536/26.6; 530/300, 530/350, 387.1
   See application file for complete search history.

(56) References Cited

U.S. PATENT DOCUMENTS

| 3,892,530 A | 7/1975 | Felix et al. |
| 4,230,683 A | 10/1980 | Decker et al. |
| 4,425,427 A | 1/1984 | Luderer |
| 4,469,797 A | 9/1984 | Albarella |

(Continued)

FOREIGN PATENT DOCUMENTS

| JP | H09-500411 | 1/1997 |
| WO | WO 95/02700 | 1/1995 |

(Continued)

OTHER PUBLICATIONS

Maassen et al. (Eur. J. Biochem. 1983, 134, 327-330).*

(Continued)

*Primary Examiner* — Jezia Riley
(74) *Attorney, Agent, or Firm* — Klarquist Sparkman, LLP

(57) ABSTRACT

Certain disclosed embodiments of the present invention concern the synthesis, derivatization, conjugation to immunoglobulins and signal amplification based on discrete, relatively short polymers having plural reactive functional groups that react with plural molecules of interest. Reactive functional groups, such as hydrazides, may be derivatized with a variety of detectable labels, particularly haptens. The remaining reactive functional groups may be conjugated directly to a specific binding molecule, such as to the oxidized carbohydrate of the Fc region of the antibody. Disclosed conjugates display large signal amplification as compared to those based on molecules derivatized with single haptens, and are useful for assay methods, particularly multiplexed assays.

37 Claims, 18 Drawing Sheets

U.S. PATENT DOCUMENTS

| | | |
|---|---|---|
| 4,490,473 A | 12/1984 | Brunhouse et al. |
| 4,495,296 A | 1/1985 | Neurath et al. |
| 4,879,224 A | 11/1989 | Wallner et al. |
| 5,198,537 A | 3/1993 | Huber et al. |
| 5,225,325 A | 7/1993 | Miller et al. |
| 5,322,771 A | 6/1994 | Rybski et al. |
| 5,350,686 A | 9/1994 | Jhingan |
| 5,403,747 A | 4/1995 | Akins et al. |
| 5,418,138 A | 5/1995 | Miller et al. |
| 5,447,841 A | 9/1995 | Gray et al. |
| 5,487,975 A | 1/1996 | Miller et al. |
| 5,585,089 A | 12/1996 | Queen et al. |
| 5,643,761 A | 7/1997 | Fisher et al. |
| 5,648,211 A | 7/1997 | Fraiser et al. |
| 5,648,245 A | 7/1997 | Fire et al. |
| 5,650,327 A | 7/1997 | Copeland et al. |
| 5,654,200 A | 8/1997 | Copeland et al. |
| 5,661,040 A | 8/1997 | Huff et al. |
| 5,679,582 A | 10/1997 | Bowie et al. |
| 5,684,142 A | 11/1997 | Mishra et al. |
| 5,731,171 A | 3/1998 | Bohlander |
| 5,756,696 A | 5/1998 | Gray et al. |
| 5,759,808 A | 6/1998 | Casterman et al. |
| 5,800,988 A | 9/1998 | Casterman et al. |
| 5,840,526 A | 11/1998 | Casterman et al. |
| 5,874,541 A | 2/1999 | Casterman et al. |
| 5,883,081 A | 3/1999 | Kraus et al. |
| 5,994,071 A | 11/1999 | Ross et al. |
| 6,005,079 A | 12/1999 | Casterman et al. |
| 6,015,695 A | 1/2000 | Casterman et al. |
| 6,057,099 A | 5/2000 | Nathan et al. |
| 6,124,120 A | 9/2000 | Lizardi |
| 6,180,349 B1 | 1/2001 | Ginzinger et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,152 B1 | 4/2001 | Auerbach |
| 6,218,371 B1 | 4/2001 | Krieg et al. |
| 6,235,480 B1 | 5/2001 | Shultz et al. |
| 6,239,116 B1 | 5/2001 | Krieg et al. |
| 6,280,929 B1 | 8/2001 | Gray et al. |
| 6,280,949 B1 | 8/2001 | Lizardi |
| 6,291,187 B1 | 9/2001 | Kingsmore et al. |
| 6,296,809 B1 | 10/2001 | Richards et al. |
| 6,322,901 B1 | 11/2001 | Bawendi et al. |
| 6,323,009 B1 | 11/2001 | Lasken et al. |
| 6,339,068 B1 | 1/2002 | Krieg et al. |
| 6,344,337 B1 | 2/2002 | Mansfield et al. |
| 6,352,861 B1 | 3/2002 | Copeland et al. |
| 6,358,682 B1 | 3/2002 | Jaffee et al. |
| 6,406,705 B1 | 6/2002 | Davis et al. |
| 6,414,133 B1 | 7/2002 | Dietz-Band et al. |
| 6,429,199 B1 | 8/2002 | Krieg et al. |
| 6,432,320 B1 | 8/2002 | Bonsignore et al. |
| 6,447,692 B1 | 9/2002 | Momoda et al. |
| 6,495,324 B1 | 12/2002 | Mirkin et al. |
| 6,506,564 B1 | 1/2003 | Mirkin et al. |
| 6,544,798 B1 | 4/2003 | Christensen et al. |
| 6,569,621 B1 | 5/2003 | Cremer et al. |
| 6,576,291 B2 | 6/2003 | Bawendi et al. |
| 6,582,921 B2 | 6/2003 | Mirkin et al. |
| 6,592,844 B2 | 7/2003 | Coombes et al. |
| 6,607,877 B1 | 8/2003 | Gray et al. |
| 6,617,137 B2 | 9/2003 | Dean et al. |
| 6,632,609 B2 | 10/2003 | Lizardi |
| 6,638,722 B2 | 10/2003 | Ji et al. |
| 6,642,034 B2 | 11/2003 | Lizardi |
| 6,649,138 B2 | 11/2003 | Adams et al. |
| 6,656,685 B2 | 12/2003 | Utermohlen et al. |
| 6,670,113 B2 | 12/2003 | Hainfeld |
| 6,673,214 B1 | 1/2004 | Marchitto et al. |
| 6,682,596 B2 | 1/2004 | Zehnder et al. |
| 6,695,974 B2 | 2/2004 | Withers et al. |
| 6,696,304 B1 | 2/2004 | Davies |
| 6,699,973 B1 | 3/2004 | O'Mahony et al. |
| 6,750,016 B2 | 6/2004 | Mirkin et al. |
| 6,767,702 B2 | 7/2004 | Mirkin et al. |
| 6,797,474 B2 | 9/2004 | Lizardi |
| 6,815,064 B2 | 11/2004 | Treadway et al. |
| 6,827,901 B2 | 12/2004 | Copeland et al. |
| 6,828,097 B1 | 12/2004 | Knoll et al. |
| 6,855,552 B2 | 2/2005 | Towne et al. |
| 6,921,496 B2 | 7/2005 | Anderson et al. |
| 6,933,117 B2 | 8/2005 | Wolf et al. |
| 6,942,970 B2 | 9/2005 | Isola et al. |
| 6,943,029 B2 | 9/2005 | Copeland et al. |
| 6,944,333 B2 | 9/2005 | Douglass |
| 6,962,789 B2 | 11/2005 | Bacus |
| 6,977,148 B2 | 12/2005 | Dean et al. |
| 7,014,997 B2 | 3/2006 | Knoll et al. |
| 7,045,504 B2 | 5/2006 | Wilhelm et al. |
| 7,056,471 B1 | 6/2006 | Han et al. |
| 7,067,325 B2 | 6/2006 | Christensen et al. |
| 7,087,379 B2 | 8/2006 | Light |
| 7,104,313 B2 | 9/2006 | Pokharna et al. |
| 7,200,252 B2 | 4/2007 | Douglass |
| 7,250,254 B2 | 7/2007 | Dietz-Band et al. |
| 7,285,289 B2 | 10/2007 | Nagy et al. |
| 7,292,718 B2 | 11/2007 | Douglass |
| 7,300,748 B2 | 11/2007 | Fischer et al. |
| 7,358,041 B2 | 4/2008 | Short et al. |
| 7,541,455 B2 | 6/2009 | Bieniarz et al. |
| 7,682,789 B2 | 3/2010 | Chen et al. |
| 7,695,929 B2 | 4/2010 | Kosmeder et al. |
| 2001/0051342 A1 | 12/2001 | Farrell |
| 2002/0019001 A1 | 2/2002 | Light |
| 2002/0117659 A1 | 8/2002 | Lieber et al. |
| 2003/0003537 A1 | 1/2003 | Fischer et al. |
| 2003/0008414 A1 | 1/2003 | Nie et al. |
| 2003/0022166 A1 | 1/2003 | Collins et al. |
| 2003/0022243 A1 | 1/2003 | Kondejewski et al. |
| 2003/0059790 A1 | 3/2003 | Jaffee et al. |
| 2003/0066998 A1 | 4/2003 | Lee |
| 2003/0122630 A1 | 7/2003 | Fallisgaard et al. |
| 2003/0165485 A1 | 9/2003 | Bertilsson et al. |
| 2004/0052685 A1 | 3/2004 | Richards |
| 2004/0057958 A1 | 3/2004 | Waggoner et al. |
| 2004/0067511 A1 | 4/2004 | Thomas |
| 2004/0077844 A1 | 4/2004 | Jacobson et al. |
| 2004/0101822 A1 | 5/2004 | Wiesner et al. |
| 2004/0115727 A1 | 6/2004 | Steward et al. |
| 2004/0161742 A1 | 8/2004 | Dean et al. |
| 2004/0209303 A1 | 10/2004 | Martin et al. |
| 2004/0214245 A1 | 10/2004 | Schmitt et al. |
| 2004/0229300 A1 | 11/2004 | Frederickson |
| 2004/0248151 A1 | 12/2004 | Bacus et al. |
| 2004/0253603 A1 | 12/2004 | Utermohlen et al. |
| 2004/0265897 A1 | 12/2004 | Lizardi |
| 2004/0265922 A1 | 12/2004 | Bieniarz et al. |
| 2005/0012182 A1 | 1/2005 | Jang et al. |
| 2005/0014133 A1 | 1/2005 | Light et al. |
| 2005/0019901 A1 | 1/2005 | Matveeva et al. |
| 2005/0048498 A1 | 3/2005 | Woudenberg et al. |
| 2005/0054578 A1 | 3/2005 | Sandberg et al. |
| 2005/0064488 A1 | 3/2005 | Huh et al. |
| 2005/0074890 A1 | 4/2005 | Lemme et al. |
| 2005/0100976 A1 | 5/2005 | Bieniarz et al. |
| 2005/0106639 A1 | 5/2005 | Bacus et al. |
| 2005/0112636 A1 | 5/2005 | Hurt et al. |
| 2005/0118725 A1 | 6/2005 | Towne et al. |
| 2005/0158770 A1 | 7/2005 | Bieniarz et al. |
| 2005/0159432 A1 | 7/2005 | Shepard et al. |
| 2005/0164213 A1 | 7/2005 | Tabor et al. |
| 2005/0181394 A1 | 8/2005 | Steemers et al. |
| 2005/0272032 A1 | 12/2005 | Ji |
| 2006/0110744 A1 | 5/2006 | Sampas et al. |
| 2006/0148124 A1 | 7/2006 | Wilson |
| 2006/0160116 A1 | 7/2006 | Christian et al. |
| 2006/0192283 A1 | 8/2006 | Benson et al. |
| 2006/0246524 A1 | 11/2006 | Bauer et al. |
| 2006/0275784 A1 | 12/2006 | Light et al. |
| 2007/0057263 A1 | 3/2007 | Kahen |
| 2007/0099283 A1 | 5/2007 | Mueller et al. |
| 2007/0117153 A1 | 5/2007 | Bieniarz |
| 2007/0274996 A1 | 11/2007 | Carter et al. |
| 2008/0057513 A1 | 3/2008 | Farrell |
| 2008/0119399 A1 | 5/2008 | Itoh et al. |

| | | | |
|---|---|---|---|
| 2008/0268462 | A1 | 10/2008 | Kosmeder |
| 2009/0017050 | A1 | 1/2009 | Powell et al. |
| 2010/0151489 | A1 | 6/2010 | Chen et al. |

FOREIGN PATENT DOCUMENTS

| | | |
|---|---|---|
| WO | WO 01/88089 | 11/2001 |
| WO | WO 2004/040314 | 5/2004 |
| WO | WO 2004/072231 | 8/2004 |
| WO | WO 2005/001889 | 1/2005 |
| WO | WO 2005/003777 | 1/2005 |
| WO | WO 2006/116742 | 11/2006 |
| WO | WO 2007/079128 | 7/2007 |
| WO | WO 2008/028156 | 3/2008 |

OTHER PUBLICATIONS

Bieniarz et al (Bioconjugate Chem. 1996, 7, 88-95).*
Nisnevitch et al (J. Biochem. Biophys. Methods (2001), 467-480).*
Abd-Elsalam, "Bioinformatic Tools and Guideline for PCR Primer Design," *Afr. J. Biotechnol.* 2:91-95, 2003.
Alonso, et al., "Real-time PCR designs to estimate nulear and mitochondrial DNA copy number in forensic and ancient DNA studies", *Forensic Science International* 139:141-149, 2004.
Andreasson, et al., "Real-time DNA quantification of nuclear and mitochondrial DNA in forensic analysis", *Biotechniques* 33(2):402-411, 2002.
Baglin et al., "A Review of Natural and Modified Betulinic, Ursolic and Echinocystic Acid Derivatives as Potential Antineoplastic Agents," *Mini Review in Medicinal Chemistry* 3:525-539, 2003.
Baltina, "Chemical Modification of Glycyrrhizic Acid as a Route to New Bioactive Compounds for Medicine," *Current Medicinal Chemistry* 10:155-171, 2003.
Bedell et al., "MaskerAid: A Performance Enhancement to RepeatMasker," *Bioformatics* 16:1040-1041, 2000.
Bischoff, et al., "Estimates of aneuploidy using multicolor fluorescence in situ hybridization on human sperm", *Cytogenetics and Cell Genetics* 66:237-243, 1994.
Bocker et al., "Common adult stem cells in the human breast give rise to glandular and myoepithelial cell lineages: A new cell biological concept," *Laboratory Investigation* 82(6):737-745, 2002.
Boeker et al., "Usual ductal hyperplasia of the breast is a committed stem (progenitor) cell lesion distinct from atypical ductal hyperplasia and ductal carcinoma in situ," *Journal of Pathology* 198(4):458-567, 2002.
Borghouts et al., "Peptide Aptamer Libraries," *Combinatorial Chemistry & High Throughput Screening* 11:135-145, 2008.
Bourne, "Handbook of Immunoperoxidase Staining Methods," DAKO Corporation, Santa Barbara, California, 1983.
Buchwalow et al., "A multicolor fluorescence immunostaining technique for simultaneous antigen targeting," *Acta Histochemica* 107(2):143-148, 2005.
Buerger and Groner, "Bifunctional Recombinant Proteins in Cancer Therapy: Cell Penetrating Peptide Aptamers as Inhibitors of Growth Factor Signaling," *J Cancer Res. Clin. Oncol.* 129:669-675, 2003.
Bullock et al., "Structure of the SOCS4-ElonginB/C Complex Reveals a Distinct SOCS Box Interface and the Molecular Basis for SOCS-Dependent EGFR Degradation," *Structure* 15:1493-1504, 2007.
Cao et al., "Adenovirus-Mediated Ribonucleotide Reductase R1 Gene Therapy of Human Colon Adenocarcinoma," *Clin. Cancer Res.* 9:4553-4561, 2003.
Chan et al., "A Human Transferrin-Vascular Endothelial Growth Factor (hnTf-VEGF) Fusion Protein Containing an Integrated Binding Site for (111)In for Imaging Tumor Angiogenesis," *J. Nucl. Med.* 46:1745-1752, 2005.
Chin et al., "Activation of the STAT Signaling Pathway Can Cause Expression of Caspase 1 and Apoptosis," *Mol. Cell. Biol.* 17:5328-5337, 1997.
Connolly and Hill, "Triterpenoids," *Nat. Prod. Rep.* 19:494-513, 2002.
Crombie and Whiting, "Biosynthesis in Rotenoids Group of Natural Products: Application of Isotope Methodology," *Phytochemistry* 49:1479-1507, 1998.
Das et al., "Pool boiling characteristics of nano-fluids," *International Journal of Heat and Mass Transfer* 46:851-862, 2003.
Davison et al., "Subtracted, Unique-Sequence, In Situ Hybridization Experimental and Diagnostic Applications," *Am. J. Pathol.* 153:1401-1409, 1998.
Desbene and Giorgi-Renault, "Drugs that Inhibit Tubulin Polymerization: The Particular Case of Podophyllotoxin and Analogues," *Curr. Med. Chem.—Anti-Cancer Agents* 2:71-90, 2002.
Devi et al., "Antibodies to poly[($2\rightarrow 48$)-$\alpha$-N-Acetylneuraminic acid] and poly[($2\rightarrow 9$)-$\alpha$-N-Acetylneuraminic acid] are Elicited by Immunization of Mice with *Escherichia coli* K92 Conjugates: Potential Vaccines for Groups B and C *Meningococci* and *E. coli* K1," *PNAS* 88:7175-7179, 1991.
Dhami et al., "Exon Array CGH: Detection of Copy-Number Changes at the Resolution of Individual Exons in the Human Genome," *Am. J. Hum. Genet.* 76:750-762, 2005.
Dintzis et al., "Molecular Determinants of Immunogenicity: The Immunon Model of Immune Response," *PNAS* 73(10):3671-3675, 1976.
Dubertret et al., "In vivo imaging of quantum dots encapsulated in phospholipid micelles," *Science* 298:1759-1762, 2002.
Fang and Casida, "Cube Resin Insecticide: Identification and Biological Activity of 29 Rotenoid Constituents," *J. Agric. Food Chem.*, 47:2130-2136, 1999.
Fattom et al., "Serum antibody response in adult volunteers elicited by injection of *Streptococcus pneumoniae* type 12F polysaccharide alone or conjugated to diphtheria toxoid," *Infect. Immun.* 58:2309-2312, 1990.
"Fluorescent Labels for Antibodies and Molecular Probes," hmds. org.uk/fluorochrome.html, HMDS, 8 pages, Nov. 11, 2003.
Gilham, "An addition reaction specific for uridine and guanosine nucleotides and its application to the modification of ribonuclease action," *J. Am. Chem. Soc.* 84:687-688, 1962.
Gonzalez et al., "Multiple Displacement Amplification as a Pre-Polymerase Chain Reaction (pre-PCR) to Process Difficult to Amplify Samples and Low Copy Number Sequences from Natural Environments," *Environ. Microbiol.* 7:1024-1028.
Gordaliza et al., "Podophyllotoxin: Distribution, Sources, Applications and New Cytotoxic Derivatives," *Toxicon* 44:441-459, 2004.
Gzyl et al., "Amplified Fragment Length Polymorphism (AFLP) Versus Randomly Amplified Polymorphic DNA (RAPD) as New Tools for Inter- and Intra-species Differentiation within *Bordetella*," *J. Med. Microbiol.* 54:333-346, 2005.
Haigler and Carpenter, "Production and Characterization of Antibody Blocking Epidermal Growth Factor: Receptor Interactions," *Biochim. Biophys. Acta* 598:314-325, 1980.
Hartig et al., "Simultaneous detection of tau phosphor-epitopes with haptenylated antibodies," *Neuroreport* 17(9):870, 2006.
He, et al., "Detection and quantification of mitochondrial DNA deletions in individual cells by real-time PCR", *Nucleic Acids Research* 30(14):e68, 2002.
Hotta et al., "Molecular Cloning and Characterization of an Antigen Associated with Early Stages of Melanoma Tumor Progression," *Cancer Res.* 48:2955-2962, 1988.
Hyland et al., "Generation and Functional Characterization of Intracellular Antibodies Interacting with the Kinase Domain of Human EGF Receptor," *Oncogene* 22:1557-1567, 2003.
Inoue et al., "Improvements of Rolling Circle Amplification (RCA) Efficiency and Accuracy Using *Thermus thermophilus* SSB Mutant Protein," *Nucleic Acids Res.* 34:e69, 2006.
Iwamoto et al., "Identification of a Membrane-Associated Inhibitor(s) of Epidermal Growth Factor-Induced Signal Transducer and Activator of Transcription Activation," *J. Biol. Chem.* 273:18198-18204, 1998.
Jack and Hardman, "Sequence Organization in Nuclear Deoxyribonucleic Acid from *Physarum polycephalum*," *Biochem. J.* 187:105-113, 1980.
Jaiswal et al., "Long-term multiple color imaging of live cells using quantum dot bioconjugates," *Nature Biotechnol.* 21:47-51, 2003.
Kario et aL, "Suppressors of Cytokine Signaling 4 and 5 Regulate Epidermal Growth Factor Receptor Signaling," *J. Biol. Chem.* 280:7038-7048, 2005.

Korn, "A Comprehensive Sequence Analysis Program for the IBM Personal Computer," *Nucleic Acids Res.* 12:581-599, 1984.

Kunz et al., "Peptide Aptamers with Binding Specificity for the Intracellular Domain of the ErbB2 Receptor Interfere with AKT Signaling and Sensitize Breast Cancer Cells to Taxol," *Mol. Cancer Res.* 4:983-998, 2006.

Le Tourneau et al., "Progress and Challenges in the Identification of Biomarkers for EGFR and VEGFR Targeting Anticancer Agents," *Drug Resistance Updates* 11:99-109, 2008.

Lee et al., "Suppression of Reaginic Antibody Formation: III. Relationship Between Immunogenicity and Tolerogenicity of Hapten-Carrier Conjugates," *J. Immunol.*, 116:1711-1718, 1976.

Lefebvre et aL, "FORRepeats: Detects Repeats on Entire Chromosomes and Between Genomes," *Bioinformatics* 19:319-326, 2003.

Levy and Mattei, Chapter 9 "Applications of Chromosomal in situ Hybridization," in *Gene probes 2: A Practical Approach*, Hames and Higgins (eds.), pp. 211-243, Oxford University Press, 1995.

Lewis et al., "New Approaches to the Analysis of Palindromic Sequences from the Human Genome: Evolution and Polymorphism of an Intronic Site at the NF1 Locus," *Nucleic Acids Res.* 33:e186, 2005.

Lichter et al., "Rapid Detection of Human Chromosome 21 Aberrations by In Situ Hybridization," *Proc. Natl. Acad. Sci. USA* 85:9664-9668, 1988.

Liu et al., "Development and Validation of a T7 Based Linear Amplification for Genomic DNA," *BMC Genomics* 4:19, 2003.

Mantripragada et al., "Genomic Microarrays in the Spotlight," *Trends Genet.* 20:87-94, 2004.

Mantripragada, "Microarray-Based Comparative Genomic Hybridization in Neurofibromatoses and DiGeorge Syndrome," *Digital Comprehensive Summaries of Uppsala Dissertations from the Faculty of Medicine* 26, 70 pp., Acta Universitatis Upsaliensis, Uppsala, Sweden, 2005.

Masuda et al., "New biotinylating reagent utilizing carbodiimide function," *Nucleic Acids Symp. Ser.* 34:69-70, 1995.

Meresse et al., "Etoposide: Discovery and Medicinal Chemistry," *Current Medicinal Chemistry* 11:2443-2466, 2004.

Metz and Brown, "The investigation of nucleic acid secondary structure by means of chemical modification with a carbodiimide reagent. I. The reaction between N-cyclohexyl-N'-β-(4-methylmorphilinium)ethylcarbodiimide and model nucleosides," *Biochem.* 8(6):2312-2328, 1969.

Miller, et al., "Precise determination of mitochondrial DNA copy number in human skeletal and cardiac muscle by a PCR-based assay: lack of change of copy number with age", *Nucleic Acids Research* 31(11):e61, 2003.

Mühlmann, "Molecular Cytogenetics in Metaphase and Interphase Cells for Cancer and Genetic Research, Diagnosis and Prognosis. Application in Tissue Sections and Cell Suspensions," *Genet. Mol. Res.* 1:117-127, 2002.

Mukumoto et al., "Investigation of ferrocenyl carbodiimide (FCDI) in the modification reaction of nucleic acids," *Nucleic Acids Symp. Ser. (Oxf.)* 49:231-232, 2005.

Musco et al., "Comparison of Flow Cytometry and Laser Scanning Cytometry for the Intracellular Evaluation of Adenoviral Infectivity and p53 Protein Expression in Gene Therapy," *Cytometry* 33:290-296, 1998.

Nagesha et al., "Application of Linker-Ligation-PCR for Construction of Phage Display Epitope Libraries," *J. Virol. Methods* 60:147-154, 1996.

Nicholson et al., "Suppressor of Cytokine Signaling (SOCS)-5 is a Potential Negative Regulator of Epidermal Growth Factor Signaling," *Proc. Natl. Acad. Sci. USA* 102:2328-2333, 2005.

"Note 7.1—Product Highlight: Guide to Labeling Antibodies with Alexa Fluor Dyes,"*probes.invitrogen.com/handbook/boxes/2020.html*, Invitrogen, pp. 6-9, Apr. 2, 2006.

Notomi et al., "Loop-Mediated Isothermal Amplification of DNA," *Nucleic Acids Res.* 28:e63, 2000.

Panelli et al., "Ligation Overcomes Terminal Underrepresentation in Multiple Displacement Amplification of Linear DNA," *BioTechniques* 39:174-180, 2005.

Paul and Apgar, "Single-Molecule Dilution and Multiple Displacement Amplification for Molecular Haplotyping," *BioTechniques* 38:553-559, 2005.

Pavliakova et al., "Treatment with Succinic Anhydride Improves the Immunogenicity of *Shigella flexneri* Type 2a O-Specific Polysaccharide-Protein Conjugates in Mice," *Infect. Immun.* 68:2161-2166, 2000.

Peng et al., "Multiple PCR Analyses on Trace Amounts of DNA Extracted from Fresh and Paraffin Wax Embedded Tissues after Random Hexamer Primer PCR Amplification," *J. Clin. Pathol.* 47:605-608, 1994.

Pinkel et al., "Cytogenetic Analysis Using Quantitative, High-Sensitivity, Fluorescence Hybridization," *Proc. Natl. Acad. Sci. USA* 83:2934-2938, 1986.

Pinkel et al., "Fluorescence In Situ Hybridization with Human Chromosome-Specific Libraries: Detection of Trisomy 21 and Translocations of Chromosome 4," *Proc. Natl. Sci. USA* 85:9138-9142, 1988.

Pitt et al., "Haptenylation of antibodies during affinity purification: A novel and convenient procedure to obtain labeled antibodies for quantification and double labeling," *Histochemistry and Cell Biology* 110(3):312-313, 1998.

Poddighe et al., "Human Papilloma Virus Detection by In Situ Hybridisation Signal Amplification Based on Biotinylated Tyramine Deposition," *J. Clin. Pathol.: Mol. Pathol.* 49:M340-M344, 1996.

Pollack et al., "Enzyme immobilization by condensation copolymerization into crosslinked polyacrylamide gels," *JACS* 2:6324-6336, 1980.

Porter and Vaillancourt, "Tyrosine Kinase Receptor-Activated Signal Transduction Pathways Which Lead to Oncogenesis, " *Oncogene* 16:1343-1352, 1998.

Potgieter et al., "Cloning of Complete Genome Sets of Six dsRNA Viruses Using an Improved Cloning Method for Large dsRNA Genes," *J. Gen. Virol.* 83:2215-2223, 2002.

Pozsgay et al., "Protein conjugates of synthetic saccharides elicit higher levels of serum IgG lipopolysaccharide antibodies in mice than do those of the O-specific polysaccharide from *Shigella dysenteriae* type 1," *PNAS* 96:5194-97, 1999.

Pujol et al., "Synthesis of Biological Activity of New Class of Dioxygenated Anticancer Agents," *Curr. Med. Chem.—Anti-Cancer Agents* 5:215-237, 2005.

Radelof et al., "Preselection of Shotgun Clones by Oligonucleotide Fingerprinting: An Efficient and High Throughput Strategy to Reduce Redundancy in Large-Scale Sequencing Projects," *Nucleic Acids Res.* 26:5358-5364, 1998.

Ried, et al., "Evaluation of the utility of interphase cytogenetics to detect residual cells with a malignant genotype in mixed cell populations: A Burkitt lymphoma model", *DNA and Cell Biology* 12(7):637-643, 1993.

Rigby et al., "Labeling deoxyribonucleic acid to high specific activity in vitro by nick translation with DNA polymerase I," *J. Mol. Biol.* 113:237-251, 1977.

Roylance, "Methods of Molecular Analysis: Accessing Losses and Gains in Tumours," *J. Clin. Pathol.: Mol. Pathol.* 55:25-28, 2002.

Schiller, et al., "High-risk human papillomavirus detection: A split-sample comparison of hybrid capture and chromogenic in situ hybridization", *American Journal of Clinical Pathology* 121:537-545, 2004.

Schreiber et al., "Monoclonal Antibodies Against Receptor for Epidermal Growth Factor Induce Early and Delayed Effects of Epidermal Growth Factor," *Proc. Natl. Acad. Sci. USA* 78:7535-7539, 1981.

Setzer and Setzer, "Plant-Derived Triterpenoids as Potential Antineoplastic Agents," *Mini Reviews in Medicinal Chemistry* 3:540-556, 2003.

Simonian, "Spectrophotometric Determination of Protein Concentration," *Current Protocols in Food Analytical Chemistry* B1.3.1-B.13.7, 2002.

Singh et al., "Advances in Vaccine Adjuvants," *Nat. Biotechnol.* 17:1075-1081, 1999.

Song and Shuai, "The Suppressor of Cytokine Signaling (SOCS) 1 and SOCS3 but Not SOCS2 Proteins Inhibit Interferon-Mediated Antiviral and Antiproliferative Activities," *J. Biol. Chem.* 273:35056-35062, 1998.

Strauss et al., "Ligation-Mediated Suppression-PCR as a Powerful Tool to Analyse Nuclear Gene Sequences in the Green Alga *Chlamydomonas reinhardtii*," *Photosynth. Res.* 70:311-320, 2001.

Szu et al., "Relation between Structure and Immunologic Properties of the Vi Capsular Polysaccharide," *Infect. Immun.* 59:4555-4561, 1991.

Szu et al., "Vi Capsular Polysaccharide-Protein Conjugates for Prevention of Typhoid Fever," *J. Exp. Med.* 166:1510-1524, 1987.

Takahara et al., "A New Retrovirus Packaging Cell for Gene Transfer Constructed from Amplified Long Terminal Repeat-Free Chimeric Proviral Genes," *J. Virol.* 66:3725-3732, 1992.

Tanner et al., "Chromogenic In Situ Hybridization: A Practical Alternative for Fluorescence In Situ Hybridization to Detect HER-2/neu Oncogene Amplification in Archival Breast Cancer Samples," *Am. J. Pathol.* 157:1467-1472, 2000.

van de Lagemaat et al., "Genomic Deletions and Precise Removal of Transposable Elements Mediated by Short Identical DNA Segments in Primates," *Genome Res.* 15:1243-1249, 2005.

Vieux et al., "Primer Design for PCR and Sequencing in High-Throughput Analysis of SNPs," *Biotechniques* 32:S28-S32, 2002.

Walker et al., "Strand Displacement Amplification—An Isothermal, In Vitro DNA Amplification Technique," *Nucleic Acids Res.* 20:1691-1696, 1992.

Walker et al., Isothermal in Vitro Amplification of DNA by a Restriction Enzyme/DNA Polymerase System, *Proc. Natl. Sci. USA* 89:392-396, 1992.

Wang et al., "DNA Amplification Method Tolerant to Sample Degradation," *Genome Res.* 14:2357-2366, 2004.

Waterfield et al., "A Monoclonal Antibody to the Human Epidermal Growth Factor Receptor," *J. Cell Biochem.* 20:149-161, 1982.

White et al., "Concatemer Chain Reaction: A Taq DNA-Polymerase-Mediated Mechanism for Generating Long Tandemly Repetitive DNA Sequences," *Anal. Biochem.* 199:184-190, 1991.

Wu et aL, "Immunofluorescent labeling of cancer marker Her2 and other cellular targets with semiconductor quantum dots," *Nature Biotech.* 21:41-46, 2003.

Xia et al., "Identification of Both Positive and Negative Domains within the Epidermal Growth Factor Receptor COOH-Terminal Region for Signal Transducer and Activator of Transcription (STAT) Activation," *J. Biol. Chem.* 277:30716-30723, 2002.

You, "Podophyllotoxin Derivatives: Current Synthetic Approaches for New Anticancer Agents," *Current Pharmaceutical Design* 11:1695-1717, 2005.

Zhang et al., "Amplification of Target-Specific, Ligation-Dependent Circular Probe," *Gene* 211:277-285, 1998.

Zhang, "DNA Amplification: Current Technologies and Applications," *Expert Rev. Mol. Diagn.* 5:127-129, 2005.

Zhong et al., "Simultaneous Detection of Microsatellite Repeats and SNPs in the Macrophage Migration Inhibitory Factor (MIF) Gene by Thin-Film Biosensor Chips and Application to Rural Field Studies," *Nucleic Acids Res.* 33:e121, 2005.

International Search Report dated Jun. 3, 2009, from International Application No. PCT/US2008/006591.

Office action dated Sep. 17, 2008, from U.S. Appl. No. 11/800,360.

Office action dated Apr. 2, 2009, from U.S. Appl. No. 11/800,360.

Office action dated Dec. 19, 2008, from U.S. Appl. No. 11/982,627.

Office action dated Jul. 24, 2009, from U.S. Appl. No. 11/982,627.

Office action dated Aug. 17, 2010, from U.S. Appl. No. 12/658,092.

Bang et al., "Boiling heat transfer performance and phenomena of $Al_2O_3$-water nano-fluids from a plain surface in a pool," *International Journal of Heat and Mass Transfer* 48:2407-2419, 2005.

Bellon, "Quantitation and specific detection of collagenous proteins using an enzyme-linked immunosoret assay and an immunoblotting for cyanogens bromide peptides," *Analytic Biochemistry* 150:188-202, 1985.

Böhlen et al., "Fluorometric Assay of Proteins in the Nanogram Range," *Archives of Biochemistry and Biophysics* 155:213-220, 1973.

Buongiorno et al., "Use of Nanofluids for Enhanced Economics and Safety of Nuclear Reactors," *COE-INES International Symposium*, 14 pages, Yokahama, Nov. 26-30, 2006.

Chan et al., "Quantum Dot Bioconjugates for Ultrasensitive Nonisotopic Detection," *Science* 281:2016-2018, Sep. 25, 1998.

Demers et al., "A Fluorescence-based method for determining the surface coverage and hybridization efficiency of thiol-capped oligonucleotides bound to gold thin films and nanoparticles," *Analytical Chemistry* 72:5535-5541, 2000.

Dong et al., "Study of Fluorescence Quenching and Dialysis Process of CdTe Quantum Dots, Using Ensemble Techniques and Fluorescence Correlation Spectroscopy," *J. Phys. Chem. B* 110:10069-10075, 2006.

Draper et al., "Attachment of reporter groups to specific, selected cytidine residues in RNA using a bisulfate-catalyzed transamination reaction," *Nucleic Acids Research* 12(2):989-1002, 1984.

Dubois et al., "A Versatile Strategy for Quantum Dot Ligand Exhange," *Journal of the American Chemical Society* 129(3):482-483, 2007.

Dyal et al., "Activity of *Candida rugosa* lipase Immobilized on $\gamma$-$Fe_2O_3$ Magnetic Nanoparticles," *Journal of the American Chemical Society* 125:1684-1685, 2003.

Eastman et al., "Anomalously increased effective thermal conductivities of ethylene glycol-based nanofluids containing copper nanoparticles," *Applied Physics Letters* 78(6):718-720, Feb. 5, 2001.

Gerardi, "Experimental Study of Boiling Crisis Phenomena in Nanofluids," *National Nuclear Society Student Conference*, 19 pages, Mar. 30, 2007.

Han et al., "Quantum-dot-tagged microbeads for multiplexed optical coding of biomolecules," *Nature Technology* 19:631-635, Jul. 2001.

Heafey et al., "Comparative study of the quenching of core and core-shell CdSe quantum dots by binding and non-binding nitroxides," *Photochemical and Photobiological Sciences* 6:580-584, 2007.

Heid et al., "Real time Quantitative PCR," *Genome Research* 6:986-994, 1996.

Hickman et al., "Combining Spontaneous Molecular Assembly with Microfabrication to Pattern Surfaces: Selective Binding of Isonitriles to Platinum Microwires and Characterization by Electrochemistry and Surface Spectroscopy," *Journal of the American Chemical Society* 111:7271-7272, 1989.

Hill et al., "The bio-barcode assay for the detection of protein and nucleic acid targets using DTT-induced ligand exchange," *Nature Protocols* 1(1):324-336, 2006.

Iijima et al., "Dispersion Behavior of Barium Titanate Nanoparticles Prepared by Using Various Polycarboxylic Dispersants," *Journal of the American Chemical Society* 90(9):2741-2746, 2007.

Jackson et al., "Characteristics of Nucleate Boiling with Gold Nanoparticles in Water," *Proceedings of IMECE 2006*, 2006 ASME International Mechanical Engineering Congress and Exposition, pp. 385-390, Chicago, Illinois, Nov. 5-10, 2006.

Kats et al., "Spectroscopic determination of protein concentrations from proteinase K digests," *Analytical Biochemistry* 307:212-218, 2002.

Kim et al., "A real-time PCR-based method for determining the surface coverage of thiol-capped oligonucleotides bound onto gold nanoparticles," *Nucleic Acids Research* 34(7):e54, 2006.

Kim et al., "Effects of nanoparticle deposition on surface wettability influencing boiling heat transfer in nanofluids," *Applied Physics Letters* 89(153107):1-3, 2006.

Kim et al., "Experimental studies on CHF characteristics of nanofluids at pool boiling," *International Journal of Multiphase Flow* 33:391-706, 2007.

Kim et al., "Surface wettability change during pool boiling of nanofluids and its effect on critical heat flux," *International Journal of Heat and Mass Transfer* 50:4105-4116, 2007.

Koh et al., "Magnetic Iron Oxide Nanoparticles for Biorecognition: Evaluation of surface coverage and activity," *Journal of Physical Chemistry* 110:1553-1448, 2006.

Layne, "Spectrophotometric and turbidimetric methods for measuring proteins," *Methods in Enzymology* 3:447-454, 1957.

Link et al., "Size and Temperature Dependence of the Plasmon Absorption of Colloidal Gold Nanoparticles," *Journal of Physical Chemistry B* 103(21):4212-4217, 1999.

Matsui et al., "Synthesis of cerium oxide nanoparticles by hydrothermal crystallization with citric acid," *Journal of Materials Science Letters* 21:489-491, 2002.

Matteucci et al., "Synthesis of Deoxyoligonucleotides on a Polymer Support," *Journal of the American Chemical Society* 103:3185-3191, 1981.

Milanova et al., "Role of ions in pool boiling heat transfer of pure and silica nanofluids," *Applied Physics Letters* 87(233107):1-3, 2005.

Moreno et al., "Pool Boiling Heat Transfer of Alumina-Water, Zinc Oxide-Water and Alumina-Water+Ethylene Glycol Nanofluids," *Proceedings of HT2005, 2005 ASME Summer Heat Transfer Conference*, pp. 625-632, San Francisco, California, Jul. 17-22, 2005.

Mucic et al., "Synthesis and characterization of DNA with ferrocenyl groups attached to their 5'-termini: electrochemical characterization of a redox-active nucleotide monolayer," *Chem. Comm.*, pp. 555-557, 1996.

Mueller and Brueck, "Whole Genome Amplification for Single Cell Biology," Sigma-Aldrich Corporation, St. Louis, MO.

Otsuka et al., "Quantitative and Reversible Lectin-Induced Association of Gold Nanoparticles Modified with α-Lactosyl-ω-mercapto-poly(ethylene glycol)," *Journal of the American Chemical Society* 123(34):8226-8230, 2001.

Pathak et al., "Hydroxylated quantum dots as luminescent probes for in situ hybridization," *Journal of the American Chemical Society* 123:4103-4104, 2001.

Perkins, "Protein volumes and hydration effects," *Eur. J. Biochem.* 157:169-180, 1986.

Rockenberger et al., "A New Nonhydrolytic Single-Precursor Approach in Surfactant-Capped Nanocrystals of Transition Metal Oxides," *Journal of the American Chemical Society* 121(49):11595-11596, 1999.

Santra et al., "Rapid and effective labeling of brain tissue using TAT-conjugated CdS:Mn/ZnS quantum dots," *Chemical Communications*, pp. 3144-3146, 2005.

Sun et al., "Shape-Controlled Synthesis of Gold and Silver Nanoparticles," *Science* 398:2176-2179, Dec. 13, 2002.

Thanh et al., "Development of an Aggregation-Based Immunoassay for Anti-Protein A Using Gold Nanoparticles," *Analytical Chemistry* 74(7):1624-1628, 2002.

Theofanous et al., "The boiling crisis phenomenon—Part I: nucleation and nucleate boiling heat transfer," *Experimental Thermal and Fluid Science* 26:775-792, 2002.

Theofanous et al., "The boiling crisis phenomenon—Part II: dryout dynamics and burnout," *Experimental Thermal and Fluid Science* 26:793-810, 2002.

Tsugita et al., "A rapid vapor-phase acid (hydrochloric acid and trifluoroacetic acid) hydrolysis of peptide and protein," *Journal of Biochemistry* 102:1593-1597, 1987.

Udenfriend et al., "Fluorescamine: A Reagent for Assay of Amino Acids, Peptides, Proteins and Primary Amines in the Picomole Range," *Science* 178:870-872, Nov. 24, 1972.

Vassallo et al., "Pool boiling heat transfer experiments in silica-water nano-fluids," *International Journal of Heat and Mass Transfer* 47:407-411, 2004.

Wang et al., "Effect of Surface Wettability on Active Nucleation Site Density During Pool Boiling of Water on a Vertical Surface," *Journal of Heat Transfer* 115:659-669, Aug. 1993.

Wen et al., "Experimental investigation into the pool boiling heat transfer of aqueous based γ-alumina nanofluids," *Journal of Nanoparticle Research* 7:265-274, 2005.

Woehrle et al., "Thiol-functionalized 1.5-nm gold nanoparticles through ligand exchange reactions: Scope and mechanism of ligand exchange," *Journal of the American Chemical Society* 127(7):2172-2183, 2005.

Xu et al., "Immunoassay using probe-labelling immungold nanoparticles with silver staining enhancement via surface-enhanced Raman scattering," *Analyst* 129:63-68, 2004.

Yi et al., "Water-Soluble $NaYF_4$:Yb,Er(Tm)/$NaYF_4$/Polymer Core/Shell/Shell Nanoparticles with Significant Enhancement of Upconversion Fluorescence," *Chemistry of Materials* 19:341-343, 2007.

You et al., "Effect of nanoparticles on critical heat flux of water in pool boiling heat transfer," *Applied Physics Letters* 83(16):3374-3376, Oct. 20, 2003.

Yu et al., "Water-soluble quantum dots for biomedical applications," *Biochemical and Biophysical Research Communications* 348:781-786, 2006.

International Search Report dated Sep. 23, 2008, from International Application No. PCT/US2007/023140.

International Search Report dated Dec. 16, 2009, from International Application No. PCT/US2009/045841.

\* cited by examiner

POLYMERIC CARRIERS FOR IMMUNOHISTOCHEMISTRY AND IN SITU HYBRIDIZATION

CROSS REFERENCE TO RELATED APPLICATION

This application is a divisional of U.S. patent application Ser. No. 12/154,472, filed on May 22, 2008 now U.S. Pat. No. 7,985,557, which claims the benefit of the earlier filing date of U.S. Provisional Application No. 60/931,546, filed on May 23, 2007. The entire disclosures of these prior applications are incorporated herein by reference.

FIELD

The present invention concerns molecular conjugates, particularly Fc-specific conjugates, comprising a polymeric carrier having plural reactive functional groups, embodiments of a method for making disclosed exemplary conjugates, and embodiments of a method for using the conjugates.

BACKGROUND

Biomolecular conjugates can be used in immunoassays for detecting specific target molecules in a sample. Various conjugates are known, including antibody-detectable label conjugates and antibody-enzyme conjugates, and a number of methods have been developed for making these conjugates. For example, antibody conjugates often are prepared using coupling reagents having at least two reactive groups. One of the groups is used to couple to the antibody, and another functional group is coupled to the detectable label. These coupling reactions can interfere with the performance of the conjugate for a desired purpose. For example, coupling can deactivate antibody-enzyme conjugates, such as through steric effects, deactivation of reactive functional groups critical for appropriate functioning, changes in solubility, etc. As a result, and despite prior efforts, there still is a need for molecular conjugates, and methods for their production and use, that provide greater assay sensitivity. Ventana Medical is the assignee of a number of patents and applications in this general area, including: U.S. patent application Ser. No. 11/018,897, entitled Microwave Mediated Synthesis of Nucleic Acid Probes, published as U.S. publication No. 2005/0158770, on Jul. 21, 2005; U.S. Provisional Application No. 60/739,794, filed on Nov. 23, 2005, and the corresponding utility application Ser. No. 11/603,425, entitled "Molecular Conjugate;" U.S. Provisional Application No. 60/856,133, and the corresponding utility application Ser. No. 11/982,627, entitled "Haptens, Hapten Conjugates, Compositions Thereof and Method for their Preparation and Use." Each of these prior applications is incorporated herein by reference. Example 12 of the '897 patent discloses one method for making polyacrylamide hydrazide. The '897 patent application states that the "invention provides a method for preparing a labeled cytosine, a labeled cytidine, or labeled cytidine-containing biomolecule, such as oligonucleotides, DNA molecules, RNA molecules, proteins, peptides, or other biomolecules." U.S. Patent Publication No. 2005/0158770, paragraph 0044. Moreover, the application states that "[l]inear polymers that are functionalized with fluorophores and nuclelophillic group(s) may also function as useful reporter containing moities." And "a preferred functionalized polymer is polyacrylamide hydrazide functionalized with fluorophores, particularly PAH of MW 10,000 to 20,000 bearing between 10 to 40 hydrazide groups per polymer chain." U.S. Patent Publication No. 2005/0158770, paragraph 0068. Reporter groups are defined to include "any detectable moiety commonly used for labeling probes," including haptens and proteins. U.S. Patent Publication No. 2005/0158770, paragraph 0053.

According to Scheme 11 of the '425 application, the Fc portion of an antibody is oxidized to form an aldehyde, and a thiolated hydrazide is then coupled to the Fc portion of the antibody by reaction of a hydrazide nitrogen with the carbonyl. According to Scheme 13 of the '425 application, a thiolated hydrazide coupled to the oxidized Fc portion of an antibody is reacted with alkaline phosphatase having a thiol-reactive functional group to form a conjugate. And, according to Scheme 19, a polyacrylamide hydrazide is first synthesized, and then, as stated in Example 22:

In an appropriate solvent, the resulting PAH is reacted with a thiolating agent, such as thiol-dPEG-NHS ester[1] (Quanta Biodesign, Powell, Ohio) or Traut's reagent, to thiolate a portion (for example, approximately 50-75%) of available hydrazides (z=5 to 40) and provide a polymeric multifunctional hydrazide thiol linker that can be used in the disclosed method.

[1] Applicants note that the reagent should be referred to as S-acetyl-dPEG-NHS ester.

As presently understood, all embodiments of the PAH conjugates disclosed in the '897 application have at least a portion of the reactive hydrazide functional groups thiolated as disclosed in Example 22. Moreover, it is the thiol group, provided by thiolation of the hydrazide, that is the reactive moiety used to form conjugates.

SUMMARY

Certain disclosed embodiments of the present invention concern the synthesis, derivatization, conjugation to immunoglobulins and signal amplification based on discrete, relatively short polymers, e.g., polyacrylamide hydrazide (PAH), having plural reactive functional groups that react with plural molecules of interest. Many of the disclosed embodiments concern substantially water soluble, or completely water soluble, polymers. With reference to the exemplary PAH, such polymers are completely water soluble, and may display numerous reactive hydrazides, such as greater than zero hydrazide functional groups, and more typically from about 5 up to at least 100 hydrazide groups. Reactive functional groups also can be quantified with reference to the percentage of potential positions occupied by the pertinent functional group, such as a hydrazide. For the present embodiments, the reactive functional group typically comprises at least 10%, and up to at least 50%, of the possible positions that can be reactive functional groups. Reactive functional groups, such as the hydrazide, may be derivatized with a variety of haptens. The remaining hydrazides on the carrier may be conjugated directly to the oxidized carbohydrate of the Fc region of the antibody. The low pKa of the hydrazide offers particular advantage in that the protonation of the aldehydes groups generated by carbohydrate oxidation of the antibody facilitates the conjugation of the polymer hapten carrier. Moreover, the carrier is installed at the Fc region of the antibody, away from the binding site of the IgG. The resulting conjugate displays very large signal amplification as compared to those based on Fc derivatized with single haptens.

One embodiment of the disclosed method concerns forming a molecular conjugate by coupling a specific binding molecule to a detectable label through reactive hydrazide functional groups provided by a polyacrylamide hydrazide carrier. The polyacrylamide hydrazide preferably is water soluble. The average molecular weight of the polymeric portion can vary, and typically is from as low as 50 up to at least about 100,000, more typically from about 1,000 to about 50,000, and even more typically from about 5,000 to about 40,000. Certain disclosed embodiments use polyacrylamide hydrazides having an average molecular weight of about 10,000 or less. And, for particular embodiments, the hydrazide functional group of the polyacrylamide hydrazide is non-thiolated.

A particular disclosed embodiment comprises forming a first compound by coupling the specific binding molecule to at least a portion of the reactive functional groups. At least a portion of remaining reactive functional groups of the first compound may then be coupled to a detectable label, such as a hapten. Alternatively, a polymeric carrier comprising plural reactive functional groups can be coupled to a detectable label, such as hapten. At least a portion of remaining reactive functional groups of the first compound may then be coupled to a specific binding molecule.

Particular embodiments concern antibodies as the specific binding molecule. For example, the polymeric carrier can be coupled to the Fc portion of the antibody through the reactive hydrazide functional groups. The antibody can be activated for reaction with the reactive functional groups, such as by chemically modifying a glycosylated portion of the antibody. In certain working embodiments, the antibody is chemically activated by oxidation to form a carbonyl bearing compound, such as an aldehyde.

Many of the disclosed embodiments concern using haptens as a detectable label. The hapten can be any hapten now known or hereafter discovered or developed that is suitable for practicing disclosed embodiments of the method. Many haptens are known and frequently used for analytical procedures, such as di-nitrophenyl, biotin, digoxigenin, fluorescein, rhodamine, or combinations thereof. Other haptens have been specifically developed by Ventana Medical Systems, including haptens selected from oxazoles, pyrazoles, thiazoles, nitroaryls, benzofurans, triterpenes, ureas, thioureas, rotenoids, coumarins, cyclolignans, and combinations thereof. Plural different haptens may be coupled to the polymeric carrier. Moreover, compounds, such as haptens, can be coupled to the polymeric carrier using a linker, such as an NHS-PEG linker.

One specific disclosed embodiment concerns a method for forming a molecular conjugate, comprising coupling a specific binding molecule to a detectable label by a polyacrylamide hydrazide carrier. The carrier has an average molecular weight of 10,000 or less and plural reactive, non-thiolated hydrazide functional groups.

A currently preferred embodiment using polyacrylamide hydrazide carriers comprises providing a polyacrylamide polymeric carrier, typically having an average molecular weight of about 10,000 or less, and comprising plural reactive, non-thiolated hydrazide functional groups. The Fc portion of an antibody is oxidized to form an aldehyde. The polymeric carrier is coupled to the oxidized Fc portion of the antibody through at least one reactive hydrazide functional group to form a first compound. The first compound is then coupled to at least one hapten through a reactive hydrazide functional group to form a second compound.

The present invention also concerns conjugate comprising polyacrylamide hydrazides. For example, one disclosed conjugate embodiment comprises a specific binding molecule covalently bonded to a detectable label through a reactive hydrazide functional group provided by a polyacrylamide hydrazide linker. The conjugate also can comprise a PEG-based hydrazide linker, such as compounds having a functionalized end and a distal end comprising a hydrazide or hydrazide derivative functional group. The detectable label typically is selected from an enzyme, a fluorophore, a luminophore, escent molecule, a hapten, a fluorescent nanoparticle, or combinations thereof. Exemplary enzymes include alkaline phosphatase and horseradish peroxidase. Exemplary known haptens include di-nitrophenyl, biotin, digoxigenin, fluorescein, rhodamine, or combinations thereof. Additional exemplary haptens, developed by Ventana Medical, include oxazoles, pyrazoles, thiazoles, nitroaryls, benzofurans, triterpenes, ureas, thioureas, rotenoids, coumarins, cyclolignans, or combinations thereof. The specific binding molecule often is an antibody, including anti-hapten antibodies, and anti-antibody antibodies.

Polyacrylamide hydrazide carriers also can be used in a diagnostic assay process. One disclosed embodiment of such a process comprises contacting a sample with a specific binding molecule that binds specifically to a target. The specific binding molecule is conjugated to a detectable label through the polyacrylamide hydrazide carrier. The specific binding molecule is then detected using the detectable label. The disclosed conjugates also can be used in a multiplexed assay. For example, disclosed embodiments include a multiplexed diagnostic assay for two or more different targets in a sample, where the method comprises contacting the sample with two or more specific binding molecules that bind specifically to two or more different targets. The two or more specific binding molecules are conjugated to different haptens through a reactive hydrazide functional group of a polyacrylamide hapten carrier. The sample is then contacted with two or more different anti-hapten antibodies that can be detected separately.

While certain disclosed embodiments are directed particularly to using polyacrylamide hydrazide carriers, other polymeric carriers also are contemplated. For these embodiments, one disclosed method for forming a molecular conjugate comprises coupling a specific binding molecule to a detectable label through reactive functional groups provided by a polymeric carrier. The polymeric carrier comprises a polymeric portion selected from polyacrylic acids, polyethyleneimines, polysaccharides, polyethylene-alt-maleic acids, polyamino acids or polyvinylpyrrolidones. The polymeric portion also includes plural reactive functional groups selected from hydrazines, hydrazides, hydrazine derivatives, hydrazide derivatives, guanidines, aminoguanidines, hydroxyl amines, or combinations thereof. Exemplary polysaccharide species may be selected from carbohydrates, cellulose, carboxymethylcellulose, dextran, glycogen, polyhyaluronic acid and starch. Exemplary polyamino acids may be selected from poly(arginine), poly(aspargine), poly(aspartic acid), poly(glutamic acid), poly(glutamine), poly(lysine) or combinations thereof.

For particular embodiments, the method comprises forming a first compound by coupling the specific binding molecule to at least a portion of the reactive functional groups. At least a portion of any remaining non-reacted functional groups of the first compound are coupled to a detectable label. Alternatively, the method may comprise forming a first compound by coupling a detectable label to at least a portion of the reactive functional groups, and then coupling at least a portion of remaining reactive functional groups of the first compound to a specific binding molecule.

One class of specific binding molecules is antibodies. The method may comprise coupling the polymeric carrier to the Fc portion of the antibody through a reactive functional group. Again, the antibody may be activated for reaction with the reactive functional groups, such as by chemically modifying a glycosylated portion of the antibody.

The specific binding molecule may be an antibody and the detectable label may be a hapten, as described with reference to the polyacrylamide hydrazide carriers. Plural different haptens may be coupled to the polymeric carrier, and any one or more of such haptens may be coupled to the carrier using a linker, such as PEG-based linker.

A particular embodiment of the method for forming a conjugate comprises providing a polymeric carrier comprising a polymeric portion selected from polyacrylic acids, polyethyleneimines, polysaccharides, polyethylene-alt-maleic acids, polyamino acids or polyvinylpyrrolidones. The polymeric portion includes plural reactive functional groups selected from hydrazines, hydrazides, hydrazine derivatives, hydrazide derivatives, guanidines, aminoguanidines, hydroxyl amines, or combinations thereof. The Fc portion of an antibody is oxidized to form an aldehyde. The polymeric carrier is coupled to the oxidized Fc portion of the antibody and to at least one hapten, and potentially plural different haptens, through reactive functional groups.

One disclosed embodiment of the method comprises forming a molecular conjugate by providing a polymeric carrier comprising a polymeric portion selected from polyacrylic acids, polyethyleneimines, polysaccharides, polyethylene-alt-maleic acids, polyamino acids or polyvinylpyrrolidones. The polymeric portion also includes plural reactive functional groups selected from hydrazines, hydrazides, hydrazine derivatives, hydrazide derivatives, guanidines, aminoguanidines, hydroxyl amines, or combinations thereof. A specific binding molecule is coupled to the polymer carrier through a reactive functional group. A hapten also is coupled to the polymeric carrier through a reactive functional group, the hapten being selected from oxazoles, pyrazoles, thiazoles, nitroaryls, benzofurans, triterpenes, ureas, thioureas, rotenoids, coumarins, cyclolignans, and combinations thereof.

Molecular conjugates comprising polymeric carriers other than polyacrylamide hydrazides also are described. Exemplary conjugates comprise a specific binding molecule coupled to a detectable label through a polymeric carrier comprising a polymeric portion selected from polyacrylamide-N-hydroxysuccinimide, polyacrylic acids, polyethyleneimines, polysaccharides, polyethylene-alt-maleic acids, polyamino acids or polyvinylpyrrolidones. Additional information concerning polyacrylamide-N-hydroxysuccinimide polymeric materials can be found in Pollack et al., "Enzyme Immobilization by Condensation Copolymerization into Cross-Linked Polyacrylamide Gels," JACS, Vol. 102, pages 6324-6336, which is incorporated herein by reference. The carrier also includes plural reactive functional groups selected from hydrazines, hydrazides, hydrazine derivatives, hydrazide derivatives, guanidines, aminoguanidines, hydroxyl amines, or combinations thereof. Exemplary polysaccharide species include carbohydrates, cellulose, carboxymethylcellulose, dextran, glycogen, polyhyaluronic acid and starch. Certain embodiments also use oxidized species, particularly oxidized polysaccharides. For example, dextran can be oxidized using a suitable oxidizing agent, including periodate or halogens, such as bromine, to produce a carbonyl-bearing species, typically an aldehyde, but potentially other carbonyl-bearing species, such as ketones. Exemplary polyamino acids include poly(arginine), poly(aspargine), poly(aspartic acid), poly(glutamic acid), poly(glutamine) and poly(lysine). The carrier also can be a poly(guanidine) or poly(aminoguanidine).

As with the polyacrylamide hydrazides, other disclosed polymeric carriers can be used for performing a diagnostic assay for a target in a sample. Certain disclosed embodiments comprise contacting the sample with a specific binding molecule that binds specifically to a target, wherein the specific binding molecule is conjugated to a detectable label through a polymeric carrier comprising a polymeric portion selected from polyacrylic acids, polyethyleneimines, polysaccharides, polyethylene-alt-maleic acids, polyamino acids, or polyvinylpyrrolidones. The polymeric carrier includes plural reactive functional groups selected from hydrazines, hydrazides, hydrazine derivatives, hydrazide derivatives, guanidines, aminoguanidines, hydroxyl amines, or combinations thereof. The specific binding molecule is detected using the detectable label. One embodiment of a multiplexed diagnostic assay for two or more different targets in a sample comprises contacting a sample with two or more specific binding molecules that bind specifically to two or more different targets. The two or more specific binding molecules are conjugated to different haptens through a polymeric hapten carrier having a polymeric portion selected from polyacrylamide-N-hydroxysuccinimides, polyacrylic acids, polyethyleneimines, polysaccharides, polyethylene-alt-maleic acids, polyamino acids or polyvinylpyrrolidones. As with other disclosed embodiments, the polymeric carrier also includes plural reactive functional groups selected from hydrazines, hydrazides, hydrazine derivatives, hydrazide derivatives, guanidines, aminoguanidines, hydroxyl amines, or combinations thereof. The sample is then contacted with two or more different anti-hapten antibodies that can be detected separately.

Comparisons of staining results also are provided, with single gene detection being established using the exemplary PAH disclosed embodiment. Similarly, the signal of streptavidin functionalized quantum dots is greatly enhanced in Fc derivatized polymeric biotin carrier at Fc. Under in situ hybridization of the HER2 DNA gene probe, the polymeric biotin carrier at Fc enhances the detection of quantum dot signal compared to a non-polymeric biotin link. Certain disclosed embodiments concern one particular polymeric hapten carrier, namely PAH; however, many different carriers may be synthesized and used as disclosed herein. These include, by way of example and without limitation, polyacrylic, polyglucoside, polyglutamates, polylysines, polyaspartates suitably derivatized with the haptens may all be used. Similarly, the scope of the invention is not limited to biotin-streptavidin-based systems. Rather, a wide variety of haptens and corresponding antibodies conjugated to the signal generating entities, e.g. enzymes, nanoparticles, quantum dots, fluorophores, chemiluminophores, also may be used for the disclosed embodiments.

The foregoing and other objects, features, and advantages of the invention will become more apparent from the following detailed description, which proceeds with reference to the accompanying figures.

DETAILED DESCRIPTION

I. Abbreviations

Figure 1:
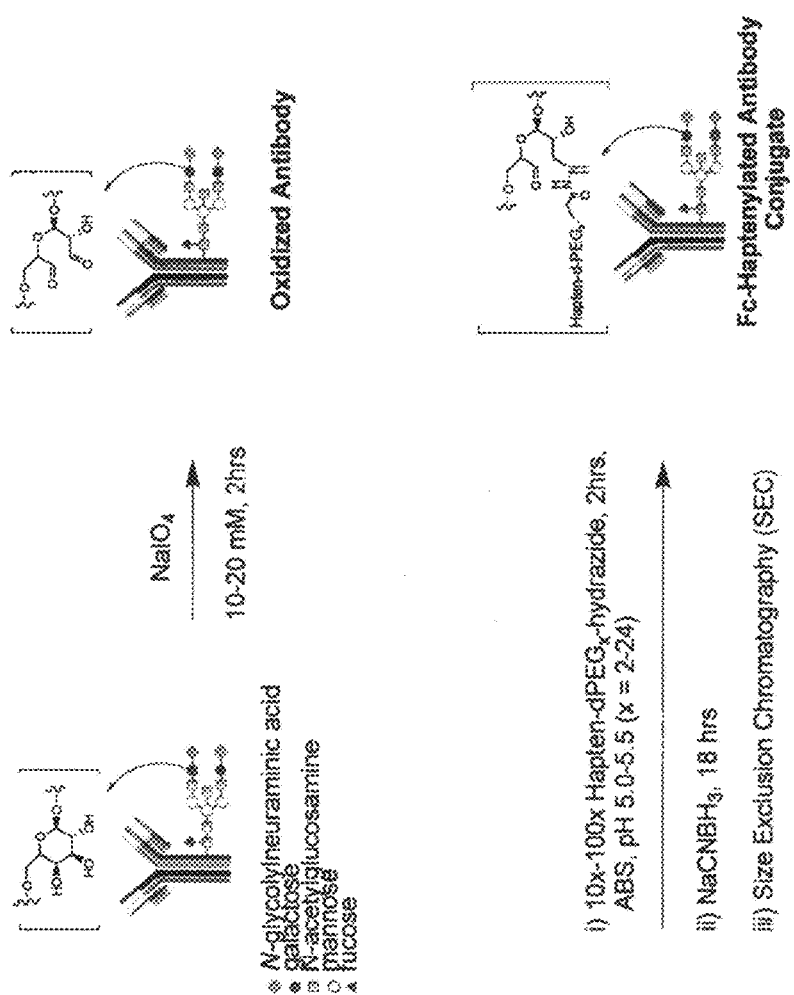
FIG. 1 illustrates one embodiment of a method for synthesizing an Fc-specific haptenylated antibody conjugate.

Ab—antibody
(Ab-AP)—antibody-alkaline phosphatase conjugate
ABS—acetate buffered saline.
AP—alkaline phosphatase
BSA—bovine serum albumin
CMV—cytomegalovirus dPEG—discrete polyethylene glycol, such as dPEG$_4$, which refers to a discretely sized PEG compound having 4 ether oxygen atoms.

EBER—Epstein-Barr virus early RNA

DL—detectable label

Fc—fragment crystallizable

HRP—horseradish peroxidase

IHC—immunohistochemistry

ISH—in situ hybridization

MAL—maleimide

MBCH—mercaptobutyric acid carbohydrazide

MBH—mercaptobutyric acid hydrazide

NHS—N-hydroxy-succinimide

SBM—specific binding molecule

SEC—size exclusion chromatography

SISH—silver in situ hybridization

II. Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all amino acid sizes, and all molecular weight or molecular mass values, given for polypeptides or other compounds are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various examples of this disclosure, the following explanations of specific terms are provided:

Amplification: Certain embodiments of the present invention allow a single target to be detected using plural visualization complexes, where the complexes can be the same or different, to facilitate identification and/or quantification of a particular target.

Analog, Derivative or Mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: "Antibody" collectively refers to immunoglobulins or immunoglobulin-like molecules (including by way of example and without limitation, IgA, IgD, IgE, IgG and IgM, combinations thereof, and similar molecules produced during an immune response in any vertebrate, for example, in mammals such as humans, goats, rabbits and mice), as well as non-mammalian species, such as shark immunoglobulins. "Antibody" also includes antibody fragments that specifically bind to a molecule of interest (or a group of highly similar molecules of interest) to the substantial exclusion of binding to other molecules (for example, antibodies and antibody fragments that have a binding constant for the molecule of interest that is at least $10^3$ M$^{-1}$ greater, at least $10^4$ M$^{-1}$ greater or at least $10^5$ M$^{-1}$ greater than a binding constant for other molecules in a biological sample.

More particularly, "antibody" refers to a polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy (V$_H$) region and the variable light (V$_L$) region. Together, the V$_H$ region and the V$_L$ region are responsible for binding the antigen recognized by the antibody.

This includes intact immunoglobulins and the variants and portions of them well known in the art. Antibody fragments include proteolytic antibody fragments [such as F(ab')$_2$ fragments, Fab' fragments, Fab'-SH fragments and Fab fragments as are known in the art], recombinant antibody fragments (such as sFv fragments, dsFv fragments, bispecific sFv fragments, bispecific dsFv fragments, F(ab)'$_2$ fragments, single chain Fv proteins ("scFv"), disulfide stabilized Fv proteins ("dsFv"), diabodies, and triabodies (as are known in the art), and camelid antibodies (see, for example, U.S. Pat. Nos. 6,015,695; 6,005,079-5,874,541; 5,840,526; 5,800,988; and 5,759,808). An scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (□) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds RET will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

Antigen: A compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens. In one example, an antigen is a *Bacillus* antigen, such as γPGA.

Avidin: Any type of protein that specifically binds biotin to the substantial exclusion of other small molecules that might be present in a biological sample. Examples of avidin include avidins that are naturally present in egg white, oilseed protein (e.g., soybean meal), and grain (e.g., corn/maize) and streptavidin, which is a protein of bacterial origin.

Binding Affinity: The tendency of one molecule to bind (typically non-covalently) with another molecule, such as the tendency of a member of a specific binding pair for another member of a specific binding pair. A binding affinity can be measured as a binding constant, which binding affinity for a specific binding pair (such as an antibody/antigen pair) can be at least $1\times10^5$ $M^{-1}$, such as at least $1\times10^6$ $M^{-1}$, at least $1\times10^7$ $M^{-1}$ or at least $1\times108$ $M^{-1}$. In one embodiment, binding affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity for an antibody/antigen pair is at least about $1\times10^8$ $M^{-1}$. In other embodiments, a high binding affinity is at least about $1.5\times10^8$ $M^{-1}$, at least about $2.0\times10^8$ $M^{-1}$, at least about $2.5\times10^8$ $M^{-1}$, at least about $3.0\times10^8$ $M^{-1}$, at least about $3.5\times10^8$ $M^{-1}$, at least about $4.0\times10^8$ $M^{-1}$, at least about $4.5\times10^8$ $M^{-1}$, or at least about $5.0\times10^8$ $M^{-1}$.

Carrier: A molecule to which a hapten or an antigen can be bound. Carrier molecules include immunogenic carriers and specific-binding carriers. When bound to an immunogenic carrier, the bound molecule may become immunogenic. Immunogenic carriers may be chosen to increase the immunogenicity of the bound molecule and/or to elicit antibodies against the carrier, which are diagnostically, analytically, and/or therapeutically beneficial. Covalent linking of a molecule to a carrier can confer enhanced immunogenicity and T-cell dependence (Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, proteins from bacteria or viruses), semi-synthetic or synthetic materials containing one or more functional groups to which a reactant moiety can be attached. Specific binding carriers can by any type of specific binding moiety, including an antibody, an avidin, etc.

Chimeric Antibody: An antibody that has framework residues from one species, such as human, and CDRs (which generally confer antigen binding) from another species, such as a murine antibody that specifically binds RET.

Conjugate: A "conjugate" refers to two or more molecules (and/or materials such as nanoparticles) that are covalently linked into a larger construct. In some embodiments, a conjugate includes one or more biomolecules (such as peptides, proteins, enzymes, sugars, polysaccharides, lipids, glycoproteins, and lipoproteins) covalently linked to one or more other molecules, such as one or more other biomolecules. In other embodiments, a conjugate includes one or more specific-binding molecules (such as antibodies) covalently linked to one or more detectable labels (such as a fluorophore, a luminophore, fluorescent nanoparticles, haptens, enzymes and combinations thereof).

Conjugating, Coupling, Joining, Bonding or Linking: Covalently linking one molecule to another molecule to make a larger molecule. For example, making two polypeptides into one contiguous polypeptide molecule, or to covalently attaching a hapten or other molecule to a polypeptide, such as an scFv antibody. In the specific context, the terms include reference to joining a ligand, such as an antibody moiety, to an effector molecule ("EM"). The linkage can be either by chemical or recombinant means.

Coupling a specific binding molecule to a detectable label through reactive hydrazide functional groups: Refers to covalently linking a specific binding molecule to another molecule by a direct covalent bond to a nitrogen atom of a hydrazide functional group.

Detectable Label: A molecule or material that can produce a detectable (such as visually, electronically or otherwise) signal that indicates the presence and/or concentration of the label in a sample. When conjugated to a specific binding molecule, the detectable label can be used to locate and/or quantify the target to which the specific binding molecule is directed. Thereby, the presence and/or concentration of the target in a sample can be detected by detecting the signal produced by the detectable label. A detectable label can be detected directly or indirectly, and several different detectable labels conjugated to different specific-binding molecules can be used in combination to detect one or more targets. For example, a first detectable label such as a hapten conjugated to an antibody specific to a target can be detected indirectly through the use of a second detectable label that is conjugated to a molecule that specifically binds the first detectable label. Multiple detectable labels that can be separately detected can be conjugated to different specific binding molecules that specifically bind different targets to provide a multiplexed assay that can provide simultaneous detection of the multiple targets in a sample. A detectable signal can be generated by any known or yet to be discovered mechanism including absorption, emission and/or scattering of a photon (including radio frequency, microwave frequency, infrared frequency, visible frequency and ultra-violet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Particular examples of detectable labels include enzymes such as horseradish peroxidase, alkaline phosphatase, acid phosphatase, glucose oxidase, β-galactosidase or β-glucuronidase; fluorphores such as fluoresceins, luminophores, coumarins, BODIPY dyes, resorufins, and rhodamines (many additional examples of fluorescent molecules can be found in *The Handbook—A Guide to Fluorescent Probes and Labeling Technologies*, Molecular Probes, Eugene, Oreg.); nanoparticles such as quantum dots (obtained, for example, from QuantumDot Corp, Invitrogen Nanocrystal Technologies, Hayward, Calif.; see also, U.S. Pat. Nos. 6,815,064, 6,682,596 and 6,649,138, each of which patents is incorporated by reference herein); metal chelates such as DOTA and DPTA chelates of radioactive or paramagnetic metal ions like $Gd^{3+}$; and liposomes, for example, liposomes containing trapped fluorescent molecules. Where the detectable label includes an enzyme, a detectable substrate such as a chromogen, a fluorogenic compound, or a luminogenic compound can be used in combination with the enzyme to generate a detectable signal (A wide variety of such compounds are commercially available, for example, from Invitrogen Corporation, Eugene Oreg.). Particular examples of chromogenic compounds include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet. Alternatively, an enzyme can be used in a metallographic detection scheme. Metallographic detection methods include using an enzyme such as alkaline phosphatase in combination with a water-soluble metal ion and a redox-inactive substrate of the enzyme. The substrate is converted to a redox-active agent by the enzyme, and the redox-active agent reduces the metal ion, causing it to form a detectable precipitate. (See, for example, co-pending U.S. patent application Ser. No. 11/015,646, filed Dec. 20, 2004, PCT Publication No. 2005/003777 and U.S. Patent Application Publication No. 2004/0265922; each of which is incorporated by reference herein). Metallographic detection methods include using an oxido-reductase enzyme (such as horseradish peroxidase) along with a water soluble metal ion, an oxidizing agent and a reducing agent, again to for form a detectable precipitate. (See, for example, U.S. Pat. No. 6,670,113, which is incorporated by reference herein).

Haptens are small molecules that are specifically bound by antibodies, although by themselves they will not elicit an immune response in an animal and must first be attached to a larger carrier molecule such as a protein to generate an immune response. Examples of haptens include di-nitrophenyl, biotin, digoxigenin, and fluorescein. Additional examples of oxazole, pyrazole, thiazole, nitroaryl, benzofuran, triperpene, urea, thiourea, rotenoid, coumarin and cyclolignan haptens are disclosed in co-pending U.S. Provisional Patent Application No., 60/856,133, filed Nov. 1, 2006, which is incorporated by reference herein.

Epitope: An antigenic determinant. These are particular chemical groups or contiguous or non-contiguous peptide sequences on a molecule that are antigenic, that is, that elicit a specific immune response. An antibody binds a particular antigenic epitope.

Fc-specific Conjugate: A conjugate of an immunoglobulin (or fragment thereof) in which a second molecule (such as a detectable label) is covalently bonded to the glycosylated portion of the immunoglobulin (or a fragment of an immunoglobulin that retains the glycosylated portion). The glycosylated portion of an immunoglobulin is found in the Fc-region, which is a region of an immunoglobulin that is located on the heavy chains of the immunoglobulin at positions outside of the portion of the immunoglobulin that is responsible for the specific binding activity of the immunoglobulin.

Hapten: A molecule, typically a small molecule that can combine specifically with an antibody, but typically is substantially incapable of being immunogenic except in combination with a carrier molecule.

Homopolymer: This term refers to a polymer formed by the bonding together of multiple units of a single type of molecular species, such as a single monomer (for example, an amino acid).

Humanized Antibody: An antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Humanized Immunoglobulin: an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences.

Hydrazide or Hydrazide Group: A hydrazide group (—CO—NH—$NH_2$); a carbohydrazide group (—NH—NH—CO—NH—$NH_2$); a semicarbazide group (—NH—CO—NH—$NH_2$); a thiosemicarbazide group (—NH—CS—NH—$NH_2$); a thiocarbazide group (—NH—NH—CS—NH—$NH_2$); a carbonic acid dihydrazine group (—NH—CO—NH—NH—CO—NH—$NH_2$) or a sulfur containing derivative thereof; or a hydrazine carboxylate group (—O—CO—NH—NH$_2$) or a sulfur-containing derivative thereof.

Hydrazide-reactive Group: A group of atoms that can react with and form a covalent bond to a hydrazide group. Aldehyde and ketone groups are examples of hydrazide-reactive groups. Hydrazide-reactive groups can be an intrinsic part of a molecule or can be introduced to a molecule. One method for introducing an aldehyde group (a hydrazide-reactive group) into polysaccharides and glycoproteins (including antibodies) is by oxidation such as periodate-mediated oxidation of vicinal diols. In addition, double bonds in unsaturated fatty acids and ceramides can be converted to diols by osmium tetroxide and then oxidized by periodate to aldehydes. Furthermore, N-terminal serine and threonine residues of peptides and proteins can be selectively oxidized by periodate to aldehyde groups, permitting selective modification of certain proteins such as corticotrophin and β-lactamase. Modification of periodate-oxidized antibodies does not typically inactivate the antibody. Varying the concentration of sodium periodate during the oxidation reaction gives some specificity with regard to the types of sugar residues that are modified. For example, sodium periodate at a concentration of 1 mM at 0° C. typically cleaves only at the adjacent hydroxyls between carbon atoms 7, 8 and 9 of sialic acid residues. Oxidizing polysaccharides using 10 mM or greater concentrations of sodium periodate results in oxidation of sugar residues other than sialic acid, thereby creating many aldehydes on a given polysaccharide. A suitable general protocol is described by Hermanson, "Bioconjugate Techniques," Academic Press, San Diego, 1996, ISBN 0-12-342336-8, which is incorporated by reference herein. Another method for introducing aldehydes into biomolecules is through the use of specific sugar oxidases, for example, galactose oxidase, which is an enzyme that oxidizes terminal galactose residues to aldehydes, particularly in glycoproteins. When galactose residues are penultimate to sialic acid residues, neuramidase can be used to remove the sialic acid residue and expose galactose as the terminal residue. A protocol for using a combination of neuramidase and galactose oxidase to oxidize galactose residues to provide a reactive aldehyde group is provided in Hermanson, "Bioconjugate Techniques," Academic Press, San Diego, 1996, ISBN 0-12-342336-8, which is incorporated by reference herein. Aldehydes also can be introduced to a molecule by reacting an amine group of a molecule with an NHS-aldehyde such as succinimidyl p-formylbenzoate (SFB) or succinimidyl p-formylphenoxyacetate (SFPA) (Invitrogen Corp., Eugene, Oreg.). Alternatively, bis-aldehyde compounds such as glutaraldehyde can be used to modify an amine group to provide an aldehyde group. Again, suitable protocols are provided in Hermanson, "Bioconjugate Techniques," Academic Press, San Diego, 1996, ISBN 0-12-342336-8, which is incorporated by reference herein.

Hydrazine, Hydrazine Derivatives: Chemical compounds or moieties typically having a formula $N_2H_4$. Hydrazine derivatives are compounds or moieties where at least one, and potentially plural hydrogen atoms of hydrazine are replaced with other groups, such as aliphatic groups, particularly alkyl groups, and even more typically lower alkyl groups.

Immune Response: A response of a cell of the immune system, such as a B-cell, T-cell, macrophage or polymorphonucleocyte, to a stimulus. An immune response can include any cell of the body involved in a host defense response for example, an epithelial cell that secretes interferon or a cytokine. An immune response includes, but is not limited to, an innate immune response or inflammation.

Immunogenic Conjugate or Composition: A term used herein to mean a composition useful for stimulating or eliciting a specific immune response (or immunogenic response) in a vertebrate. In some embodiments, the immunogenic response is protective or provides protective immunity, in that it enables the vertebrate animal to better resist infection or disease progression from the organism against which the immunogenic composition is directed. One specific example of a type of immunogenic composition is a vaccine.

Immunogen: A compound, composition, or substance which is capable, under appropriate conditions, of stimulating the production of antibodies or a T-cell response in an animal, including compositions that are injected or absorbed into an animal.

Immunologically Effective Dose: An immunologically effective dose of the disclosed conjugates of the disclosure is therapeutically effective and will prevent, treat, lessen, or attenuate the severity, extent or duration of a disease or condition.

Immunologically Reactive Conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (such as temperature, osmolarity, pH) that are typical inside a living mammal or a mammalian cell. While it is recognized that some organs are subject to extreme conditions, the intraorganismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Isolated: An "isolated" microorganism (such as a virus, bacterium, fungus, or protozoan) has been substantially separated or purified away from microorganisms of different types, strains, or species. Microorganisms can be isolated by a variety of techniques, including serial dilution and culturing.

An "isolated" biological component (such as a protein or organelle) has been substantially separated or purified away from other biological components in the cell of the organism in which the component naturally occurs, such as other chromosomal and extra-chromosomal DNA and RNA, proteins, and organelles. Proteins that have been "isolated" include proteins purified by standard purification methods. The term also embraces proteins prepared by recombinant expression in a host cell, as well as chemically synthesized proteins, or fragments thereof.

Ki-67: a nuclear antigen (protein) involved in cellular proliferation useful for cancer diagnosis as it is expressed in all stages of the cell cycle except for G0 (the resting phase).

Linker Peptide: A peptide within an antibody binding fragment (such as an Fv fragment) which serves to indirectly bond the variable heavy chain to the variable light chain. "Linker" can also refer to a peptide serving to link a targeting moiety, such as a scFv, to an effector molecule, such as a cytotoxin or a detectable label.

Mammal: This term includes both human and non-human mammals. Similarly, the term "subject" includes both human and veterinary subjects.

Molecule of Interest or Target: A molecule for which the presence, location and/or concentration is to be determined. Examples of molecules of interest include proteins tagged with haptens.

Monoclonal Antibody: An antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

Multiplex, -ed, -ing: Embodiments of the present invention allow multiple targets in a sample to be detected substantially simultaneously, or sequentially, as desired, using plural different conjugates. Multiplexing can include identifying and/or quantifying peptides, proteins, both individually and in any and all combinations. Multiplexing also can include detecting two or more of a messenger and a protein in a cell in its anatomic context.

Nanoparticle: A nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. A nanoparticle can produce a detectable signal, for example, through absorption and/or emission of photons (including radio frequency and visible photons) and plasmon resonance.

Neoplasia and Tumor: The process of abnormal and uncontrolled growth of cells. Neoplasia is one example of a proliferative disorder.

The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Non-thiolated: Conjugates that do not include a sulfur atom between the polymeric backbone of a carrier and the specific binding molecule.

Peptide Nucleic Acid: Peptide nucleic acids are nucleic acid mimics comprising a psuedopeptide backbone. Peptide nucleic acid oligomers form stable duplex structures with complementary DNA, RNA (or PNA) oligomers, and they can also bind to targets in duplex DNA by helix invasion. The history, properties and applications of peptide nucleic acids in drug discovery and DNA detection are presented in the book "Peptide Nucleic Acids." Peptide nucleic acids were originally designed as ligands for recognizing double stranded DNA. The nucleobases of DNA were retained, but the deoxyribose phosphodiester backbone of DNA was replaced by a pseudo-peptide backbone. Exemplary peptide nucleic acids include homo-thymine peptide nucleic acids.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Protein: A molecule, particularly a polypeptide, comprised of amino acids.

Purified: The term "purified" does not require absolute purity; rather, it is intended as a relative term. Thus, for example, a purified peptide, protein, conjugate, or other active compound is one that is isolated in whole or in part from proteins or other contaminants. Generally, substantially purified peptides, proteins, conjugates, or other active compounds for use within the disclosure comprise more than 80% of all macromolecular species present in a preparation prior to admixture or formulation of the peptide, protein, conjugate or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, conjugate or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

Quantum Dot: A nanoscale particle that exhibits size-dependent electronic and optical properties due to quantum confinement. Quantum dots have, for example, been constructed of semiconductor materials (e.g., cadmium selenide and lead sulfide) and from crystallites (grown via molecular beam epitaxy), etc. A variety of quantum dots having various surface chemistries and fluorescence characteristics are commercially available from Invitrogen Corporation, Eugene, Oreg. (see, for example, U.S. Pat. Nos. 6,815,064, 6,682,596 and 6,649,138, each of which patents is incorporated by reference herein). Quantum dots are also commercially available from Evident Technologies (Troy, N.Y.). Other quantum dots include alloy quantum dots such as ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs, and InGaN quantum dots (Alloy quantum dots and methods for making the same are disclosed, for example, in US Application Publication No. 2005/0012182 and PCT Publication WO 2005/001889).

Reactive Groups: Formulas throughout this application refer to "reactive groups," which can be any of a variety of groups suitable for coupling a first unit to a second unit as described herein. For example, the reactive group might be an amine-reactive group, such as an isothiocyanate, an isocyanate, an acyl azide, an NHS ester, an acid chloride, such as sulfonyl chloride, aldehydes and glyoxals, epoxides and oxiranes, carbonates, arylating agents, imidoesters, carbodiimides, anhydrides, and combinations thereof. Suitable thiol-reactive functional groups include haloacetyl and alkyl halides, maleimides, aziridines, acryloyl derivatives, arylating agents, thiol-disulfide exchange reagents, such as pyridyl disulfides, TNB-thiol, and disulfide reductants, and combinations thereof. Suitable carboxylate-reactive functional groups include diazoalkanes, diazoacetyl compounds, carbonyldiimidazole compounds, and carbondiimides. Suitable hydroxyl-reactive functional groups include epoxides and oxiranes, carbonyldiimidazole, N,N'-disuccinimidyl carbonates or N-hydroxysuccinimidyl chloroformates, periodate oxidizing compounds, enzymatic oxidation, alkyl halogens, and isocyanates. Aldehyde and ketone-reactive functional groups include hydrazines, Schiff bases, reductive amination products, Mannich condensation products, and combinations thereof. Active hydrogen-reactive compounds include diazonium derivatives, mannich condensation products, iodination reaction products, and combinations thereof. Photoreactive chemical functional groups include aryl azides, halogenated aryl azides, benzophonones, diazo compounds, diazirine derivatives, and combinations thereof.

Sample: The term "sample" refers to any liquid, semi-solid or solid substance (or material) in or on which a target can be present. In particular, a sample can be a biological sample or a sample obtained from a biological material. Examples of biological samples include tissue samples and cytology samples, with more particular examples including, peripheral blood, urine, saliva, tissue biopsy, surgical specimen, amniocentesis samples and autopsy material.

SISH Chromogen A: a silver acetate solution.
SISH Chromogen B: a hydroquinone solution.
SISH Chromogen C: a hydrogen peroxide solution.

Specific Binding Moiety: A member of a specific-binding pair. Specific binding pairs are pairs of molecules that are characterized in that they bind each other to the substantial exclusion of binding to other molecules (for example, specific binding pairs can have a binding constant that is at least $10^3$ $M^{-1}$ greater, $10^4 M^{-1}$ greater or $10^5 M^{-1}$ greater than a binding constant for either of the two members of the binding pair with other molecules in a biological sample). Particular examples of specific binding moieties include specific binding proteins (for example, antibodies, lectins, avidins such as streptavidins, and protein A). Specific binding moieties can also include the molecules (or portions thereof) that are specifically bound by such specific binding proteins.

Target: Any molecule for which the presence, location and/or concentration is or can be determined. Examples of target molecules include proteins and haptens, such as haptens covalently bonded to proteins. Target molecules are typically detected using one or more conjugates of a specific binding molecule and a detectable label.

Therapeutically Effective Amount: A quantity of a specified agent sufficient to achieve a desired effect in a subject being treated with that agent. For example, this may be the amount of a conjugate useful in increasing resistance to, preventing, ameliorating, and/or treating infection and disease. Ideally, a therapeutically effective amount of an agent is an amount sufficient to increase resistance to, prevent, ameliorate, and/or treat infection and without causing a substantial cytotoxic effect in the subject. The effective amount of an agent useful for increasing resistance to, preventing, ameliorating, and/or treating infection and disease in a subject will be dependent on the subject being treated, the severity of the affliction, and the manner of administration of the therapeutic composition.

Vaccine: A vaccine is a pharmaceutical composition that elicits a prophylactic or therapeutic immune response in a subject. In some cases, the immune response is a protective response. Typically, a vaccine elicits an antigen-specific immune response to an antigen of a pathogen, for example, a bacterial or viral pathogen, or to a cellular constituent correlated with a pathological condition. A vaccine may include a polynucleotide, a peptide or polypeptide, a polysaccharide, a virus, a bacteria, a cell or one or more cellular constituents. In some cases, the virus, bacteria or cell may be inactivated or attenuated to prevent or reduce the likelihood of infection, while maintaining the immunogenicity of the vaccine constituent.

III. Introduction

Certain disclosed embodiments concern a method for forming a conjugate of two or more molecules, and conjugates made by the method. A person of ordinary skill in the art will recognize that the disclosed method is useful for forming any combination of molecules having functional groups that can react with a reactive functional group on a polymeric carrier, such as a hydrazide functional group. The specific conjugates disclosed to exemplify the invention should not be construed to limit the scope of the invention. For example, although certain of the disclosed conjugates are antibody-polymeric hapten carrier conjugates, conjugates between other biomolecules and other detectable labels (such as haptens, fluorophores, luminophores, fluorescent labels, fluorescent nanoparticles and fluorescent proteins, such as green fluorescent protein) also are within the scope of the disclosure.

One embodiment of the disclosed method includes reacting a polymer having plural reactive functional groups (polymeric carrier), such as plural reactive hydrazide groups, or combinations of plural different functional groups, with a first molecule (such as an antibody) having a group that can react with the reactive functional group provided by the polymeric carrier. For example, if the reactive functional group is a hydrazide, then the functional group can be a carbonyl functional group, such as an aldehyde. The first molecule includes at least one remaining reactive functional group provided by the polymeric carrier that then can be reacted with a second molecule, such as a hapten directly, a hapten with a linker, or both. Alternatively, a conjugate could be formed comprising a polymeric carrier and a hapten and/or hapten-linker, which is then reacted with the second molecule. In this example, the second molecule might be an antibody. As yet another alternative, plural different polymeric carriers, such as carriers for haptens, may be coupled to a second molecule, such as an antibody. In particular embodiments, the polymeric carrier is a polyacrylic hydrazide that is coupled to an antibody, preferably solely at the Fc region of the antibody, and plural hapten and/or hapten-linker compounds, such as PEG-biotin, PEG-DNP, fluorescein, etc. are coupled to the polymeric hapten carrier.

A further disclosed aspect is a kit that includes a disclosed linker and instructions for performing the disclosed method for making a conjugate. Also disclosed are methods for using disclosed conjugates to detect a target in a sample.

IV. Polymeric Carriers

Embodiments of the disclosed invention concern using polymeric materials as carriers, such as hapten carriers. The polymeric materials considered generally most useful for the present invention have two features: a repeating monomeric unit, or units, characteristic of a particular polymer; and plural reactive functional groups, where the reactive functional groups may be the same or different, that are associated with a repetitive polymeric unit.

A. Polymeric Materials

A person of ordinary skill in the art will appreciate that polymeric materials other than polyacrylamides can be used to practice disclosed embodiments of the present invention. Solely by way of example, and without limitation, these additional polymeric backbone materials include:

1. polyacrylic acids [e.g. $(CH_2CHCO_2H)_n$];
2. polyethyleneimines [e.g. $H(NHCH_2CH_2)_nNH_2$];
3. polystyrenesulfonates, typically having a formula

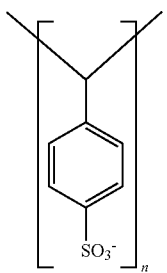

4. polysaccharides, which are a class of high-molecular-weight carbohydrates in which monosaccharides are glycosidically joined with the elimination of water. Polysaccharide typically refers to those polymers which contain 10 or more monosaccharide residues. Polysaccharides such as starch, glycogen, dextran, and polyglucosides, may include several thousand units. Polymers of relatively low molecular weight, consisting of two to nine monosaccharide residues, are referred to as oligosaccharides. Unless otherwise noted or the context clearly indicates otherwise, "polysaccharide" as used herein includes both oligosaccharides and polymers having more than 9 monosaccharide residues. Polysaccharides, such as cellulose or starch, produce only one monosaccharide type (D-glucose) on complete hydrolysis, and hence are termed homopolysaccharides. Heteropolysaccharides, such as hyaluronic acid, produce more than one monosaccharide type on hydrolysis. With specific reference to hyaluronic acid the monomers are N-acetylglucosamine and D-glucuronic acid. Exemplary polysaccharides include starch, glycogen, dextran, carboxymethylcellulose, etc.);

5. polyethylene-alt-maleic acid;
6. poly(arginine), poly(aspargine), poly(aspartic acid), poly(glutamic acid), poly(glutamine) and poly(lysine); and
7. polyvinylpyrrolidone (PVP), typically having a formula

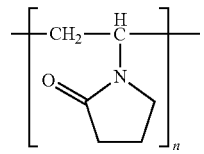

A person of ordinary skill in the art will appreciate that derivatives of these exemplary polymeric materials are suitable for use with disclosed embodiments of the present invention, and further that polymeric materials in addition to those disclosed herein to exemplify the invention also can be used as carriers.

Certain polymeric materials within the disclosure of the present invention can be obtained commercially. For example, many of the disclosed polymers are commercially available from Aldrich in various molecular weights. Alternatively, a polymeric material can be purchased or prepared, and then subsequently derivatized to include desired functional groups. This process can be exemplified by reference to the polyacrylamide hydrazides, whereby a polyacrylamide is derivatized to include plural hydrazide functional groups by microwave mediated reaction with hydrazine. Similarly, polymers, such as polyacrylamides, may be reacted with any substituted compound, such as aminoguanidines. As yet another alternative approach, monomeric units suitable for forming a desired polymeric backbone, and comprising desired functional groups, can be polymerized to form desired polymeric carriers according to disclosed embodiments of the present invention. This process allows using alternating copolymers comprising regular alternating A and B units, periodic copolymers with A and B units arranged in a repeating sequence (e.g. $(A-B-A-B-B-A-A-A-B-B-B)_n$, random copolymers with random sequences of monomer A and B, statistical copolymers in which the ordering of the distinct monomers within the polymer sequence obeys known statistical rules, block copolymers comprised of two or more homopolymer subunits linked by covalent bonds, homopolymer units having an intermediate non-repeating subunit, known as a junction block, block copolymers with two or three distinct blocks, such as diblock and triblock copolymers, linear copolymers having a single main chain, branched copolymers having a single main chain with one or more polymeric side chains, graft copolymers having side chains structurally distinct from the main chain, star copolymers, brush copolymers, comb copolymers, dendrimers, etc.

The size of the polymeric material also may be an important consideration for certain embodiments of the present application. For example, it currently is believed that the average molecular weight of the polymeric carrier should be from about 50 to about 100,000, more typically from about 1,000 to about 50,000, and even more typically from about 5,000 to about 40,000, and yet even more typically from about 10,000 to about 30,000. Certain disclosed polyacrylamide hydrazide embodiments contemplate using a polymeric material having an average molecular weight of 10,000 or less, although polyacrylamides having substantially larger average molecular weights also can be used. Additional guidance for selecting a particular molecular weight or molecular weight distribution for the polymer can be provided by considering physical properties of the polymeric product. For example, the molecular weight of the polymeric carrier can be an important consideration, such as for determining the solubility, particularly aqueous solubility, of the polymeric carrier or the ability of the polymeric carrier conjugates to penetrate a sample to which a conjugate may be applied, and hence perform as desired. A person of ordinary skill in the art also will appreciate that an optimal average molecular weight may well depend on the particular polymeric material, the reactive functional group or groups, and the intended use for the material.

Many of the disclosed embodiments are primarily useful for aqueous applications. As a result, the polymeric carrier preferably should be substantially soluble in water.

Polymeric backbones used with disclosed embodiments of the present invention can be substantially non-crosslinked structures. Alternatively, the polymeric portion can be substantially crosslinked.

B. Reactive Functional Groups

Any reactive functional group that can be used to couple components as disclosed herein can be useful for practicing the present invention. Certain embodiments concern reactive functional groups where there are at least two adjacent heteroatoms. One purpose for selecting such functional groups is to take advantage of their increased nucleophilicity, such as may result, without limiting the invention to a theory of operation, by the alpha effect, relative to compounds that may have a functional group comprising one or more heteroatoms, but not having two adjacent heteroatoms. Certain exemplary such functional groups are hydrazines, hydrazides, hydroxyl amines (—RNOH), a hydrazide thiol, as disclosed in assignee's prior "Molecular Conjugate" U.S. application Ser. No. 11/603,425.

With reference specifically to hydrazides, such functional groups typically have a formula —NR—NR$_1$R$_2$, where R-R$_2$ are hydrogen. The hydrazide may be a substituted hydrazide, i.e. where at least one of R-R$_2$ is other than hydrogen, such that R-R$_2$ independently are hydrogen, aliphatic, such as a lower (typically 20 or fewer, and even more typically 10 or fewer carbon atoms) alkyl group, heteroaliphatic, aromatic, and/or heteroaromatic. As another example, it also is possible to use functional groups that are electron donating so that the nucleophilicity of the attacking heteroatom, such as nitrogen, is further increased. Suitable functional groups also can be derivatives of a hydrazide. Exemplary such functional groups include dihydrazides [—(RN)—NR$_1$CO—NR$_2$—NR$_3$R$_4$], semicarbazides [—NRCO—NR$_1$NR$_2$R$_3$], thiosemicarbazides [—NR—CS—NR1-NR$_2$R$_3$], thiocarbazides [—NR—NR$_1$—CS—NR$_2$—NR$_3$R$_4$], carbonic acid dihydrazine [—NR—CO—NR$_1$—NR$_2$—CO—NR$_2$—NR$_4$R$_5$], sulfur containing derivatives of carbonic acid dihydrazines, hydrazine carboxylates [—O—CO—NR—NR$_1$R$_2$], or sulfur containing derivatives of hydrazine carboxylates, aminoguanidines, etc. With reference to these exemplary groups, R-R$_5$ typically are hydrogen, but also can be independently hydrogen, aliphatic, heteroaliphatic, aromatic, heteroaromatic, etc.

C. Obtaining Polymeric Carriers

Disclosed embodiments of polymeric carriers generally can be purchased or can be made using methods known in the art. A number of working embodiments illustrate polymeric carriers with reference to polyacrylamide hydrazide, where the polymeric backbone is based on acrylamide, and the carrier further comprises plural reactive hydrazide functional groups. Polyacrylamide can be made as disclosed in Example 1.

A general formula for polyacrylamide hydrazide is provided below.

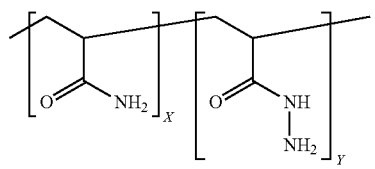

With reference to this general formula, X and Y can vary, but typically X is from about 100 to about 500, more typically from about 300 to about 400, and Y typically is from about 5 to about 100, more typically from about 10 to about 50.

Many polymeric hydrazides produced prior to the present invention applications were relatively large polymers, and had limited solubility, on the order of about 5 milligram/milliliter or less. Certain embodiments of the present invention are primarily concerned with polyacrylamide hydrazides having a substantially increased aqueous solubility of greater than about 5 milligrams/milliliter up to aqueous saturation, typically greater than about 10 milligrams/milliliter up to at least about 500 milligrams/milliliter, and preferably at least 100 milligrams/milliliter, and more preferably at least about 250 milligrams/milliliter, and even more preferably at least about 300 milligrams/milliliter.

Another important feature is the pKa of the hydrazide functional group, which is around 4. If the pH is about 5 for reactions that may be run using the polymeric hydrazide, then the hydrazide nitrogen is not protonated, and therefore capable of acting as a nucleophile. And at that pH value, the hydrazide acts as a super-nucleophile. For certain disclosed embodiments, functional groups associated with the polymeric carrier act as nucleophiles to couple with carbonyl compounds produced by oxidizing carbohydrate associated with the Fc portion of an antibody. The nucleophilic hydrazide is a good functional group for this reaction. Conversely, amines have a pKa of greater than 9, and typically greater than 10, and hence at a pH of about 5 the amine functional group is completely protonated, and hence not nucleophilic. The hydrazide may be reacted with a carbonyl compound, e.g., an aldehyde. The reaction of the hydrazide with the aldehydes can be acid catalyzed. This difference allows chemoselective reactions. For example, biological amines that may be present in a sample are fully protonated at a pH of about 5 or less, and hence are not nucleophilic, whereas the hydrazides, hydrazines, hydrazide derivatives, hydrazine derivatives, etc. of the present invention are not protonated, and hence available for reaction chemoselectively.

D. Haptens

One of the primary uses of disclosed embodiments is a polymeric carrier for haptens. Haptens are small molecules that can elicit an immune response, but typically only when coupled to a large carrier, such as a protein. Any hapten now known or hereafter discovered likely can be used with the present invention. Known exemplary haptens include dinitrophenol, biotin, digoxigenin, flourescein, rhodamine, bromodeoxyuridine, and mouse immunoglobulin.

Ventana Medical Systems, Inc. also is the assignee of U.S. patent application No. 60/856,133, entitled Haptens, Hapten Conjugates, Compositions Thereof and Method for Their Preparation and Use, which was filed Nov. 1, 2006, and corresponding utility application Ser. No. 11/982,627, which are incorporated herein by reference. These applications disclose several new classes of haptens, and particular species thereof, that are useful for practicing embodiments of the present invention. These haptens include pyrazoles, particularly nitropyrazoles; nitrophenyl compounds; benzofurazans; triterpenes; ureas and thioureas, particularly phenyl ureas, and even more particularly phenyl thioureas; rotenone and rotenone derivatives, also referred to herein as rotenoids; oxazole and thiazoles, particularly oxazole and thiazole sulfonamides; coumarin and coumarin derivatives; cyclolignans, exemplified by Podophyllotoxin and Podophyllotoxin derivatives; and combinations thereof.

For the general formulas provided below, if no substituent is indicated, a person of ordinary skill in the art will appreciate that the substituent is hydrogen. A bond that is not connected to an atom, but is shown, for example, extending to the interior of a ring system, indicates that the position of such substituent is variable. A curved line drawn through a bond indicates that some additional structure is bonded to that position, typically a linker or the functional group or moiety used to couple the hapten to a carrier. Moreover, if no stereochemistry is indicated for compounds having one or more chiral centers, all enantiomers and diasteromers are included. Similarly, for a recitation of aliphatic or alkyl groups, all structural isomers thereof also are included.

1. Azoles

A first general class of haptens of the present invention is azoles, typically oxazoles and pyrazoles, more typically nitro oxazoles and nitro pyrazoles, having the following general chemical formula.

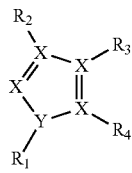

With reference to this general formula, n is 0-2, most typically 0 or 1. $R_1$-$R_4$ can be any organic group that does not interfere with, and potentially facilitates, the function as a hapten. More specifically, $R_1$-$R_4$ independently are selected from: hydrogen, acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, cyano (—CN), ester, ether, exomethylene, halogen, heteroaryl, heterocyclic, hydroxyl, hydroxylamine, oxime (HO—N=), keto, such as aliphatic ketones, nitro, sulfhydryl, sulfonyl, sulfoxide, and combinations thereof. Two or more of these $R_1$-$R_4$ substituents also may be atoms, typically carbon atoms, in a ring system bonded or fused to the compounds having the illustrated general formula. At least one of the $R_1$-$R_4$ substituents is bonded to a linker or is a functional group suitable for coupling to a linker or a carrier molecule. $R_1$-$R_4$ most typically are aliphatic, hydrogen or nitro groups, even more typically alkyl, hydrogen or nitro, and still even more typically lower (10 or fewer carbon atoms) alkyl, hydrogen, nitro, or combinations thereof. The number of nitro groups can vary, but most typically there are 1 or 2 nitro groups. X independently is nitrogen or carbon. Y is oxygen, sulfur or nitrogen. If Y is oxygen or sulfur, then there is no $R_1$ group, and n=0. If Y is nitrogen, then there is at least one $R_1$ group.

A person of ordinary skill in the art will appreciate that, for compounds having 2 or more W groups, the relative positions thereof is variable. For example, a diazole could have nitrogen atoms at the 1 and 2 positions, or the 1 and 3 positions. Moreover, more than two heteroatoms also are possible, such as with triazines.

At least one of $R_1$-$R_4$ for these azole compounds is bonded to some other group or is a variable functional group. For example, the illustrated compounds can be coupled either directly to a carrier or to a linker at any of the suitable positions about the azole ring.

Working embodiments typically were mono- or di-nitropyrazole derivatives, such that at least one of $R_1$-$R_4$ is a nitro group, and perhaps two of $R_1$-$R_4$ are nitro groups, with the remaining $R_1$-$R_4$ being used to couple the hapten to a linker or a carrier.

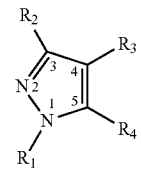

One particular compound had the following structure.

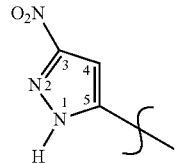

2. Nitroaryl

A second general class of haptens of the present invention are nitroaryl compounds. Exemplary nitroaryl compounds include, without limitation, nitrophenyl, nitrobiphenyl, nitrotriphenyl, etc., and any and all heteroaryl counterparts, having the following general chemical formula.

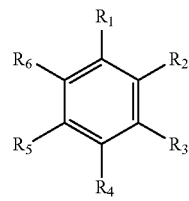

With reference to this general formula, such compounds have at least one, and optionally plural, nitro groups. Thus, at least one of $R_1$-$R_6$ is nitro. If more than one of $R_1$-$R_6$ is nitro, all combinations of relative ring positions of plural nitro substituents, or nitro substituents relative to other ring substituents, are included within this class of disclosed haptens. Dinitroaryl compounds are most typical. A person of ordinary skill in the art will appreciate that as the number of nitro groups increases, the number of remaining ring substituents in the general formula decreases. These substituents independently are selected from: hydrogen, acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer carbon atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, ether, halogen, heteroaryl, hydroxyl, hydroxlyamine, oxime (HO—N=), keto, such as aliphatic ketones, nitro, sulfhydryl, sulfonyl, sulfoxide, exomethylene, and combinations thereof. At least one of the $R_1$-$R_6$ substituents is bonded to a linker or is a functional group suitable for coupling to a linker or a carrier molecule.

Two or more of the $R_1$-$R_6$ substituents also may be atoms, typically carbon atoms, in a ring system, such as napthalene (shown below) or anthracene type derivatives. Ring systems other than 6-membered ring systems can be formed, such as fused 6-5 ring systems.

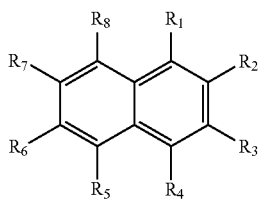

Again, at least on of the ring positions occupied by $R_1$-$R_8$ is bonded to a linker or is a variable functional group suitable for coupling, such as by covalent bonding, to a carrier molecule. For example, nitroaryl compounds of the present invention can include a functional group for coupling to a carrier, or to a linker, at various optional ring locations.

Working embodiments are exemplified by nitrophenyl compounds. Solely by way of example, mononitroaryl compounds are exemplified by nitrocinnamide compounds. One embodiment of a nitrocinnamide-based compound is exemplified by 4,5-dimethoxy-2-nitrocinnamide, shown below.

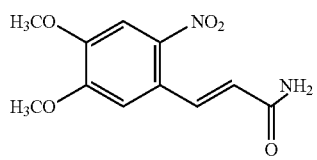 [SMILES: COc1cc(/C=C/C(N)=O)c([N+](=O)[O-])cc1OC]

The nitrophenyl class of compounds also is represented by dinitrophenyl compounds. At least one of the remaining carbon atoms of the ring positions not having a nitro group is bonded to a functional group, to a linker, or directly to a carrier. Any and all combinations of relative positions of these groups are included within the class of disclosed haptens.

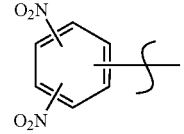

Working embodiments are more particularly exemplified by 2,4-dinitrophenyl compounds coupled to a linker, as illustrated below.

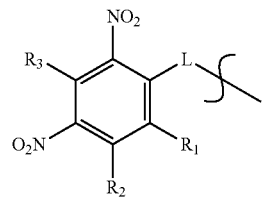

$R_1$-$R_3$ are as stated above. "L" is a linker, as discussed in more detail below.

3. Benzofurazans

Benzofurazans and derivatives thereof are another class of haptens within the scope of the present invention. A general formula for the benzofurazan-type compounds is provided below.

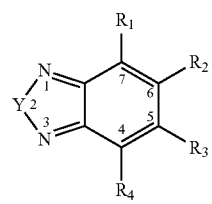

$R_1$-$R_4$ substituents independently are selected from: hydrogen, acyl, aldehydes, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, exomethylene, and combinations thereof. Two or more of these $R_1$-$R_4$ substituents also may be atoms, typically carbon atoms, in a ring system bonded or fused to the compounds having the illustrated general formula. At least one of the $R_1$-$R_4$ substituents is bonded to a linker or directly to a carrier. Y is a carbon atom having $R_5$ and $R_6$ substituents, where $R_5$ and $R_6$ are as stated for $R_1$-$R_4$, oxygen or sulfur, typically oxygen.

Compounds where Y is oxygen are more particularly exemplified by compounds having the following structure, where $R_1$-$R_4$ are as stated above, and most typically are independently hydrogen and lower alkyl.

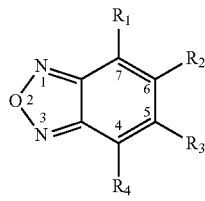

One working embodiment of a compound according to this class of haptens had the following chemical structure.

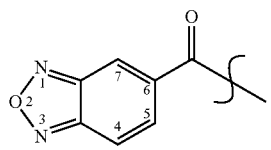

4. Triterpenes

Triterpenes are another class of haptens within the scope of the present invention. The basic ring structure common to the cyclic triterpenes has four six-membered fused rings, A-D, as indicated below.

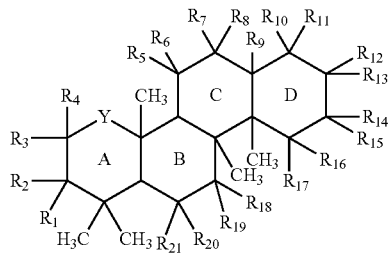

A number of publications discuss naturally occurring, semi-synthetic and synthetic triterpene species within the genus of triterpenes useful for practicing the present invention, including: J. C. Connolly and R. A. Hill, Triterpenoids, Nat. Prod. Rep., 19, 494-513 (2002); Baglin et al., A Review of Natural and Modified Beculinic, Ursolic and Echinocystic Acid Derivatives as Potential Antitumor and Anti-HIV Agents, Mini Reviews in Medicinal Chemistry, 3, 525-539; W. N. and M. C. Setzer, Plant-Derived Triterpenoids as Potential Antineoplastic Agents, Mini Reviews in Medicinal Chemistry, 3, 540-556 (2003); and Baltina, Chemical Modification of Glycyrrhizic Acid as a Route to New Bioactive Compounds for Medicine, Current Medicinal Chemistry, 10, 155-171 92003); each of which is incorporated herein by reference. Based on the present disclosure and working embodiments thereof, as well as disclosures provided by these prior publications, and with reference to this first general formula, $R_1$-$R_{21}$ independently are selected from: hydrogen, acyl, aldehydes, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxy-imine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, exomethylene, and combinations thereof. Two or more of these $R_1$-$R_{21}$ substituents also may be atoms, typically carbon atoms, in a ring system bonded or fused to the compounds having the illustrated general formula. At least one of the $R_1$-$R_{21}$ substituents is bonded to a linker or is a functional group suitable for coupling to a linker or a carrier molecule. Y is a bond, thereby defining a 5-membered ring, or is a carbon atom bearing $R_{22}$ and $R_{23}$ substituents, where these R groups are as stated above.

Disclosed embodiments of triterpenes exemplifying this class of haptens also may atoms, typically carbon atoms, in the ring. For example, the E ring might be a 6-membered ring, as indicated by the following general formula, where $R_1$-$R_{31}$ are as stated above for $R_1$-$R_{21}$.

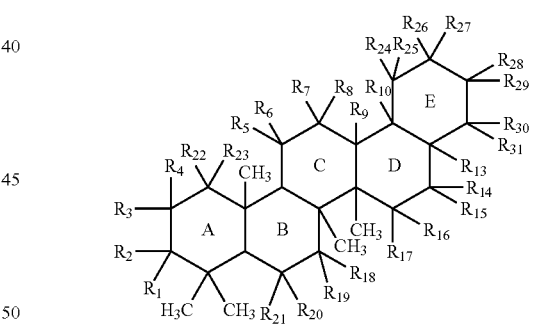

The following general formulae indicates that the $R_{13}$ substituent may be an acyl group bearing an $R_{33}$ substituent selected from hydrogen, hydroxyl, ester, i.e. —$OR_{34}$ where $R_{34}$ is aliphatic, typically alkyl or substituted alkyl, and even more typically lower alkyl, amido, including primary amide (—$NH_2$), secondary amide (—$NHR_{35}$) and tertiary amide (—$NR_{35}R_{36}$), where $R_{35}$ and $R_{36}$ are aliphatic, typically lower aliphatic, more typically alkyl, substituted alkyl, and even more typically lower alkyl or substituted lower alkyl. This general formula also indicates that the $R_1$ substituent often is an $OR_{32}$ substituent, where $R_{32}$ is hydrogen or aliphatic, more typically alkyl or substituted alkyl, and even more typically lower alkyl. The remaining R groups are as stated above with reference to the first general formula.

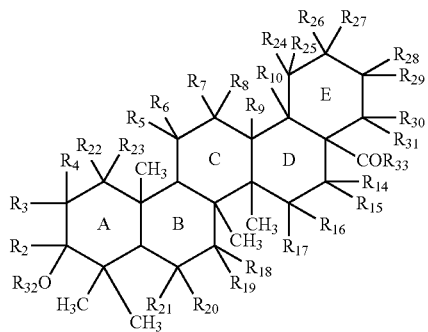

The E ring also may be a 5 membered ring, as indicated by the formula below where the $R_1$-$R_{29}$ groups are as stated above for $R_1$-$R_{21}$.

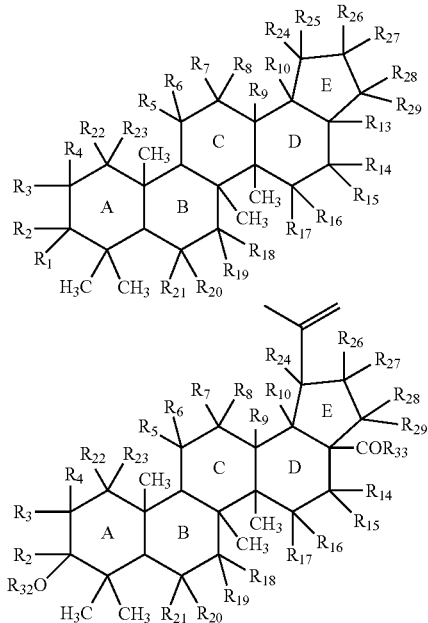

With reference to these general formulae, the $R_1$-$R_{29}$ groups are as stated above for $R_1$-$R_{21}$.

As with exemplary compounds where the E ring is a 6-membered ring, compounds where the E ring is a 5-membered ring also can include substituents at $R_1$ and $R_{13}$ as discussed above. Specifically, this general formulae indicates that the $R_{13}$ substituent may be an acyl group bearing an $R_{33}$ substituent selected from hydrogen, hydroxyl, ester, i.e. —$OR_{34}$ where $R_{34}$ is aliphatic, typically alkyl or substituted alkyl, and even more typically lower alkyl, amido, including primary amide (—$NH_2$), secondary amide (—$NHR_{35}$) and tertiary amide (—$NR_{35}R_{36}$), where $R_{35}$ and $R_{36}$ are aliphatic, typically lower aliphatic, more typically alkyl, substituted alkyl, and even more typically lower alkyl or substituted lower alkyl. This general formula also indicates that the $R_1$ substituent often is an $OR_{32}$ substituent, where $R_{32}$ is hydrogen or aliphatic, more typically alkyl or substituted alkyl, and even more typically lower alkyl.

Exemplary compounds also include 5-membered rings as both the A and the E ring. General formulae for such exemplary compounds are provided below, where the $R_1$-$R_{29}$ substituents are as stated above.

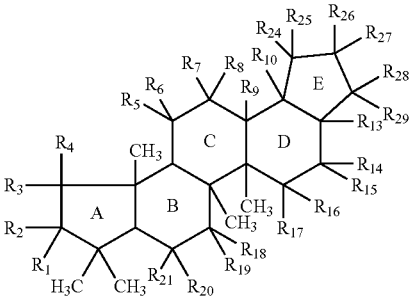

Again, the $R_1$ and $R_{13}$ substituents can be oxygen-based functional groups. The $R_{13}$ substituent may be an acyl group bearing an $R_{33}$ substituent selected from hydrogen, hydroxyl, ester, i.e. —$OR_{34}$ where $R_{34}$ is aliphatic, typically alkyl or substituted alkyl, and even more typically lower alkyl, amido, including primary amide (—$NH_2$), secondary amide (—$NHR_{35}$) and tertiary amide (—$NR_{35}R_{36}$), where $R_{35}$ and $R_{36}$ are aliphatic, typically lower aliphatic, more typically alkyl, substituted alkyl, and even more typically lower alkyl or substituted lower alkyl. This general formula also indicates that the $R_1$ substituent often is an $OR_{32}$ substituent, where $R_{32}$ is hydrogen or aliphatic, more typically alkyl or substituted alkyl, and even more typically lower alkyl.

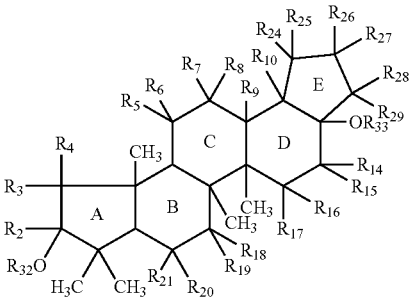

Exemplary triterpenes of the present invention also may include one or more sites of unsaturation in one or more of the A-E rings. Exemplary compounds often have at least one site of unsaturation in the C ring, such as the double bond in the C ring as indicated below.

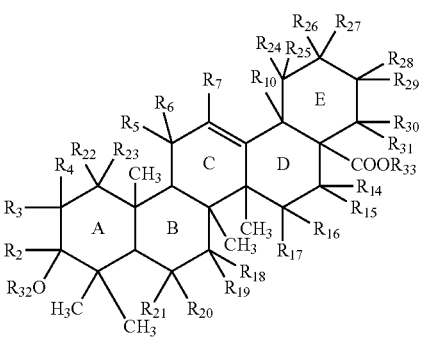

The site of unsaturation may be an alpha, beta unsaturated ketone, such as illustrated below for the C ring.

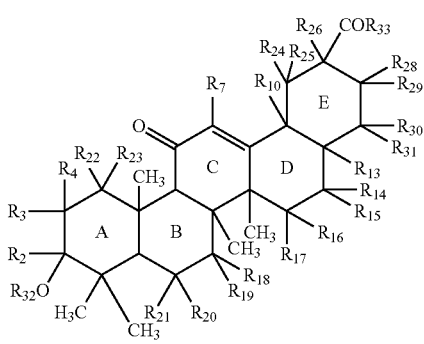

The triterpenes also have a number of stereogenic carbon atoms. A person of ordinary skill in the art will appreciate that particular enantiomers are most likely to occur naturally. While the naturally occurring enantiomer may be most available, and/or effective, for practicing disclosed embodiments, all other possible stereoisomers are within the scope of the present invention. Moreover, other naturally occurring triterpenes, or synthetic derivatives thereof, or fully synthetic compounds, may have (1) different stereochemistry, (2) different substituents, and further may be substituted at positions that are not substituted in the naturally occurring compounds. The general formulae provided above do not indicate stereochemistry at the chiral centers. This is to signify that both enantiomers at each chiral center, and all diastereomeric isomer combinations thereof, are within the scope of the present invention.

Particular working embodiments of the present invention are exemplified by the following general formula, in which the substituents are as stated above.

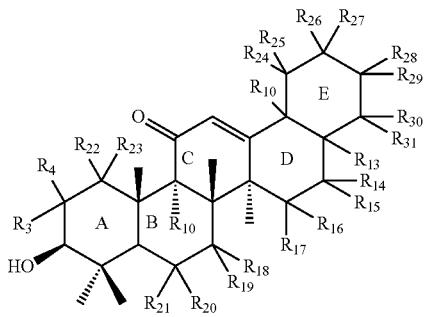

The stereochemistry and substituents for a naturally occurring triterpene useful as a hapten for practicing the present invention are shown below.

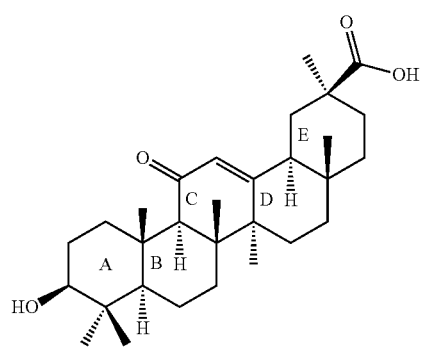

The hydroxyl group in the A ring typically is oxidized to a carbonyl functional group in working embodiments. As a result, the carbon atom bearing the carbonyl group is no longer a chiral center.

5. Ureas and Thioureas

Ureas and thioureas, particularly aryl and heteroaryl ureas and thioureas, are another class of haptens within the scope of the present invention. A general formula for urea-based haptens of the present invention is provided below.

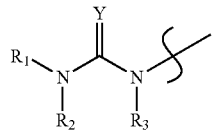

With reference to this general formula, $R_1$-$R_3$ are independently hydrogen, aliphatic, substituted aliphatic, typically alkyl, substituted alkyl, and even more typically lower alkyl and substituted lower alkyl, cyclic, heterocyclic, aryl and heteroaryl. More specifically, $R_1$ typically is aryl or aliphatic, often having at least one site of unsaturation to facilitate chromophoric detection. $R_2$ and $R_3$ most typically are independently hydrogen and lower alkyl. Y is oxygen (urea derivatives) or sulfur (thioureas).

Aryl derivatives typically have the following formula.

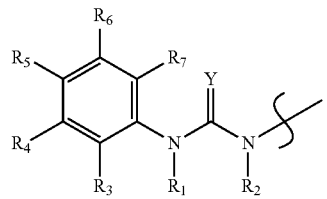

$R_1$-$R_7$ independently are selected from: hydrogen, acyl, aldehydes, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, exomethylene, and combinations thereof. At least one of the $R_3$-$R_7$ substituents also is bonded to a linker or to a carrier molecule. Two or more of these $R_3$-$R_7$ substituents available for such bonding also may be atoms, typically carbon atoms, in a ring system bonded or fused to the compounds having the illustrated general formula.

Additional rings also can be present, as indicated by the exemplary structures provided below. The R groups are as stated above for $R_1$-$R_7$ and Y is oxygen or sulfur.

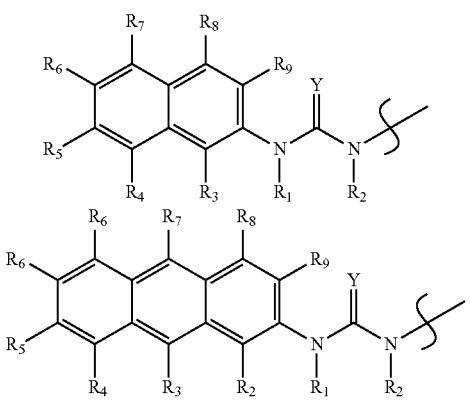

A particular subclass of thioureas is represented below.

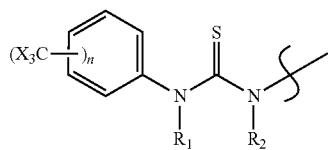

With reference to this general formula, n is 1 to 5, typically 1-2, $R_1$ and $R_2$ are independently hydrogen or lower alkyl, and X independently is a halide or combinations of different halides.

One example of a working embodiment of a phenyl thiourea is provided below.

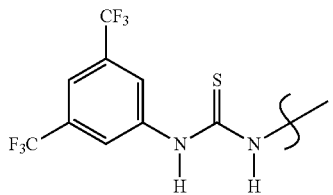 [SMILES: CCNC(=S)Nc1cc(C(F)(F)F)cc(C(F)(F)F)c1]

The trifluoromethyl groups are shown in the 3 and 5 positions relative to the thiourea moiety. A person of ordinary skill in the art will appreciate that compounds having all relative positions for disubstituted compounds, such as 2,4- and compounds having more than two trihaloalkyl substituents, at all possible relative positions of such plural trihaloalkyl substituents, also are within the scope of the present invention. A particular example of a rhodamine thiourea hapten has the following formula.

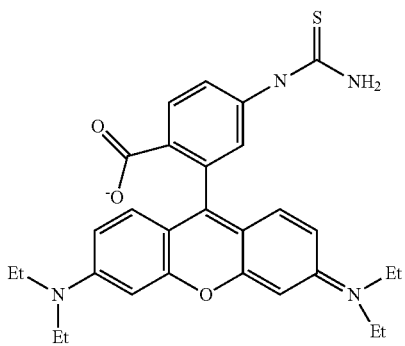

6. Rotenones

Rotenone and rotenone-based haptens, collectively referred to as rotenoids, provide another class of haptens within the scope of the present invention. A first general formula for rotenone, and rotenone-based haptens, is provided below.

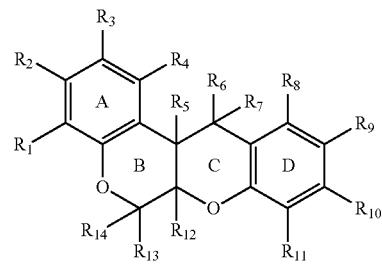

A number of publications discuss naturally occurring, semi-synthetic and synthetic rotenoids that are useful for describing the genus of rotenoids useful for practicing the present invention, including: Leslie Crombie and Donald Whiting, Biosynthesis in the Rotenoids Group of Natural Products Application of Isotope Methodology, Phytochemistry, 49, 1479-1507 (1998); and Nianbai Fang, and John Casida, Cube Resin Insecticide: Identification and Biological Activity of 29 Rotenoid Constituents; each of which is incorporated herein by reference. Based on the present disclosure and working embodiments, as well as disclosures provided by these prior publications, and with reference to this first general formula, $R_1$-$R_{14}$ independently are hydrogen, aldehyde, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto) amino, amino acid, amido, cyano (—CN), halogen, hydroxyl, hydroxylamine, oxime (HO—N=), oxime ether (e.g., methoxyimine, $CH_3$—O—N=) alkyl hydroxyl, particularly lower alkyl hydroxyl, carbonyl, keto, such as aliphatic ketones, nitro, sulfhydryl, sulfonyl, sulfoxide, carboxyl, carboxylate (and salts thereof, such as Group I metal or ammonium ion carboxylates) ester, alkyl ester, acyl, exomethylene, ether, cyclic, heterocyclic, aryl, alkyl aryl, such as benzyl, heteroaryl, polysaccharides, carbohydrate, monosaccharides, such as glucose and fructose, disaccharides, such as sucrose and lactose, oligosaccharides and polysaccharides, and combinations thereof. Two or more of these $R_1$-$R_{14}$ substituents also may be atoms, typically carbon atoms, in a ring system bonded or fused to the compounds having the illustrated general formula. At least one of the $R_1$-$R_{14}$ substituents also is bonded to a linker or to a carrier molecule.

While $R_6$ and $R_7$ can be as stated above, such substituents more typically independently are hydrogen, $OR_{15}$, where $R_{15}$ is hydrogen, aliphatic, substituted aliphatic, typically alkyl, substituted alkyl, and even more typically lower alkyl and substituted lower alkyl, such as lower alkyl halides, cyclic, heterocyclic, aryl and heteroaryl, —$NR_{21}$, where $R_{21}$ is hydrogen, aliphatic, substituted aliphatic, typically alkyl, substituted alkyl, and even more typically lower alkyl and substituted lower alkyl, such as lower alkyl halides, cyclic, heterocyclic, aryl and heteroaryl, or N-L-RG, where L is a linker or a reactive group, such as an amine, as discussed in more detail herein.

$R_6$ and $R_7$ also can form a double bond, such as a double bond to an oxygen to form a carbonyl. If $R_6$ and/or $R_7$ are not -L-RG, then at least one of the R substituents is bonded to a linker or to a carrier molecule.

The B ring also can include at least one additional site of unsaturation. For example, $R_5$ and $R_{12}$ can form a double bond.

$R_{10}$ and $R_{11}$ can be joined in a 5- or 6-membered ring. For example, $R_{10}$ and $R_{11}$ may define a pyran or furan ring, and more particularly is a substituted and/or unsaturated pyran or furan ring.

Certain exemplary rotenone-based haptens of the present invention also typically satisfy the following second general formula.

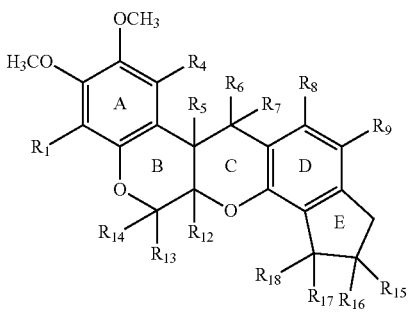

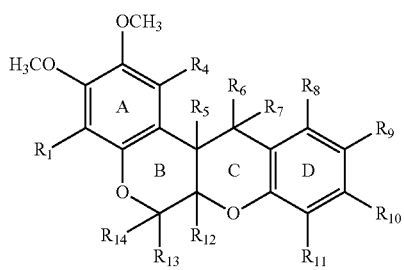

With reference to this second general formula, the R substituents are as stated above. If $R_6$ or $R_7$ is not -L-RG, then at least one of the remaining R groups is bonded to a linker or to a carrier.

$R_{10}$ and $R_{11}$ can be joined in a 5- or 6-membered ring, such as a pyran or furan, and more particularly a substituted and/or unsaturated pyran or furan ring. Thus, a third general formula useful for describing certain rotenone-based haptens of the present invention is provided below, where the R substituents are as stated above.

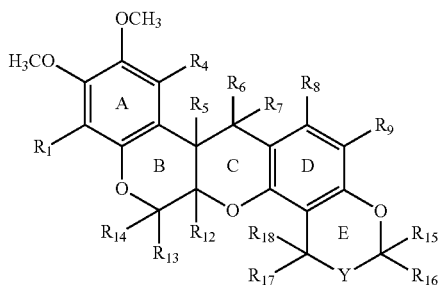

Y is a bond, thereby defining a 5-membered ring, or is a carbon atom in a 6-membered ring bearing $R_{19}$ and $R_{20}$ substituents, as shown below, where the R substituents are as stated above.

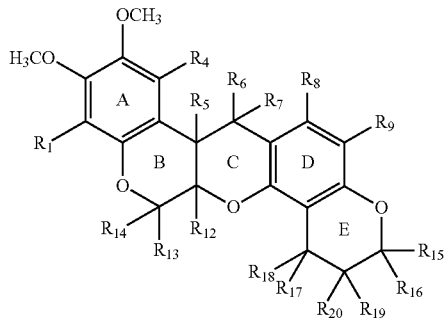

$R_5$ and $R_{12}$ at the ring juncture are shown without indicating particular stereochemistry. The naturally occurring compound has a cis-ring juncture, but racemic mixtures also are useful for practicing the present invention. Also, the trans stereoisomer quickly equilibrates to form the racemic mixture.

Working embodiments of compounds within this class more typically satisfy the following third general formula.

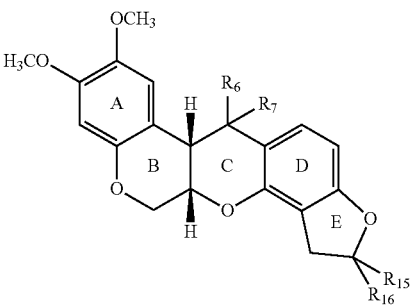

With reference to this general formula, $R_6$ and $R_7$ are hydrogen, alkyl, or define a double bond, such as to oxygen to form a carbonyl. $R_{15}$ and $R_{16}$ independently are hydrogen and aliphatic, typically lower aliphatic, such as alkenyl, one example of which is isoprene, as shown below.

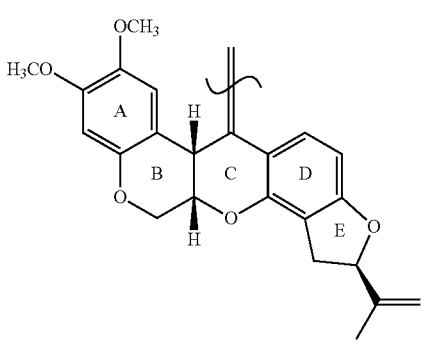

Again, a particular enantiomer is shown in the above formula, but a person of ordinary skill in the art will appreciate that the scope of the present invention is not limited to the particular enantiomer shown. Instead, all stereoisomers that act as haptens also are within the scope of the disclosure. All substitutions discussed above for this class of compounds applies to this particular compound. Other substitutions also are readily apparent to a person of ordinary skill in the art. For example, the methoxy groups on the A ring can be any alkoxy compound, particular lower alkoxy groups. The isoprene unit also provides an olefin that can be synthetically modified, perhaps to provide an alternative position, or at least a second position, for coupling the hapten to a linker or a carrier molecule. For example, the olefin could be converted to an alcohol by hydroboration. It also could be converted to a halide or an epoxide either for use as a hapten or as intermediates useful for further transformation.

A fourth general formula for describing rotenone-based haptens of the present invention is particularly directed to rotenone isoxazolines, as provided below.

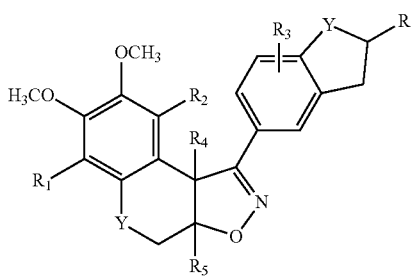

R-$R_5$ independently are hydrogen, aldehyde, alkoxy, aliphatic, particularly lower aliphatic, including all branched chain isomers, such as isoprene, and all stereoisomers, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto) amino, amino acid, amido, cyano (—CN), halogen, hydroxyl, hydroxylamine, oxime (HO—N=), oxime ether (e.g., methoxyimine, $CH_3$—O—N=) alkyl hydroxyl, particularly lower alkyl hydroxyl, carbonyl, keto, such as aliphatic ketones, nitro, sulfhydryl, sulfonyl, sulfoxide, carboxyl, carboxylate (and salts thereof, such as Group I metal or ammonium ion carboxylates) ester, alkyl ester, acyl, exomethylene, ether, cyclic, heterocyclic, aryl, alkyl aryl, such as benzyl, heteroaryl, polysaccharides, carbohydrate, monosaccharides, such as glucose and fructose, disaccharides, such as sucrose and lactose, oligosaccharides and polysaccharides, and combinations thereof. At least one of the R-$R_5$ substituents also is bonded to a linker or to a carrier molecule. Y is oxygen, nitrogen, or sulfur.

A particular working embodiment of a rotenone-based hapten satisfying this fourth general formula is provided below.

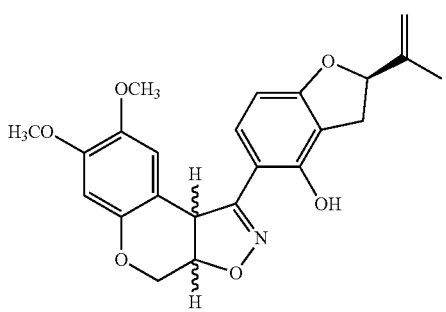

7. Oxazoles and Thiazoles

Oxazole and thiazole sulfonamides provide another class of haptens within the scope of the present invention. A general formula for oxazole and thiazole sulfonamides is provided below.

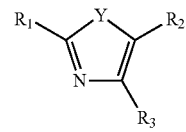

With reference to this first general formula $R_1$-$R_3$ independently are selected from: hydrogen, acyl, aldehydes, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, exomethylene, and combinations thereof. Two or more of these $R_1$-$R_3$ substituents also may be atoms, typically carbon atoms, in a ring system bonded or fused to the compounds having the illustrated general formula. At least one of the $R_1$-$R_3$ substituents is bonded to a linker or is a functional group suitable for coupling to a linker or a carrier molecule. Y is oxygen or sulfur, typically sulfur.

For certain exemplary working embodiments, $R_1$ has been amido, such as the amide derivatives shown below. $R_2$ provides a position for coupling to a linker or to a carrier molecule, although the positions indicated by $R_1$ and $R_2$ also provide alternative or additional positions for coupling to a linker and/or carrier molecule. $R_2$, for certain working embodiments, has been —$SO_2$, and has been used to couple linkers by forming a sulfonamide. Thus, a second general formula for working embodiments of haptens exemplifying this class of haptens is indicated below, where the $R_3$-$R_6$ substituents and Y are as stated above.

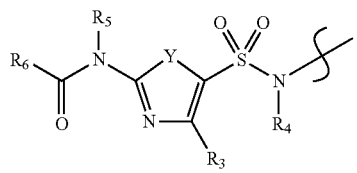

For certain working embodiments $R_6$ has been alkyl, particularly lower alkyl, such as methyl, and Y has been sulfur.

One working embodiment of a compound according to this class of haptens had the following chemical structure.

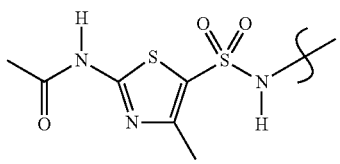 [SMILES: CCNS(=O)(=O)c1sc(NC(C)=O)nc1C]

The thiazole or oxazole might also be part of a larger ring system. For example, the 5-membered oxazole or thiazole might be coupled to at least one additional ring, such as a phenyl ring, as indicated below.

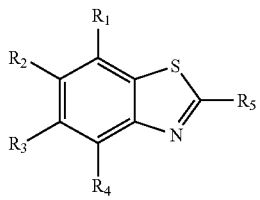

While the $R_1$-$R_5$ groups generally can be as stated above, such compounds also provide a position for coupling to a linker and/or to a carrier molecule, such as a $R_5$. One possible sulfonamide derivative is provided below.

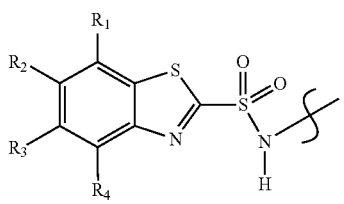

8. Coumarins

Coumarin and coumarin derivatives provide another class of haptens within the scope of the present invention. A general formula for coumarin and coumarin derivatives is provided below.

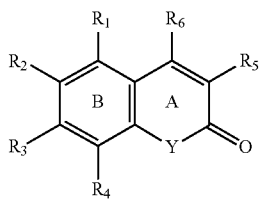

With reference to this general formula, $R_1$-$R_6$ independently are selected from: hydrogen, acyl, aldehydes, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, exomethylene, and combinations thereof. At least one of the $R_1$-$R_6$ substituents also typically is bonded to a linker or a carrier molecule. Certain working embodiments have used the position indicated as having an $R_5$ substituent for coupling to a linker or carrier molecule. The 4 position can be important if fluorescence is used to detect these compounds. Substituents other than hydrogen at the 4 position are believed to quench fluorescence, although such derivatives still may be chromophores. Y is oxygen, nitrogen or sulfur. Two or more of the $R_1$-$R_6$ substituents available for forming such compounds also may be atoms, typically carbon atoms, in a ring system bonded or fused to the compounds having the illustrated general formula. Exemplary embodiments of these types of compounds are provided below.

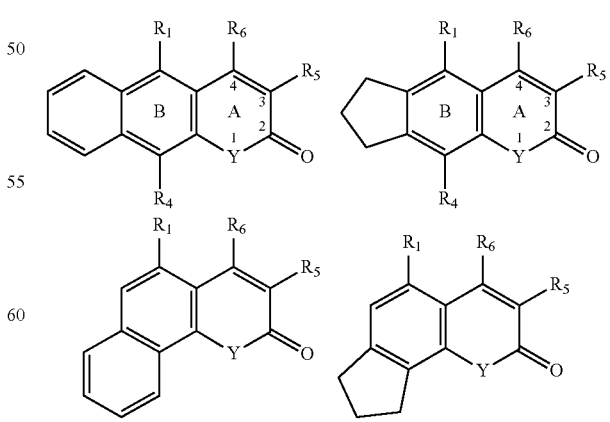

A person of ordinary skill in the art will appreciate that the rings also could be heterocyclic and/or heteroaryl.

Working embodiments typically were fused A-D ring systems having at least one carrier molecule coupling position, with one possible coupling position being indicated below.

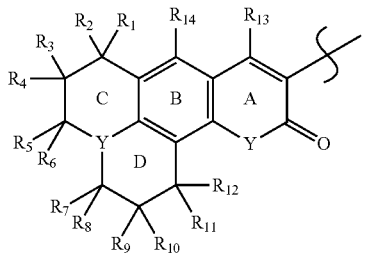

With reference to this general formula, the R and Y variable groups are as stated above. Most typically, $R_1$-$R_{14}$ independently are hydrogen or lower alkyl. Particular embodiments of coumarin-based haptens include 2,3,6,7-tetrahydro-11-oxo-1H, 5H, 11H-[1]benzopyrano[6,7,8-ij]quinolizine-10-carboxylic acid

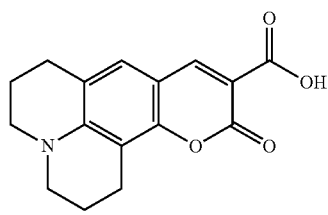

and diethyl coumarin

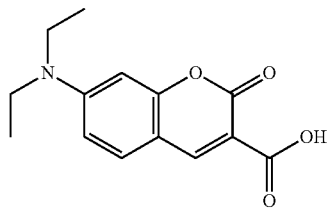 [SMILES: CCN(CC)c1ccc2cc(C(=O)O)c(=O)oc2c1]

9. Cyclolignans

Lignin-based compounds, particularly cyclolignans, such as Podophyllotoxin and derivatives thereof, provide another class of haptens within the scope of the present invention. A first general formula for these cyclolignin-based derivatives is provided below.

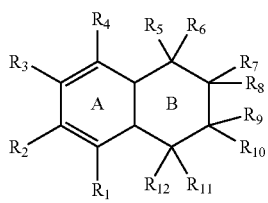

A number of publications discuss naturally occurring, semi-synthetic and synthetic cyclolignans that are useful for describing the genus of cyclolignans useful for practicing the present invention, including: Stephanie Desbene and Sylviane Giorgi-Renault, Drugs that Inhibit Tubulin Polymerization The Particular Case of Podophyllotoxin and Analogues, Curr. Med. Chem.—Anti-Cancer Agents, 2, 71-90 (2002); M. Gordaliza et al., Podophyllotoxin: Distribution, Sources, Applications and New Cytotoxic Derivatives, Toxicon, 44, 441-459 (2004); Phillipe Meresse et al., Etoposide: Discovery and Medicinal Chemistry, Current Medicinal Chemistry, 11, 2443-2466 (2004); M. Pujol et al., Synthesis and Biological Activity of New Class of Dioxygenated Anticancer Agents, Curr. Med. Chem.—Anti-Cancer Agents, 5, 215-237 (2005); and Youngjae You, Podophyllotoxin Derivatives: Current Synthetic Approaches for New Anticancer Agents, Current Pharmaceutical Design, 11, 1695-1717 (2005); each of which is incorporated herein by reference. Based on the present disclosure and working embodiments, as well as disclosures provided by these prior publications, and with reference to this first general formula, $R_1$-$R_{12}$ typically are selected from hydrogen, aldehyde, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto) amino, amino acid, amido, cyano (—CN), halogen, hydroxyl, hydroxylamine, oxime, oxime ether (e.g., methoxyimine, $CH_3$—O—N=) alkyl hydroxyl, particularly lower alkyl hydroxyl, carbonyl, keto, such as aliphatic ketones, nitro, sulfhydryl, sulfonyl, sulfoxide, carboxyl, carboxylate (and salts thereof, such as Group I metal or ammonium ion carboxylates) ester, alkyl ester, acyl, exomethylene, ether, cyclic, heterocyclic, aryl, alkyl aryl, such as benzyl, heteroaryl, polysaccharides, carbohydrate, monosaccharides, such as glucose and fructose, disaccharides, such as sucrose and lactose, oligosaccharides and polysaccharides, and combinations thereof. At least one of $R_1$-$R_{12}$ provides a position for coupling the compound to a linker or to a carrier molecule. Furthermore, certain of the R groups may be atoms in a ring system. For example, $R_2$ and $R_3$, as well as two of $R_7$-$R_{10}$, can be joined together in a ring system. At least one of $R_{12}$ and $R_{11}$ also often is an aryl group, such as a benzene ring or a substituted benzene ring.

Certain working embodiments also satisfied the following second general formula, where the R substituents are as stated above.

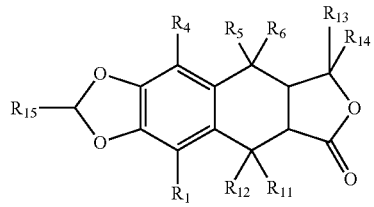

Exemplary compounds where at least one of $R_{11}$ and $R_{12}$ is an aryl group have the following general formula, where the R substituents are as stated above.

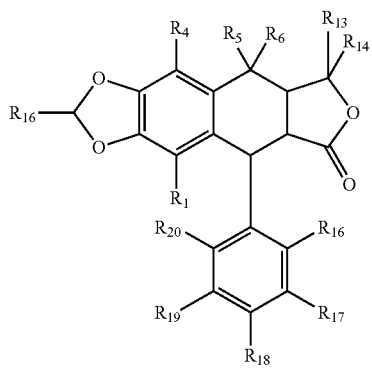

$R_{16}$-$R_{20}$ are generally as stated above, but more typically independently are hydrogen or alkoxy, typically lower alkoxy, such as methoxy, as shown below.

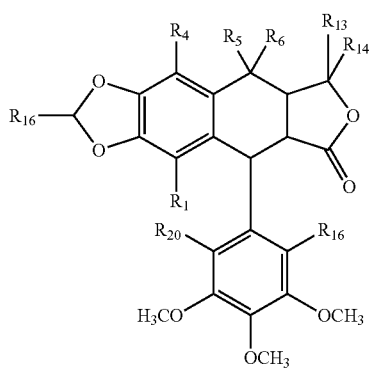

At least one of the R substituents typically is bonded to a linker, is a reactive functional group capable of reacting with a linker, or is -L-RG. For example, $R_5$ often is -L-RG.

$R_5$ and $R_6$ also may form a double bond, such as a double bond to oxygen to form a carbonyl functional group or a double bond to a nitrogen atom to form an imine. Certain exemplary compounds where $R_5$ and $R_6$ form a double bond had the following general formula, where the remaining R substituents are as stated above. Y is selected from nitrogen, oxygen or sulfur. If Y is nitrogen, then the nitrogen atom may further have bonded thereto hydrogen, or some atom, functional group or chemical moiety other than hydrogen. For example, the nitrogen may have an aliphatic substituent, such an alkyl group, an aryl or heteroaryl substituent, or a substituted aryl or heteroaryl substituent, such as alkyl and/or alkoxy substituted aryl or heteroaryl substituent.

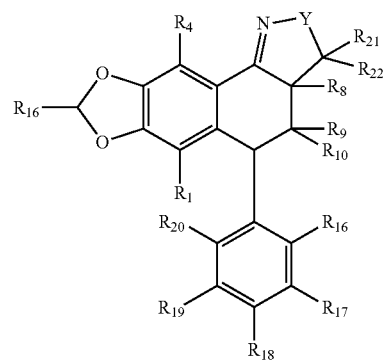

$R_{16}$-$R_{20}$ are independently selected from hydrogen and alkoxy, more typically lower alkoxy, such as methoxy, as indicated below.

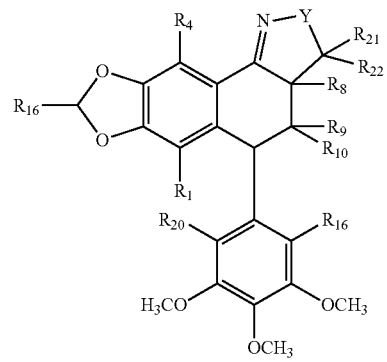

As with all hapten conjugates of the present invention, at least one of the R substituents typically is bonded to a linker, is a reactive functional group capable of reacting with a linker, is -L-RG, or is directly bonded to a carrier. For example, $R_9$ often is -L-RG.

The chemical structure for Podophyllotoxin, a compound exemplifying this cyclolignan class of haptens, is provided below.

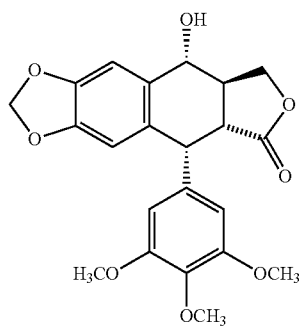 [SMILES: COc1cc([C@@H]2c3cc4c(cc3[C@H](O)[C@H]3COC(=O)[C@H]23)OCO4)cc(OC)c1OC]

Podophyllotoxin, also referred to as podofilox, is a non-alkaloid toxin having a molecular weight of 414.40 and a compositional formula of $C_{22}H_{22}O_8$. Podophyllotoxin is present at concentrations of 0.3 to 1.0% by mass in the rhizome of American Mayapple Podophyllum peltatum. The melting point of Podophyllotoxin is 183.3-184.0° C.

Accordingly, cyclolignans according to the present invention based substantially on the Podophyllotoxin structure have the following general formula, where Y is selected from nitrogen, oxygen or sulfur.

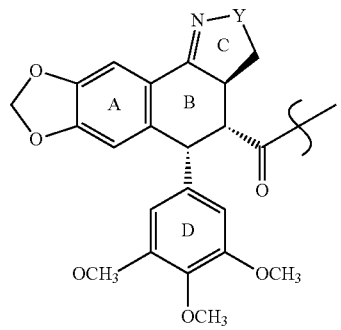

A specific example of a cyclolignan hapten according to the present invention is shown below.

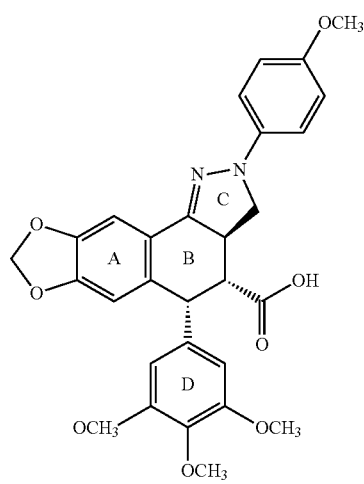

This compound was made starting with Podophyllotoxin. The hydroxyl group of Podophyllotoxin was oxidized to a ketone. The ketone was then reacted with a substituted hydrazine to produce the compound indicated above. The hydrazine reagent can be substituted as desired, including aliphatic and aryl substituents.

10. Heterobiaryl

Another general class of haptens of the present invention is heterobiaryl compounds, typically phenyl quinolines and quinoxalines. Disclosed heterobiaryl compounds have a first general chemical formula as below.

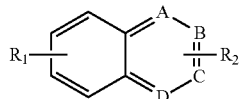

With reference to this general formulae, A-D are selected from carbon, nitrogen, oxygen, and sulfur, and any and all combinations thereof. Most typically A-D are carbon or nitrogen. $R_1$-$R_2$ substituents independently are selected from: hydrogen, acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, alkoxy aryl, such as methoxy and ethoxy, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, exomethylene, and combinations thereof. Two or more of the $R_1$-$R_2$ substituents, most typically plural $R_1$ substituents also may be atoms, typically carbon atoms, in a ring system bonded or fused to the compounds having the illustrated general formula. At least one of the $R_1$-$R_2$ substituents typically is bonded to a linker or directly to a carrier.

Particular embodiments of the heterobiaryl compounds have the following formula.

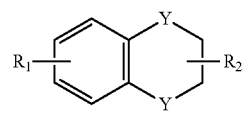

R1 and R2 are as stated above for the first general formula. Y is oxygen, nitrogen or sulfur, typically nitrogen. If Y is nitrogen, then the formula also can include double bonds to the one or more nitrogen atoms.

Compounds having a single heteroatom are exemplified by phenylquinolines, such as follows.

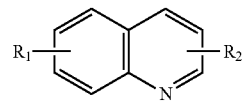

More particular embodiments include aryl substituted haptens, exemplified by the following general formula.

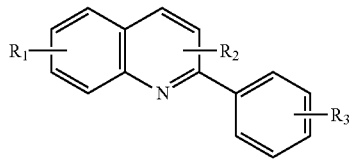

With reference to this general formula, $R_1$-$R_3$ are as indicated above. More typically, $R_1$ is hydrogen, $R_2$ is acyl, and $R_3$ is alkoxy. A particular example, 2-(3,4-dimethoxyphenyl) quinoline-4-carboxylic acid, is provided below.

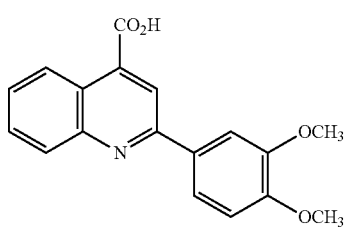

Compounds having two heteroatoms are represented by quinoxalines, as indicated by the general formula below.

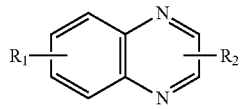

A particular example of biaryl-diheteroatom hapten of the present invention is exemplified by 3-hydroxy-2-quinoxalinecarbamide, below. Again, the $R_1$ and $R_2$ substituents are as stated above with respect to this class of haptens.

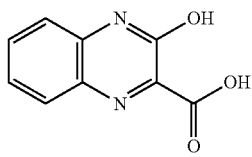 [SMILES: O=C(O)c1nc2ccccc2nc1O]

11. Azoaryl

Another general class of haptens of the present invention is azoaryl compounds, such as azobenzenes, having a first general chemical formula as below.

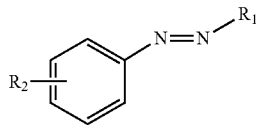

$R_1$-$R_2$ substituents independently are selected from: hydrogen, acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, alkoxy aryl, such as methoxy and ethoxy, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, sulfonyl, exomethylene, and combinations thereof. Two or more $R_2$ substituents also may be atoms, typically carbon atoms, in a ring system bonded or fused to the compounds having the illustrated general formula. For example, 2 $R_2$ substituents may form a fused phenyl ring, or a fused heterocyclic or heteroaryl structure.

Certain disclosed azoaryl compounds have a first amine substituent and a second aryl substituent. These compounds typically have the following formula.

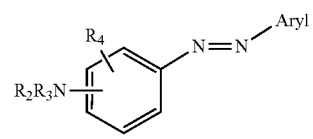

With reference to this general formula, $R_2$-$R_4$ are as stated above with respect to this class of haptens, with particular embodiments having $R_2$-$R_3$ aliphatic, particularly alkyl, more particularly lower alkyl, and $R_4$ hydrogen.

A third general formula for describing azoaryl compounds is provided below.

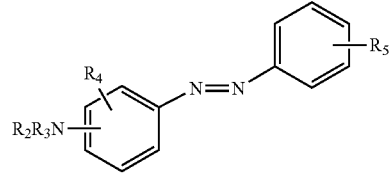

$R_2$-$R_5$ are as stated above for this particular class of haptens. At least one of $R_2$-$R_5$ defines a position for coupling a linker or carrier to the azoaryl hapten to form a conjugate. For example, $R_5$ may be a sulfonyl halide functional group. Sulfonyl halides, such as that shown below, are useful functional groups for coupling linkers to the azoaryl haptens.

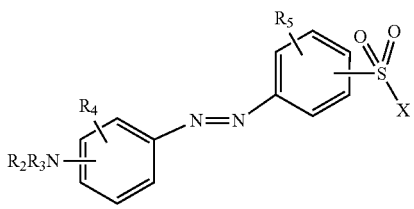

With reference to this formula, $R_2$-$R_5$ are as stated above. X is a halide. A particular embodiment of these azoaryl haptens, 4-(dimethylamino)azobenzene-4'-sulfonyl chloride, has the formula provided below.

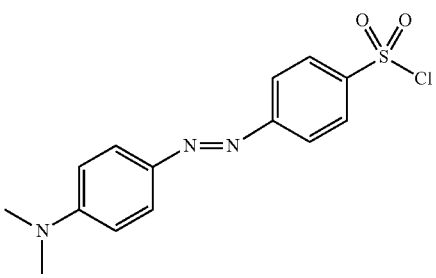 [SMILES: CN(C)c1ccc(/N=N/c2ccc(S(=O)(=O)Cl)cc2)cc1]

12. Benzodiazepines

Another class of haptens according to the present invention is the benzodiazepine haptens, having a first general formula as indicated below.

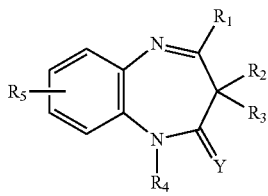

$R_1$-$R_5$ independently are selected from: acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, cyano (—CN), ester, ether, exomethylene, halogen, heteroaryl, heterocyclic, hydrogen, hydroxyl, hydroxylamine, oxime (HO—N=), keto, such as aliphatic ketones, nitro, sulfhydryl, sulfonyl, sulfoxide, and combinations thereof. Two or more of the $R_5$ substituents also may be atoms, typically carbon atoms, in a ring system bonded or fused to the compounds having the illustrated general formula. At least one of the $R_1$-$R_5$ positions is bonded to a linker or is occupied by a functional group suitable for coupling to a linker or a carrier molecule. $R_1$-$R_5$ most typically are aliphatic, aryl, hydrogen, or hydroxyl, even more typically alkyl, hydrogen or phenyl. Y is oxygen or sulfur, most typically oxygen.

Particular embodiments of the benzodiazepine haptens have $R_1$ aryl, as indicated below.

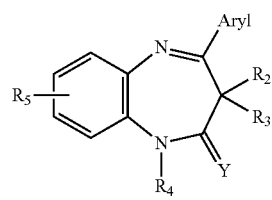

For these embodiments, $R_2$-$R_5$ are as stated above for this class of haptens, more typically such substituents are independently selected from aliphatic, particular alkyl, hydrogen and hydroxyl. Certain disclosed embodiments are phenyl compounds, as illustrated below.

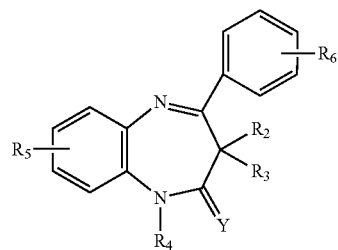

Again, $R_2$-$R_6$ are as stated above, but more typically such substituents are independently selected from aliphatic, particularly alkyl, hydrogen and hydroxyl. Certain disclosed embodiments are phenyl compounds, as illustrated below. A particular embodiment, 4-(2-hydroxyphenyl)-1H-benzo[b][1,4]diazepine-2(3H)-one, is provided below.

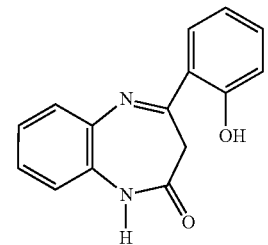 [SMILES: O=C1CC(c2ccccc2O)=Nc2ccccc2N1]

E. Linkers
1. General

As indicated by the general formula hapten-optional linker-carrier conjugates of the present application may include linkers. Any linker currently known for this purpose, or developed in the future, can be used to form conjugates of the present invention by coupling to the haptens disclosed herein. Useful linkers can either be homo- or heterobifunctional, but more typically are heterobifunctional.

2. Aliphatic

Solely by way of example, and without limitation, a first class of linkers suitable for forming disclosed hapten conjugates are aliphatic compounds, such as aliphatic hydrocarbon chains having one or more sites of unsaturation, or alkyl chains. The aliphatic chain also typically includes terminal functional groups, including by way of example and without limitation, a carbonyl-reactive group, an amine-reactive group, a thiol-reactive group or a photo-reactive group, that facilitate coupling to haptens and other desired compounds, such as specific binding moieties. The length of the chain can vary, but typically has an upper practical limit of about 30 carbon atoms. Chain links greater than about 30 carbon atoms have proved to be less effective than compounds having smaller chain links. Thus, aliphatic chain linkers typically have a chain length of from about 1 carbon atom to about 30 carbon atoms. However, a person of ordinary skill in the art will appreciate that, if a particular linker has greater than 30 atoms, and still operates efficiently for linking the hapten to a carrier molecule coupling unit, and the conjugate still functions as desired, then such chain links are still within the scope of the present invention.

3. Alkylene Oxides

A second class of linkers useful for practicing the present invention are the alkylene oxides. The alkylene oxides are represented herein by reference to glycols, such as ethylene glycols. Hapten conjugates of the present invention have proved particularly useful if the hydrophilicity of the linker is increased relative to their hydrocarbon chains. As a result, the alkylene oxides, such as the glycols, have proved useful for practicing this invention. A person of ordinary skill in the art will appreciate that, as the number of oxygen atoms increases, the hydrophilicity of the compound also may increase. Thus, linkers of the present invention generally have a formula of (—OCH$_2$CH$_2$O—)$_n$ where n is from about 2 to about 25, but more typically n is from about 2 to about 12.

Heterobifunctional polyalkyleneglycol linkers useful for practicing certain disclosed embodiments of the present invention are described in assignee's co-pending applications, including "Nanoparticle Conjugates," U.S. patent application Ser. No. 11/413,778, filed Apr. 28, 2006; "Antibody Conjugates," U.S. application Ser. No. 11/413,415, filed Apr. 27, 2006; and "Molecular Conjugate," U.S. Provisional Patent Application No. 60/739,794, filed Nov. 23, 2005; all of which applications are incorporated herein by reference. A person of ordinary skill in the art will appreciate that the linkers disclosed in these applications can be used to link specific binding moieties, signal generating moieties and haptens in any and all desired combinations. Heterobifunctional polyalkyleneglycol linkers are disclosed below, and their use exemplified by reference to coupling specific binding moieties, such as antibodies, to haptens and detectable labels. In particular, conjugates of anti-hapten antibodies and detectable labels and conjugates of primary antibodies with haptens are exemplified herein.

One particular embodiment of a linker for use with disclosed conjugates is a heterobifunctional polyalkyleneglycol linker having the general structure shown below:

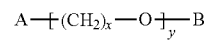

wherein A and B include different reactive groups, x is an integer from 2 to 10 (such as 2, 3 or 4), and y is an integer from 1 to 50, for example, from 2 to 30 such as from 3 to 20 or from 4 to 12. One or more hydrogen atoms can be substituted for additional functional groups such as hydroxyl groups, alkoxy groups (such as methoxy and ethoxy), halogen atoms (F, Cl, Br, I), sulfato groups and amino groups (including mono- and di-substituted amino groups such as dialkyl amino groups.

A and B of the linker can independently include a carbonyl-reactive group, an amine-reactive group, a hydrazine-reactive group, a hydrazide reactive group, a thiol-reactive group or a photo-reactive group. A and B can be the same group, or can be different groups. Examples of carbonyl-reactive groups include aldehyde- and ketone-reactive groups like hydrazine derivatives and amines. Examples of amine-reactive groups include active esters such as NHS or sulfo-NHS, isothiocyanates, isocyanates, acyl azides, sulfonyl chlorides, aldehydes, glyoxals, epoxides, oxiranes, carbonates, aryl halides, imidoesters, anhydrides and the like.

Hapten-linker conjugates have been formed using PEG-based linkers. One example of such a compound is shown below.

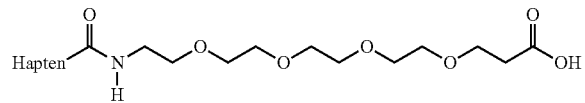

This example therefore satisfies the formula hapten-L-RG where L is a dPEG$_4$ (4 ether oxygens) and the reactive group is a carboxylic acid functional group. The carboxylic acid functional group has been converted to other reactive functional groups in working embodiments. For example, the carboxylic acid functional group can be converted to an activated ester, such as an NHS ester, as shown below.

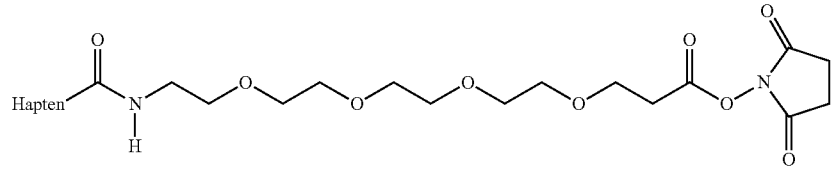

And, the activated ester can be converted to other useful reactive functional group, such as a hydrazide, as illustrated below.

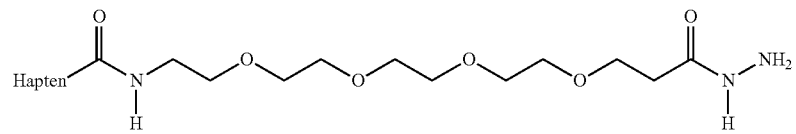

F. Miscellaneous Materials for Coupling to Polymeric Carriers

Polymeric carriers have plural functional groups through which desired compounds or functional groups can be incorporated into conjugates. For example, certain disclosed embodiments concern conjugates whereby a portion of available reactive functional groups, such as nitrogen-bearing functional groups having adjacent heteroatoms, for coupling to a hapten, or haptens, or hapten linkers, leaving a remaining portion of reactive functional groups available for reacting with a second class of desired molecule. By way of example, and without limitation, the second class of compounds includes: biological molecules (including peptides, proteins, enzymes, sugars, polysaccharides, lipids, glycoproteins, and lipoproteins); detectable labels (linkers having a first end coupled to the polymeric material and a second coupled to, or available for coupling to a desired molecule).

V. Synthesis

A. General

Detailed synthesis of polyacrylamide hydrazide is described in U.S. patent application Ser. No. 11/018,897, which is incorporated herein by reference, and is provided below in Example 1. Briefly, an aqueous mixture of polyacrylamide, commercially available from Sigma Aldrich, and hydrazine monohydrate (Sigma Aldrich) is subjected to microwave heating. This synthesis is indicated generally below in Scheme 1.

Scheme 1 Polyacrylamide Hydrazide Synthesis

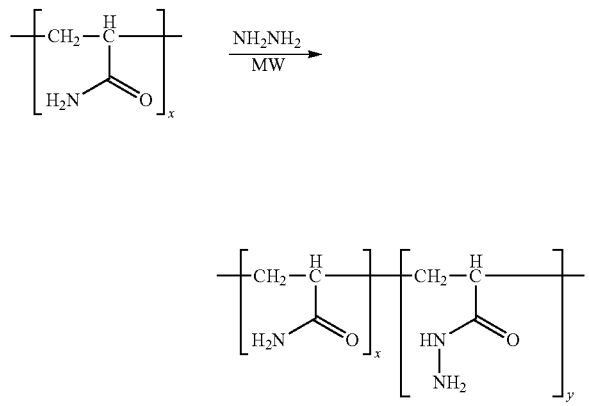

The reaction mixture is purified by precipitation and isolation of the desired polyacrylamide hydrazide.

Scheme 2 illustrates one embodiment of a microwave mediated synthesis of polyvinylpyrrolidone hydrazide.

Scheme 2 Polyvinylpyrrolidone Synthesis

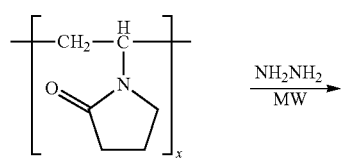

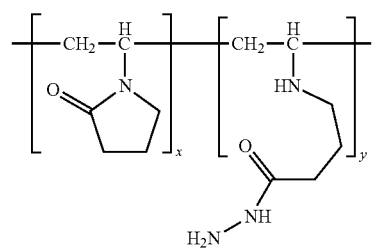

Scheme 3 illustrates one embodiment of a microwave mediated synthesis of polyisobuytlene-co-maleic hydrazide (PIBMH).

Scheme 3 Polyisobutylene-co-maleic Hydrazide

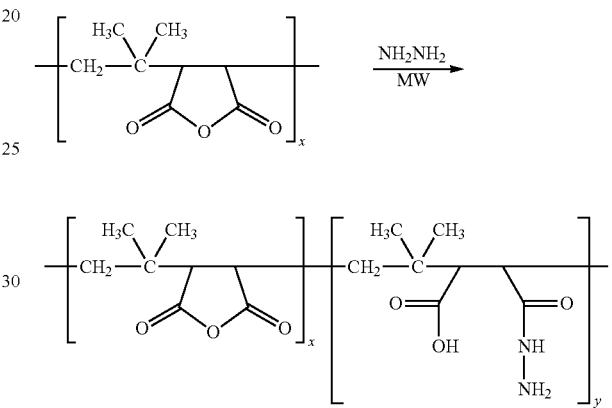

Scheme 4 illustrates one embodiment of a synthesis of polyacrylic acid hydrazide. Microwave mediated synthesis of the polyacrylic acid hydrazide polymer leads to little or no product. Without being bound by a theory of operation, it may be that the hydrazine does not react, or does not react well, with the free acid functional groups of the polyacrylic acid, whereas hydrazine does react with amide and acid anhydride functional groups, as illustrated above. As a result, one embodiment of a successful synthesis is to activate the carboxylic acid functional groups, followed by reaction with a protected hydrazine, such as a BOC-protected hydrazine. A person of ordinary skill in the art will appreciate that acid functional groups may be activated for reaction with a nucleophile, such as hydrazine or other reactive functional group, in a variety of ways. However, the illustrated working embodiment used 1-[3-(dimethylamino) propyl]-3-ethylcarbodiimide (EDAC) to activate the carboxylic acid functional groups for substitution with a BOC-protected hydrazine. The BOC protecting group was removed with trifluoroacetic acid (TFA) to produce the polyacrylic acid hydrazide polymer.

Scheme 4 Polyacrylic Acid Synthesis

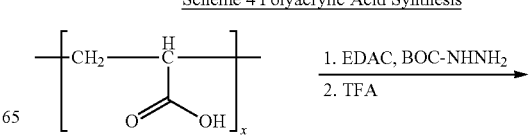

-continued

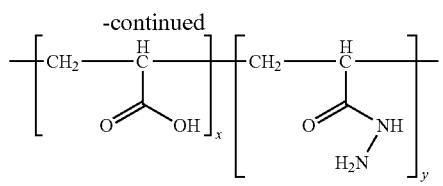

B. Conjugate Synthesis Using Polymeric Hydrazide as an Exemplary Synthesis

Figure 2:
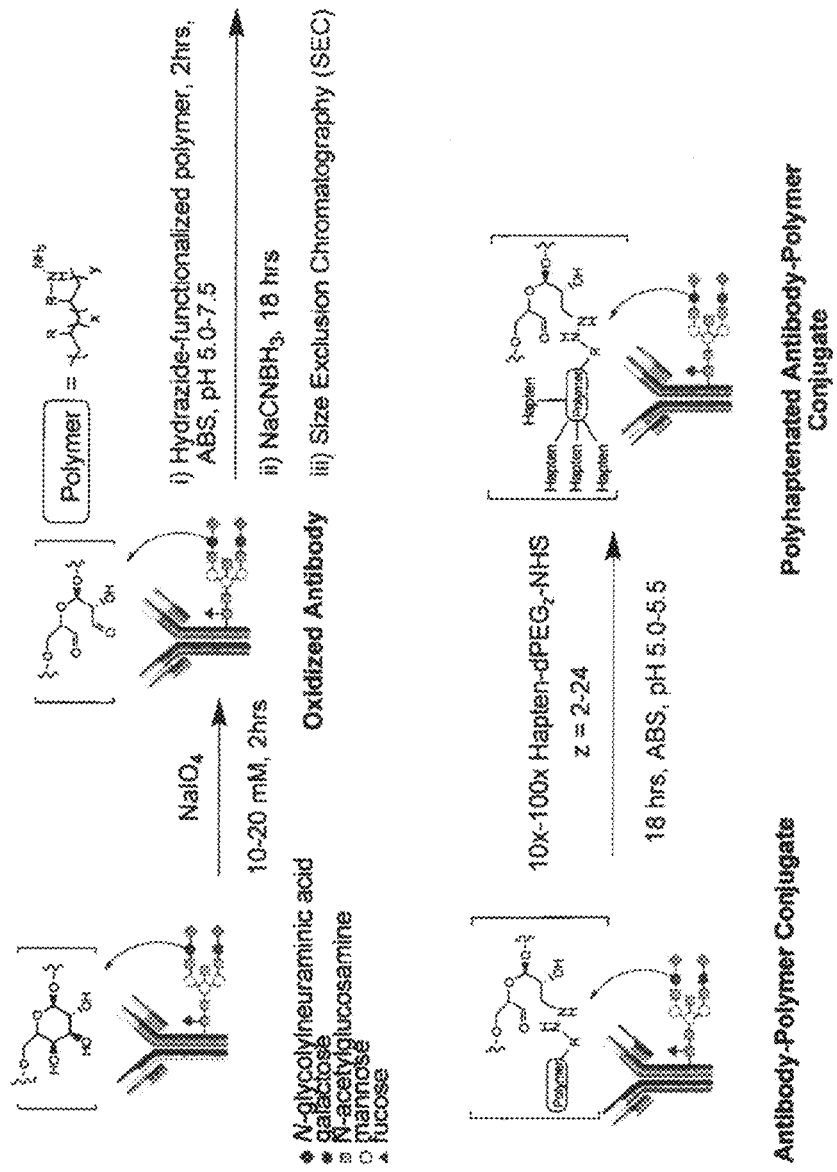
FIG. 2 illustrates one embodiment of a method for synthesizing an Fc-Specific Ab-hydrazide-functionalized polymer-polyhapten conjugate.
Figure 3:
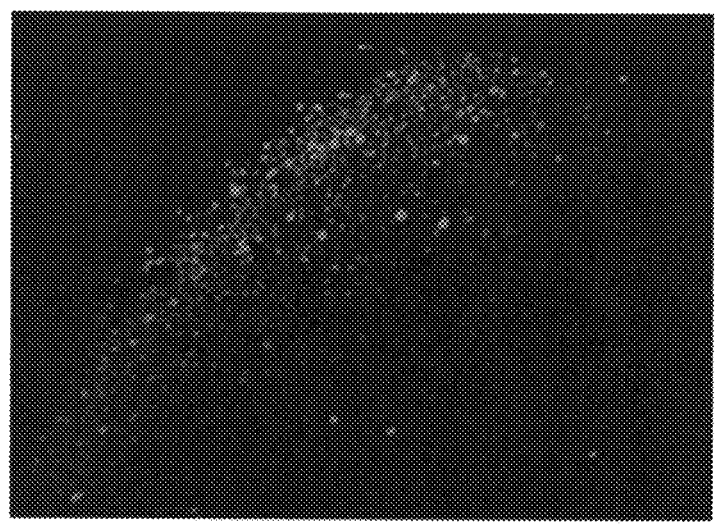
FIG. 3 is a photograph illustrating staining of Ki-67 on tonsil (655 nm filter; 20× magnification) using a streptavidin-quantum dot 655 conjugate with the Fc-specific biotinylated antibody.
Figure 4:
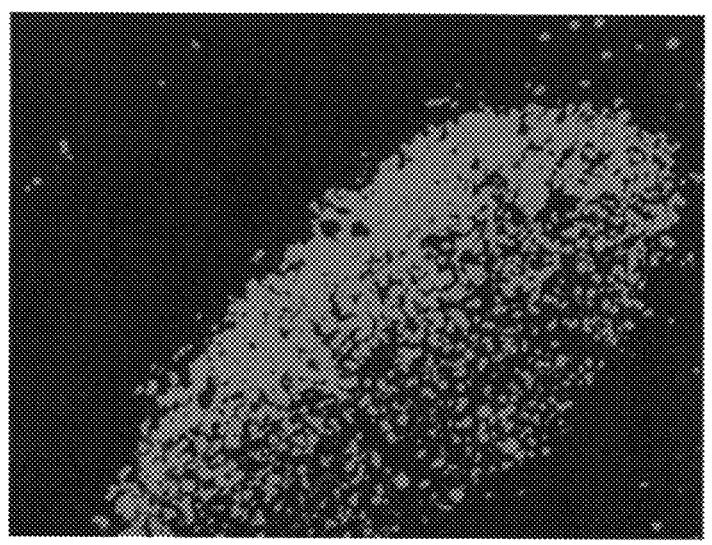
FIG. 4 is a photograph illustrating staining of Ki-67 on tonsil (655 nm filter; 20× magnification) using a streptavidin-quantum dot 655 conjugate with the biotinylated polyacrylamide hydrazide antibody.

While the present invention can be practiced using various polymeric carriers, the following discussion exemplifies the invention with reference to polyacrylamide hydrazide as the polymeric carrier. The polyacrylamide hydrazide is coupled to a specific binding molecule, such as an antibody, as illustrated by FIG. 2. For compounds that include a hydrazide reactive moiety, then no activation of the compound is necessary. Alternatively and where necessary or desirable, the antibody can be activated for coupling to a polymeric carrier. For example, one activation technique involves providing or producing a hydrazide-reactive functional group on the antibody. A particularly useful embodiment of the present invention is coupling the polymeric carrier, such as a polymeric hapten carrier, to the Fc portion of an antibody. To ensure that this reaction occurred, working embodiments typically have oxidized carbohydrate portions associated with the Fc portion of the antibody to create a hydrazide reactive functional group, typically a compound bearing a carbonyl, such as an aldehyde, or reactive ketone, acid or ester, most typically an aldehyde, using an appropriate oxidizing agent, such as periodate. For working embodiments, excess sodium periodate was used to oxidize proteins.

For the embodiment illustrated in FIG. 2, an intermediate hydrazone is formed by coupling a polymeric carrier to an aldehyde formed at the Fc portion of the antibody. Working embodiments reduced this intermediate hydrazone using an appropriate reagent, such as sodium cyanoborohydride. However, reduction of the intermediate hydrazone may not be required. Working embodiments reduced the intermediate hydrazone to provide increased stability, such as by eliminating the possibility of a retro-Mannich reaction of the Mannich base. As another example, intermediate hydrazones may be reactive with other components, either intra- or inter-molecularly, to produce less desirable compounds, such as stable heterocycles.

FIG. 2 illustrates that resulting compounds have plural, i.e. "y," hydrazide functional groups that are available for reaction with another desired compound. This aspect of certain disclosed embodiments is illustrated in FIG. 2, illustrating the principle with particular reference to coupling haptens to the polymeric carrier. As with the antibody, haptens capable of directly reacting with the antibody may not need to be activated prior to such coupling. Alternatively, a linker may be used to couple the polymeric carrier-antibody conjugate to a hapten, or haptens, to form a polymeric hapten carrier-antibody conjugate if activation is desirable or required, and/or if some other reason favors using a linker, such as spacing the hapten from the antibody for steric reasons or to facilitate recognition of the pendent hapten(s). Additional information concerning compositions and uses of linkers can be found in assignee's patents and/or applications that are incorporated herein.

FIG. 2 illustrates using various linkers, such as dPEG$_4$ to dPEG$_{24}$ linkers, and alkyl linkers, such as —C$_5$H$_{11}$, to couple DNP, biotin and fluorescein, respectively, to hydrazide functional groups of the polymeric carrier-antibody conjugate. To facilitate coupling the polymeric carrier-antibody conjugate to the linker-hapten, the linker includes an activated ester, with an N-hydroxysuccinimide (NHS) ester being illustrated in FIG. 1. The polymeric carrier-antibody conjugate is coupled to the hapten to form a polymeric hapten carrier conjugate.

FIG. 2 illustrates that all available "y" groups, that is functional groups comprising free hydrazide functional groups, react with the activated hapten-linker. A person of ordinary skill in the art will appreciate that only a portion of the available reactive functional groups may react, such as by using a stoichiometrically limited amount of the linker-hapten. These compounds would have additional reactive functional groups available for reacting with, for example, a different hapten or hapten-linker.

FIG. 2 illustrates first reacting the polymeric carrier with an antibody to form a polymeric carrier-antibody conjugate, and then coupling a hapten, haptens, hapten-linker, haptens-linker, hapten-linkers, and/or haptens-linkers (collectively referred to as hapten/hapten-linker), to the polymeric carrier-antibody conjugate. A person of ordinary skill in the art will appreciate that the same compounds optionally may be formed by first coupling a polymeric carrier to a hapten/hapten-linker to form a polymeric hapten carrier. The polymeric hapten carrier, having remaining available reactive functional groups, is then coupled with the antibody, preferably solely at the Fc portion of the antibody, to form a polymeric hapten carrier-antibody conjugate.

VI. Exemplary Disclosed Embodiments of a Method for Using Disclosed Polymeric Hapten Carrier Conjugates, and Compositions Thereof Certain exemplary embodiments of the present invention concern in situ hydridization techniques that can be implemented with various embodiments of disclosed polymeric hapten carrier conjugates. A sample having a target, such as a protein, is selected. A probe useful for detecting the target, such as an antibody, also is selected. At least one polymeric hapten carrier is conjugated to the probe. The target is treated with the probe conjugated to the polymeric hapten carrier in a manner effective to form a complex that can be visualized using any suitable means, such as by treating the target complexed with the probe-polymeric hapten carrier conjugate with an anti-hapten antibody having a detectable label, such as an enzyme, an organic chromophore, such as a flourphore, chromophoric nanoparticles, such as fluorescent quantum dots, etc., suitable for visualizing the resulting complex. For example, if the detectable label is an enzyme, a substrate for the enzyme is provided, thereby producing a uniquely identifiable precipitate, such as a colored precipitate.

An antibody may be coupled to detectable label, such as an enzyme. An enzyme substrate is added to produce a detectable enzymatic product. One specific embodiment of this process is Silver in situ Hydridization (SISH). One suitable enzyme for SISH is horseradish peroxidase, which can be used in combination with hydroquinone, silver ions (e.g., $Ag^{+1}$) and hydrogen peroxide. The detectable product is elemental silver particles. Additional information concerning such processes can be found in Hainfeld, U.S. Pat. No. 6,670, 113, which is incorporated herein by reference.

As another example, the enzyme might be alkaline phosphatase. Alkaline phosphatase triggers catalytic hydrolysis of reducing agent phosphate, i.e. ascorbic acid phosphate, generating a reducing agent, i.e. ascorbate, which then may be used to reduce silver plus one ($Ag^{+1}$) to metallic nanoscopic silver. Thus, the visually detectable product is elemental silver. Silver can be detected by any suitable means, including bright field microscopy. Additional information concerning using phosphatase enzymes can be found in Bieniarz et al., U.S. Patent Application No. 2004/0265922, entitled "Enzyme-catalyzed Metal Deposition for the Enhanced in Situ Detection of Immunohistochemical Epitopes and Nucleic Acid Sequences," which is incorporated herein by reference.

Embodiments disclosed herein also can be used to implement Chromogenic In situ Hydridization. In this process, an enzyme is selected, with suitable examples including those disclosed herein or that are otherwise known to those of ordinary skill in the art, with horseradish peroxidase and alkaline phosphatase being used to exemplify particular embodiments. A substrate is then selected suitable for producing a colored precipitate product that can be detected using techniques known in the art, including bright field microscopy. The chromogenic compound can be fluorogenic. Suitable fluorogenic compounds are commercially available from various sources. The substrate can be made fluorogenic by enzymatic action. Quantum dots also can be used to visualize immunohistochemical interactions too. Fluorescent probes and quantum dots typically are monitored using a fluorescence microscope.

Additional embodiments of a disclosed method concern a direct detection process. For this process, a primary antibody, including a monoclonal antibody, such as mouse monoclonal IgG antibody, is selected for a particular target. The primary antibody also typically includes a detectable label, as discussed above.

Alternatively, an amplification process can be used. This embodiment also can be used for diagnostic tests. A target is selected. A primary antibody is added to the sample in a manner to allow complexation of the target and primary antibody. A secondary antibody against the primary antibody is added to the sample. The antibody includes a detectable label that can be used to identify, particularly visually or by visual means, such as microscopy, the complexed target using a substrate, as discussed herein. The antibody can be any suitable antibody, including by way of example and without limitation, a labeled rabbit anti-mouse IgG antibody. A secondary antibody, including an antibody from a different species, to the primary antibody can be added to the sample. For example, the antibody might be a goat antibody raised against the primary antibody, such as mouse IgG antibodies.

At least one additional anti-antibody having a detectable label may be added to the sample to amplify the signal produced by the detected target. In this exemplary process, the antibody might be a labeled rabbit anti-goat IgG antibody. The antibody can be added simultaneously with, or subsequent to, as the labeled antibody.

Certain embodiments of the present invention are facilitated by using anti-hapten monoclonal antibodies, such as for hybridoma screening. A particular target is selected, such as a target situated in a tissue. A primary antibody directed to the target is administered in a manner effective for the antibody to recognize the target. The antibody has at least one, and potentially plural, haptens conjugated thereto using polymeric hapten carrier conjugates of the present invention. The haptens conjugated to the primary antibody can be the same or different. A tissue sample is treated with anti-hapten antibodies. In this exemplary embodiment, a primary antibody effectively becomes coupled to an anti-hapten antibody, such as may be provided from a hybridoma mouse monoclonal antibody. Thus, for each hapten coupled to the primary antibody, there will be a secondary antibody.

The complex formed by the anti-hapten antibody, such as a mouse monoclonal antibody, then is identified. One method is to now treat the composition with an antibody that recognizes the mouse antibody, such as a goat antibody. In this exemplary embodiment, goat antibodies are conjugated to a detectable label, such as an enzyme, one example being horseradish peroxidase (HRP) enzymes. This complex is then incubated with an HRP substrate, as is known to persons of ordinary skill in the art, to form detectable, e.g. colored, precipitates. This process can be used for screening, such as hybridoma screening.

To screen for antihapten monoclonal antibodies, a tissue sample, such as normal human tonsil tissue, is obtained. The sample may be embedded in paraffin, and if so, the tissue sample is deparaffinized, such as by using VMSI EZPrep solution. Cell conditioning and antigen retrieval is then performed using VMSI CC1. A primary polyclonal antibody, such as human anti-lambda (available from Dako), is conjugated to embodiments of polymeric hapten carriers disclosed in the present application. Conjugation preferably occurs at the Fc region of the antibody to reduce the likelihood that the binding will affect the antibody specificity. A solution comprising an effective amount of the primary antibody is applied to the tissue for an effective period of time. For working embodiments the effective concentration has been about 10 μg/ml of the primary antibody, and the effective time period has been about 60 minutes. The tissue sample is then washed. Thereafter, a potential anti-hapten antibody (e.g. KLH-CGT1-1.1+5-27F09-02E01) is applied to the tissue sample for an effective period of time, such as about 60 minutes. The antibody is then detected using any suitable means, such as VMSI Omni Map DAB stain.

Automated immunohistochemistry (IHC) screening of potential anti-hapten antibodies can be performed using a VMSI Discovery XT and formalin-fixed, paraffin-embedded human tonsil tissue on glass slides. Tissue samples first undergo deparaffinization, antigen retrieval, followed by the addition of a primary antibody linked to a hapten of interest using a polymeric hapten carrier, the potential anti-hapten antibody and a detection antibody. The detection antibody is visualized using a chromogen detection reagent from VMSI. Stained slides are manually screened under a microscope. Samples having a correct primary antibody staining pattern are selected as potential anti-hapten candidates. To test for selectivity and specificity, candidate anti-hapten cell fusion products are further screened using primary antibodies conjugated to a hapten of a different chemical class.

Disclosed embodiments contemplate using multiple different haptens, and antibodies thereto, to visualize a detectable target. For example, biotin and DNP haptens, and antibodies thereto, such as antibiotin and anti-DNP, can be used for detection of a target in a sample, such as a protein in tissue.

Embodiments of the present invention also are useful for simultaneous detection of multiple different types of targets, such as protein targets, in a sample. For example, with reference to HER2 (human epidermal growth factor receptor 2), a polymeric hapten carrier labeled HER2 probe is added to a sample in a manner effective to allow the probe to complex with the HER2 gene. The complexed gene is then treated with an anti-hapten antibody having a detectable label 206, such as a Qdot. An anti-HER2 protein antibody, such as Anti-HER2 4B5 rabbit antibody, is added to the sample in a manner effective to allow recognition of the HER2 protein. The anti-HER2 antibody may include at least one polymeric hapten carrier, and potentially plural haptens, which may be the same or different. With reference to using biotin to exemplify the embodiment, an anti-hapten secondary antibody is then added to the sample in a manner effective to allow complexation of the secondary antibody and hapten(s). Anti-hapten secondary antibody includes a detectable label, such as a Qdot 655. Thus, this embodiment allows multiplexed detection of gene and gene product.

VII. Test Kits

Disclosed embodiments of the present invention provide, in part, kits for carrying out various embodiments of the method of the invention. Examples of such kits include those useful for cholesterol analyses, pregnancy kits, cancer diagnostic kits, etc. Test kits of the present invention typically have a polymeric hapten carrier conjugate according to the present invention, such as at least one polymeric hapten carrier-specific binding molecule conjugate, including polymeric hapten carrier-antibody conjugates, and an anti-hapten antibody, particularly an anti-hapten antibody conjugated to a detectable label.

Certain kit embodiments comprise a polymeric hapten carrier-conjugated antibody, the hapten being selected from oxazoles, pyrazoles, thiazoles, nitroaryls, benzofurazans, triterpenes, ureas, thioureas, rotenones, coumarins, cyclolignans, and combinations thereof. Such kits also typically include an anti-hapten antibody conjugated to a detectable label.

Further, disclosed kit embodiments can include additional components, including but not limited to plural additional antibodies. Such kits may be used, for example, by a clinician or physician.

VIII. Automated Embodiments

A person of ordinary skill in the art will appreciate that embodiments of the method disclosed herein for using hapten conjugates can be automated. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. published application Nos. 20030211630 and 20040052685, each of which is incorporated herein by reference. Particular embodiments of polymeric hapten staining procedures can be conducted using various automated processes.

Additional details concerning exemplary working embodiments are provided in the working examples.

IX. Examples

The following examples are provided to illustrate certain features of working embodiments. A person of ordinary skill in the art will appreciate that the scope of the present invention is not limited to the particular features exemplified by these examples.

For all disclosed working examples, all chemicals were purchased from commercial suppliers and used as received. Solutions of polyclonal antibody (goat anti-mouse and goat anti-rabbit) were purchased from Bethyl Labs and were used as received. Polyacrylamide hydrazide and NHS-PEG$_4$-DNP were synthesized as previously described. Protein concentrations were calculated using $\epsilon_{280}$ values of 1.4 ml mg$^{-1}$ cm$^{-1}$ for the antibody. Water, obtained from an internal deionization source, was passed through a Milli-Q Biocel System to remove impurities. Buffer exchange was performed using PD-10 columns (GE Biosciences). SEC was done using an Akta Purifier (GE Biosciences) and molecular weights are referenced to protein standards. The flow rate was 1 milliliter/minute through a Superdex 200 GL 10/300 column (GE Biosciences).

Example 1

This example describes one embodiment of a method for making polyacrylamide hydrazide, as originally disclosed in U.S. patent application Ser. No. 11/018,897, which is incorporated herein by reference. Polyacrylamide (1 mmol, 20 mL, 50 wt % solution, Sigma-Aldrich) was mixed with distilled water (10 mL) and hydrazine monohydrate (20 mL, 420 mmol, Sigma-Aldrich) in a 100 mL round-bottom flask fitted with a condenser. The reaction mixture was microwaved in a CEM Discovery unit for 60 minutes. After cooling to room temperature, an equal volume of methanol was added to the reaction mixture to induce precipitation. The resulting mixture was centrifuged and decanted. The residue was taken up in deionized water (50 mL), and the precipitation process repeated for a total of three times. The final residue was dissolved in deionized water and lyophilized to give a fine, white hygroscopic powder.

Example 2

This example describes one embodiment of a method for synthesizing an Fc-specific haptenylated antibody, as illustrated in FIG. 1. To a solution of polyclonal antibody (1.5 ml, 3.0 mg/ml) was added sodium periodate (0.5 ml, 10 mg/ml in deionized water) for a final periodate concentration of 11.7 mM. The reaction solution was rotated for two hours before desalting with a PD-10 column (0.1 M sodium acetate, 0.15 M NaCl, pH=5.5) to remove unreacted periodate. The hapten-dPEG$_x$-hydrazide was added in a 500-fold molar excess to the oxidized antibody followed by sodium cyanoborohydride (3.14 mg, 50 µmol) and the reaction was incubated for a period of 18 hours. Size exclusion chromatography (0.1 M Na$_3$PO$_4$, 0.15 M NaCl, pH=7.5) gave the purified haptenylated antibody. The number of DNP ($\epsilon_{360}$=18,200 M$^{-1}$ cm$^{-1}$; $\epsilon_{280}$=6,500 M$^{-1}$ cm$^{-1}$) per antibody was calculated using UV-Vis measurements while the number of accessible biotin per antibody was measured using an HABA assay available through Sigma-Aldrich.

Example 3

This example describes one embodiment of a method for synthesizing a polyhaptenylated IgG conjugate as illustrated in FIG. 2.

A. Synthesis of Fc-specific PAH Ab

To a solution of polyclonal antibody (1.5 ml, 3.0 mg/ml) was added sodium periodate (0.5 ml, 10 mg/ml in deionized water) for a final periodate concentration of 11.7 mM. The reaction solution was rotated for two hours before desalting with a PD-10 column (0.1 M sodium phosphate, 0.15 M NaCl, pH 7.5) to remove unreacted periodate. The polyacrylamide hydrazide linker was added in a 50-fold molar excess to the antibody along with sodium cyanoborohydride (3.14 mg, 50 µmol) and the reaction was incubated for a period of 18 hours. SEC (0.1 M sodium acetate, pH 5.0) yielded the purified antibody-PAH conjugate.

B. Synthesis of Polyhaptenylated Antibody

To a solution of the PAH-IgG (2.0 ml, 0.53 mg/ml) was added NHS-dPEG$_x$-hapten (50-fold excess) and the reaction was incubated for a period of 18 hours. SEC (0.1 M sodium phosphate, 0.15 M NaCl, pH=7.5) resulted in the purified polyhaptenylated antibody. The number of haptens per antibody was calculated using UV-Vis measurements while the number of accessible biotin-per-antibody was measured using an HABA assay available through Sigma-Aldrich.

Example 4

This example describes one embodiment of a method for synthesizing a chemoselective Fc-specific polyacrylamide hydrazide-antibody conjugate as illustrated generally in FIG. 2. A solution of a polyclonal antibody (0.8 m/L of 1.0 mg/mL) was incubated with a 100 mM aqueous solution of sodium periodate (0.2 ml) for two hours at room temperature. The solution was buffer exchanged by passing through a column of G-25 (GE Lifesciences, PD-10 column) using ABS (0.10 M sodium acetate, 0.15M NaCl, pH 5.5). PAH was added to the oxidized Ab using a 50-fold molar excess to the Ab and incubated at room temperature for one hour. Sodium cyanoborohydride (50 molar excess) was added and incubated for 18 hours at room temperature. The PAH-Ab was purified on a size exclusion column using ABS (0.10 M acetate, 0.15M NaCl, pH 5.5). The NHS-dPEG$_x$-hapten (10-100× molar excess) was added and the reaction was incubated for a period of 18 hours. SEC (0.1 M sodium phosphate, 0.15 M NaCl, pH=7.5) resulted in the purified polyhaptenylated antibody. The number of haptens per antibody was calculated using UV-Vis measurements while the number of accessible biotin-per-antibody was measured using an HABA assay available through Sigma-Aldrich. The number of haptens was less than conjugates in Example 3, but higher than Example 2.

Example 5

This example describes one embodiment of a method for synthesizing a nitropyrazole-labeled polyacrylamide hydrazide-antibody conjugate as illustrated generally in FIG. 2. Purified polyacrylamide hydrazide-antibody conjugate in ABS (0.10M sodium acetate, 0.15 M NaCl, pH 5.5) was incubated with a 20-fold molar excess of nitropyrazole-dPEG$_8$-NHS for 18 hours. The mixture was purified by size-exclusion chromatography using PBS (0.10 M sodium phosphate, 0.15 M NaCl, pH 7.2) to yield poly-nitropyrazole-PAH-Ab. The number of nitropyrazoles per PAH-Ab was determined by UV-Vis measurements.

Example 6

This example describes one embodiment of a method for synthesizing a benzofurazan-labeled polyacrylamide hydrazide-antibody conjugate as illustrated generally in FIG. 2. Purified polyacrylamide hydrazide-antibody conjugate in ABS (0.10 M sodium acetate, 0.15 M NaCl, pH 5.5) was incubated with 20-fold molar excess of benzofurazan-dPEG$_8$-NHS for 18 hours. The mixture was purified by size-exclusion chromatography using PBS (0.10 M sodium phosphate, 0.15 M NaCl, pH 7.2) to yield poly-benzofurazan-PAH-Ab. The number of benzofurazans per PAH-Ab was determined by UV-Vis measurements.

Example 7

This example describes one embodiment of a method for synthesizing dinitrophenyl-labeled polyacrylamide hydrazide-antibody conjugate as illustrated generally in FIG. 2. Purified polyacrylamide hydrazide-antibody conjugate in ABS (0.10 M sodium acetate, 0.15 M NaCl, pH 5.5) was incubated with a 100-fold molar excess of dinitrophenyl-dPEG$_8$-NHS for 18 hours. The mixture was purified by size-exclusion chromatography using PBS (0.10 M sodium phosphate, 0.15 M NaCl, pH 7.2) to yield poly-dinitrophenyl-PAH-Ab. The number of dinitrophenyls per PAH-Ab was determined by UV-Vis measurements.

Example 8

This example describes one embodiment of a method for synthesizing thiazolesulfonamide-labeled polyacrylamide hydrazide-antibody conjugate as illustrated generally in FIG. 2. Purified polyacrylamide hydrazide-antibody conjugate in ABS (0.10 M sodium acetate, 0.15 M NaCl, pH 5.5) was incubated with a 20-fold molar excess of thiazolesulfonamide-dPEG$_8$-NHS for 18 hours. The mixture was purified by size-exclusion chromatography using PBS (0.10 M sodium phosphate, 0.15 M NaCl, pH 7.2) to yield poly-thiazolesulfonamide-PAH-Ab. The number of thiazolesulfonamides per PAH-Ab was determined by UV-Vis measurements.

Example 9

Figure 5:
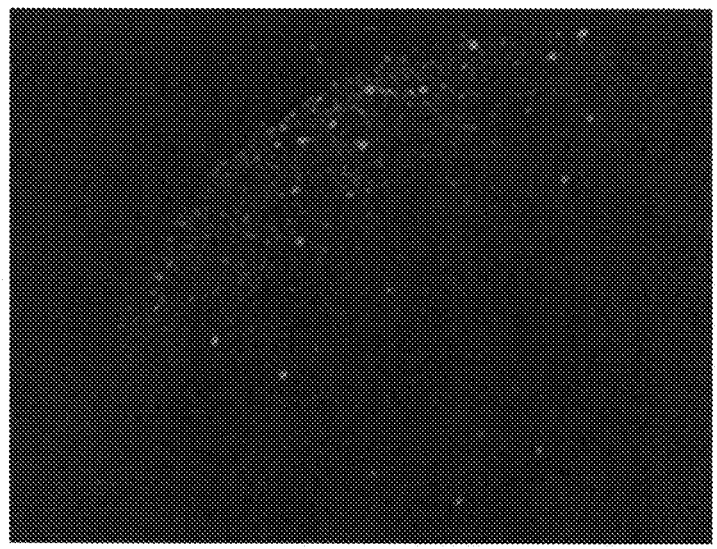
FIG. 5 is a photograph illustrating staining of a 1:10 dilution of Ki-67 on tonsil (655 nm filter; 20× magnification) using a streptavidin-quantum dot 655 conjugate with the Fc-specific biotinylated antibody.
Figure 6:
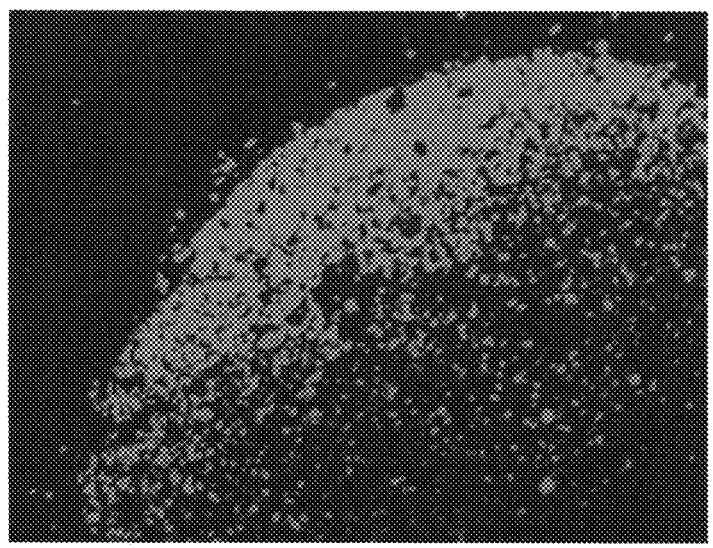
FIG. 6 is a photograph illustrating staining of a 1:10 dilution of Ki-67 on tonsil (Long Pass filter, Omega Optical XFO5-2; 20× magnification) using a streptavidin-quantum dot 655 conjugate with the biotinylated polyacrylamide hydrazide antibody.

This example concerns detecting tissue epitopes, particularly Ki-67 on tonsil, using quantum dots to recognize a secondary antibody conjugated with a polyhaptenylated polymer. The following is the adapted procedure from the Ventana Benchmark Instrument. The paraffin coated tissue on the slide was heated to 75° C. for 4 minutes and treated twice with EZPrep volume adjust (VMSI) at 75° C. before application of the liquid cover slip (VMSI) with EZPrep volume adjust. After 4 minutes at 75° C., the slide was rinsed and EZPrep volume adjust was added along with liquid cover slip to deparaffin the tissue at 76° C. for 4 minutes. The slide was cooled to 40° C. and rinsed three times before the addition of a mouse anti-Ki67 (100 μL, VMSI) antibody followed by liquid cover slip and incubation at 40° C. for 16 minutes. After rinsing the slide, the tissue was treated with a goat anti-mouse-PAH-biotinylated antibody (100 μL) followed by liquid cover slip and incubation at 40° C. for 8 minutes. The slide was rinsed twice with buffer followed by the application of liquid cover slip and the addition of 655 nm QDot-SA conjugate (100 μL, 20 mmol) and incubation at 37° C. for 16 minutes. The slide was rinsed three times with buffer and treated to a detergent wash before manual application of a cover slip to the slide, after which the slide was viewed through a microscope. FIGS. 3-6 illustrate staining results obtained according to this example, with FIGS. 5 and 6 illustrating staining results obtained using a 10-fold dilution of the primary antibody.

Example 10

Figure 7:
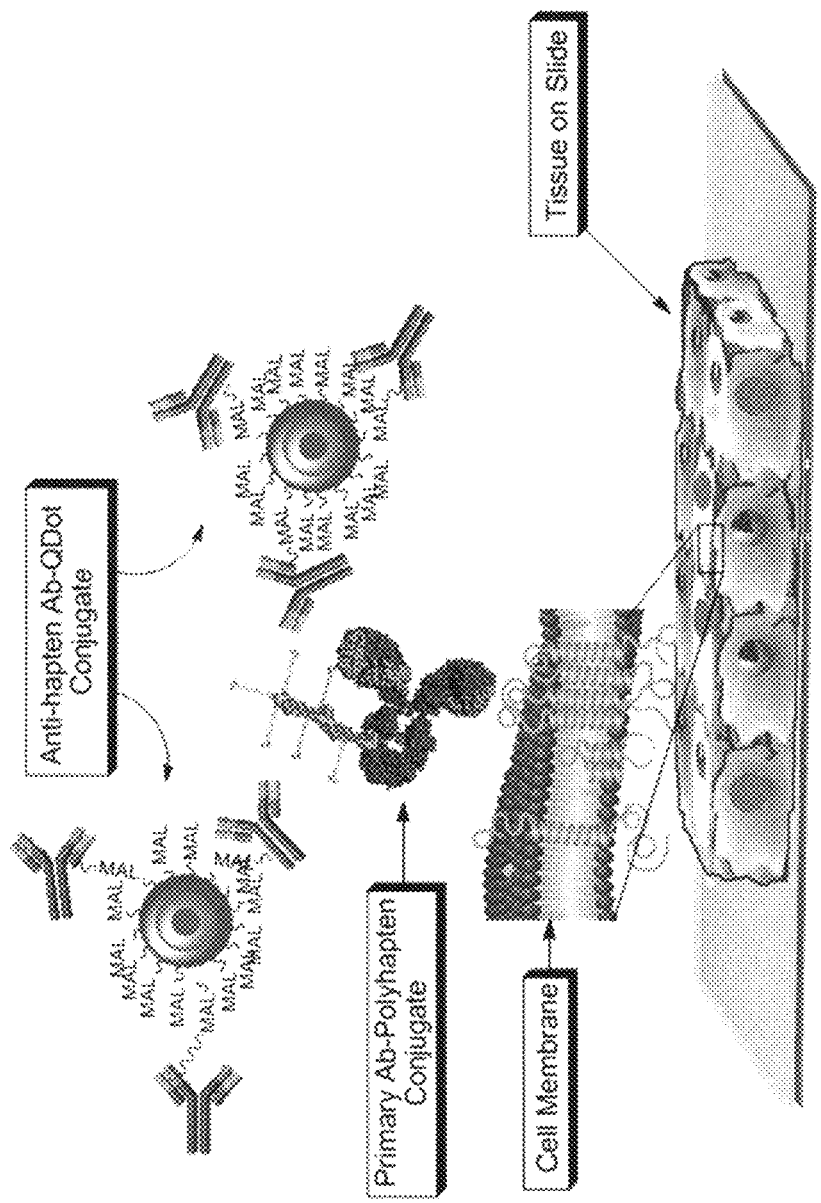
FIG. 7 illustrates one embodiment of a staining protocol for QDot IHC detection.
Figure 8:
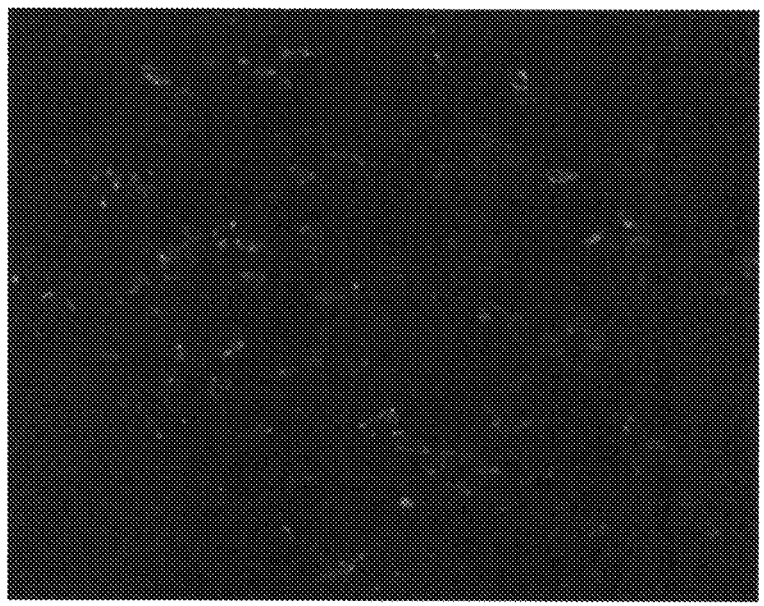
FIG. 8 is a photograph illustrating staining of tonsil tissue (Long Pass filter, Omega Optical XFO5-2; 20× magnification) using an anti-nitropyrazole-quantum dot 655 conjugate with an anti-lambda polyacrylamide hydrazide nitropyrazole conjugate.
Figure 9:
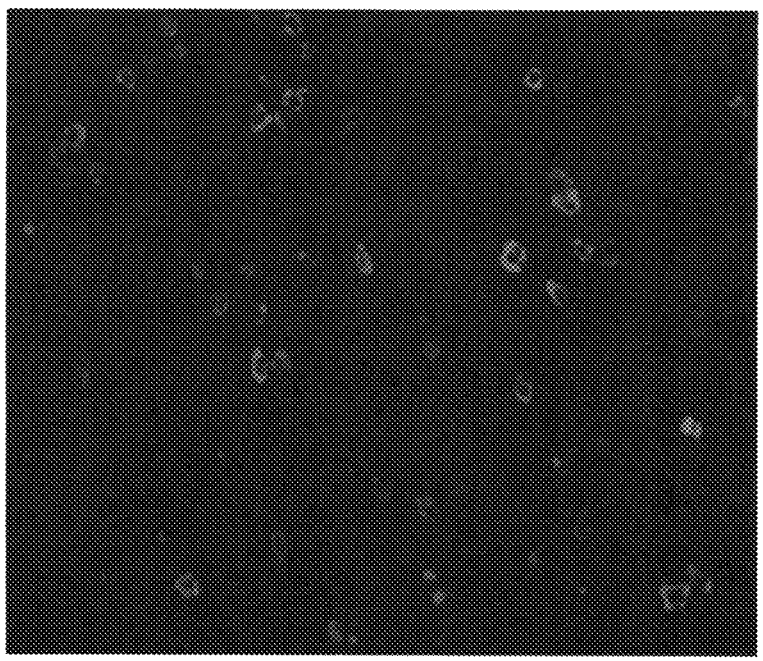
FIG. 9 is a photograph illustrating staining of tonsil tissue (Long Pass filter, Omega Optical XFO5-2; 20× magnification) using an anti-benzofurazan-quantum dot 585 conjugate with an anti-lambda polyacrylamide hydrazide benzofurazan conjugate.
Figure 10:
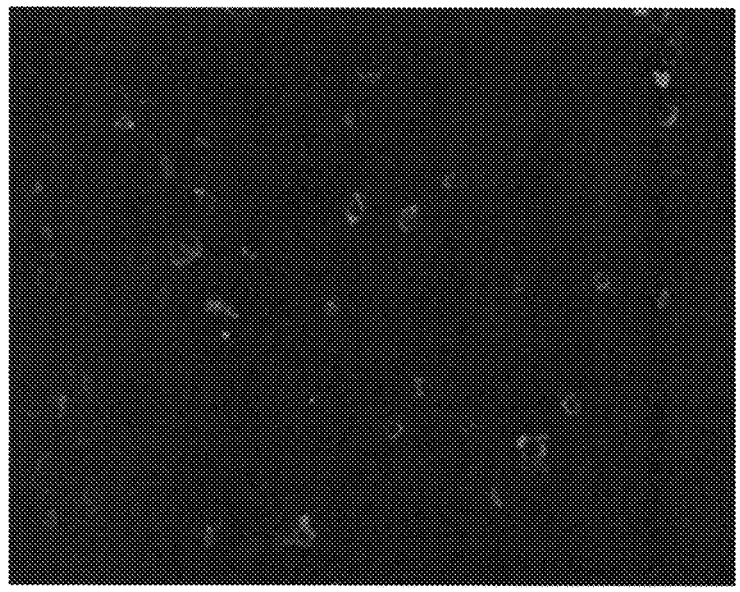
FIG. 10 is a photograph illustrating staining of tonsil (Long Pass filter, Omega Optical XFO5-2; 20× magnification) using an anti-dinitrophenyl quantum dot 605 conjugate with an anti-lambda polyacrylamide hydrazide dinitrophenyl conjugate.
Figure 11:
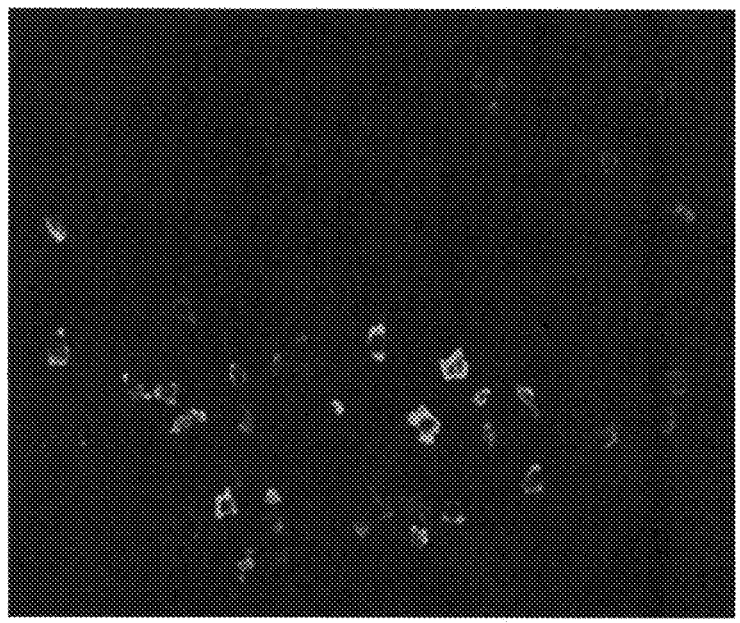
FIG. 11 is a photograph illustrating staining of tonsil tissue (Long Pass filter, Omega Optical XFO5-2; 20× magnification) using an anti-thiazolesulfonamide-quantum dot 565 conjugate with an anti-lambda polyacrylamide hydrazide thiazolesulfonamide conjugate.

This example illustrates the evaluation of anti-lambda on tonsil using quantum dots conjugated directly to secondary anti-hapten antibodies as illustrated generally in FIG. 7. The procedure is an adaptation of the automated staining protocol from the Ventana Benchmark Instrument. The paraffin coated tissue on the slide was heated to 75° C. for 8 minutes and treated twice with EZPrep, volume adjusted (VMSI) at 75° C. before application of the liquid cover slip (VMSI). After two 8 minute incubation times at 75° C., the slide was rinsed and EZPrep volume adjusted, followed with liquid coverslip to deparaffinize the tissue. The slide was cooled to 37° C., incubated for 2 minutes and rinsed once with reaction buffer. The slide was then treated with cell conditioner twice, followed by liquid coverslip. The slide is heated to 95° C. for 8 minutes, followed by coverslip, then is heated to 100° C. for 4 minutes, followed by coverslip. "Apply cell conditioner, incubate for 4 minutes, apply coverslip", this incubation process with cell conditioner was repeated 9 times at 100° C. Slide was cooled down for 8 minutes, rinsed with reaction buffer, volume adjust, followed by liquid coverslip. The slide is heated to 37° C. for 2 minutes and rinsed two times before the addition of the primary conjugate (anti-Lambda-PAH-dPEG$_8$-hapten, 100 µL, VMSI) followed by liquid cover slip and incubation at 37° C. for 32 minutes. The slide was rinsed twice with reaction buffer followed by the application of liquid cover slip and the addition of the appropriate anti-hapten Ab-quantum dot conjugate (100 µL, 20-50 nmol) and incubated at 37° C. for 32 minutes. The slide was rinsed two times with buffer followed by liquid coverslip. The slide is removed from the instrument and treated with a detergent wash before manual application of a cover slip. The slide image was captured by using a CRI Imaging camera on a fluorescent microscope with a long-pass filter and image enhancement software (Acquity). FIGS. 8-11 illustrate staining results obtained according to this example.

Example 11

Figure 12:
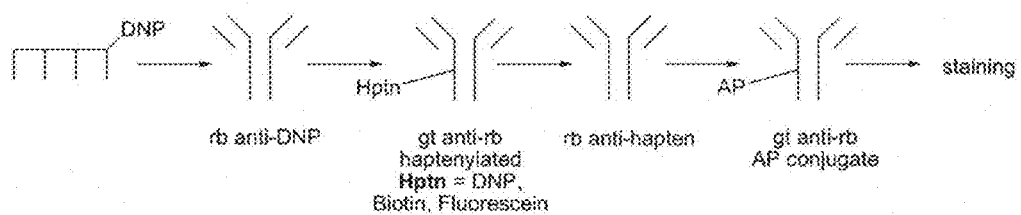
FIG. 12 illustrates one embodiment of a staining protocol for HPV AP-ISH detection.

This example concerns evaluating alkaline phosphatase-antibody multimeric conjugates, particularly HPV in different tissues using Fc-hydrazide-dPEG$_x$-hapten conjugates followed by AP-IgG detection as depicted in FIG. 12. The following is an adapted procedure from the Ventana Benchmark Instrument: the paraffin coated tissue on the slide was heated to 75° C. for 4 minutes and treated twice with EZPrep volume adjust (VMSI) at 75° C. before application of the liquid cover slip (VMSI) with EZPrep volume adjust. After 4 minutes at 75° C., the slide was rinsed and EZPrep volume adjust was added along with liquid cover slip to deparaffin the tissue at 76° C. for 4 minutes. Cell Conditioner #2 (VMSI) was added, the slide warmed to 90° C. and incubated for 8 minutes. This was followed by another application of Cell Conditioner #2 and incubation at 90° C. for 12 minutes. The slide was rinsed with Reaction Buffer (VMSI), cooled to 37° C. and ISH-Protease 3 (100 µL, VMSI) was added. After an incubation of 4 minutes, the slide was rinsed three times before the application of iView+HybReady (200 µL, VMSI) which was incubated for 4 minutes. Addition of HPV HR Probe (200 µL VMSI) was followed by an incubation of 4 minutes at 37° C., 12 minutes at 95° C. and 124 minutes at 52° C. The slide was then rinsed twice and warmed to 72° C. This last step was repeated two more times before cooling the slide down to 37° C. and adding iView+Anti-DNP (100 µL, VMSI). The primary antibody was incubated for 20 minutes and the slide was then rinsed twice before the manual addition of the polyacrylamide hydrazide biotinylated secondary (goat anti-rabbit, 100 µL, 10 µg/ml). Incubation of the secondary occurred for 20 minutes and the slide twice. The anti-hapten antibody was then applied (100 µL) and incubation occurred for another 20 minutes. After two more rinse steps, the goat anti-rabbit AP conjugate was applied (100 µL, 6 µg/ml) and incubated for 8 minutes. Four more rinse steps were followed by the application of the iView+Enhancer (100 µL, VMSI) which was followed by incubation for 4 minutes and application of both iView+NBT (100 µL, VMSI) and iView+BCIP (100 µL, VMSI). The slide was then incubated for a period of 24 minutes, rinsed three times, and Counterstain NFR (100 µL, VMSI) was added. After incubation with the counterstain for 4 minutes, the slide was rinsed three more times and taken off of the instrument. The slide was treated to a detergent wash before dehydration with ethanol, acetone and xylene and subsequent application of a cover slip to the slide, after which the slide was viewed through a microscope.

Example 12

Figure 13:
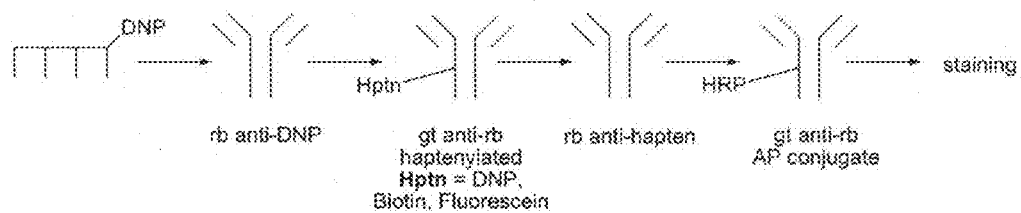
FIG. 13 illustrates one embodiment of a staining protocol for HPV SISH detection.
Figure 14:
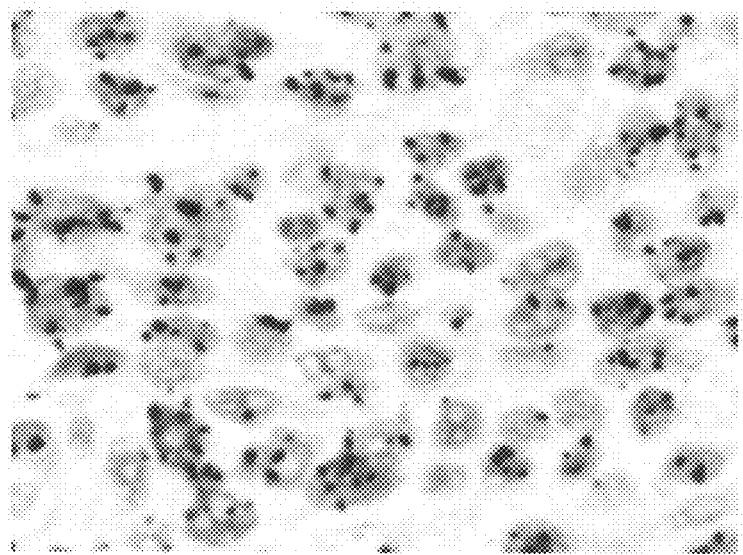
FIG. 14 is a photograph illustrating staining of HPV on xenographed tissue by silver detection (40× magnification) using an Fc-specific biotinylated goat anti-rabbit antibody on CaSki cells (400-600 copies).
Figure 15:
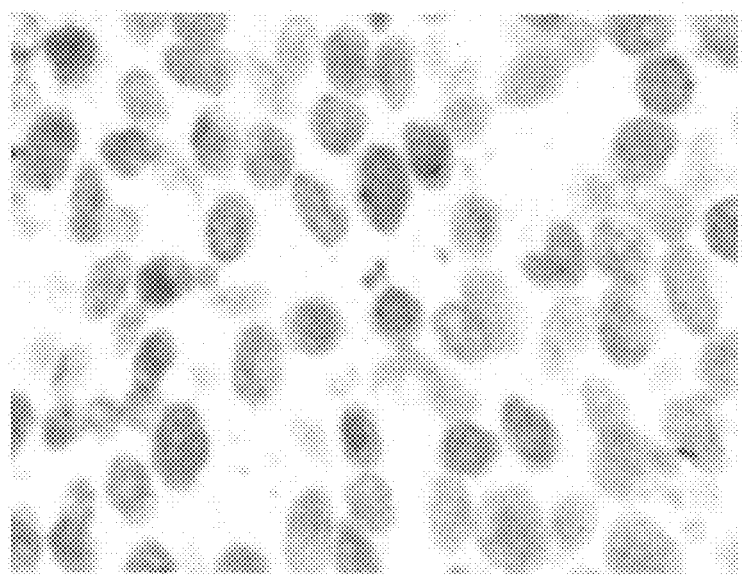
FIG. 15 is a photograph illustrating staining of HPV on xenographed tissue by silver detection (40× magnification) using an Fc-specific biotinylated goat anti-rabbit antibody on HeLa cells (10-50 copies).
Figure 16:
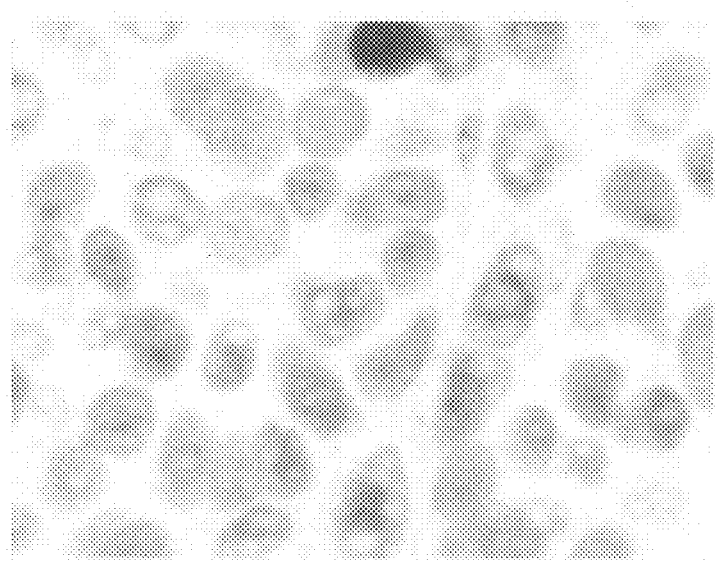
FIG. 16 is a photograph illustrating staining of HPV on xenographed tissue (40× magnification) biotinylated goat anti-rabbit antibody on SiHa cells (1-2 copies), Fc-specific biotinylated antibody.
Figure 17:
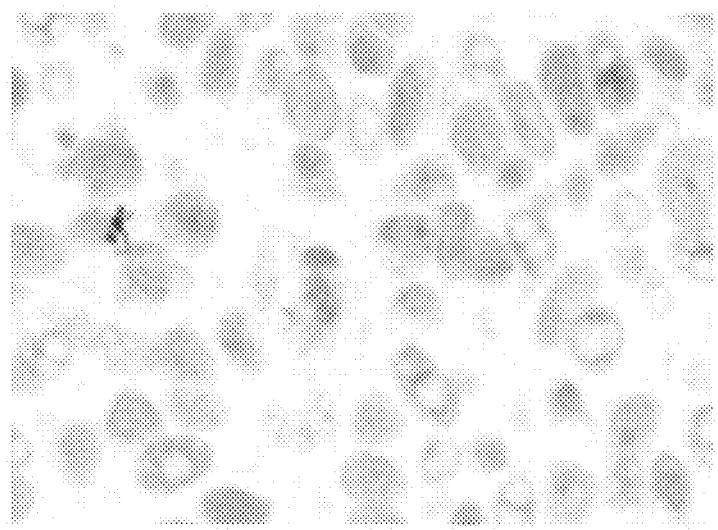
FIG. 17 is a photograph illustrating staining of HPV on xenographed tissue by silver detection (40× magnification) using an Fc-specific biotinylated goat anti-rabbit antibody on C33 cells (0 copies, negative control).
Figure 18:
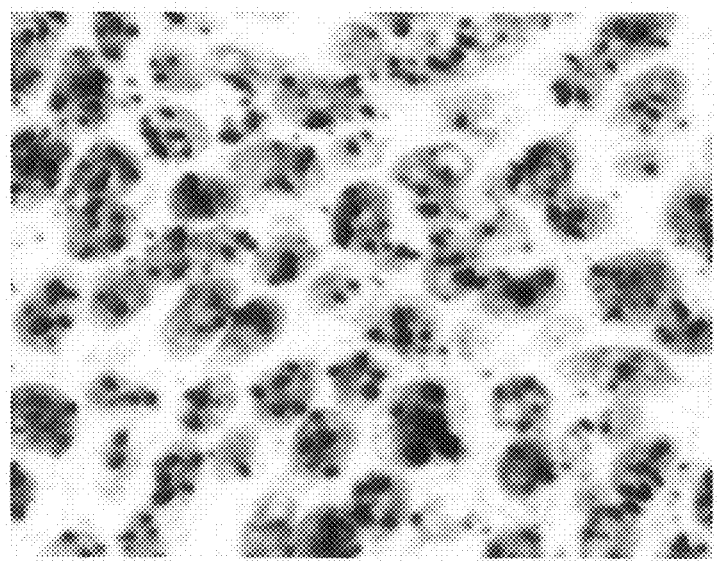
FIG. 18 is a photograph illustrating staining of HPV on xenographed tissue by silver detection (40× magnification) using a polyacrylamide hydrazide biotinylated goat anti-rabbit antibody on CaSki cells (400-600 copies).
Figure 19:
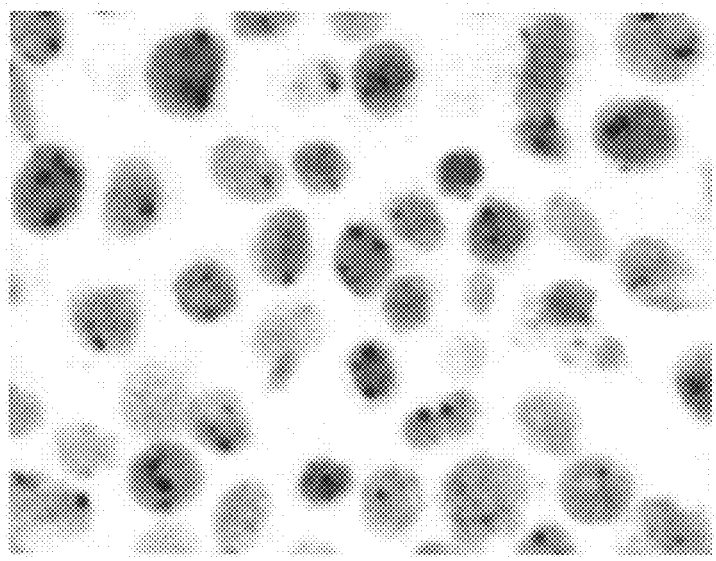
FIG. 19 is a photograph illustrating staining of HPV on xenographed tissue by silver detection (40× magnification) using a polyacrylamide hydrazide biotinylated goat anti-rabbit antibody on HeLa cells (10-50 copies).
Figure 20:
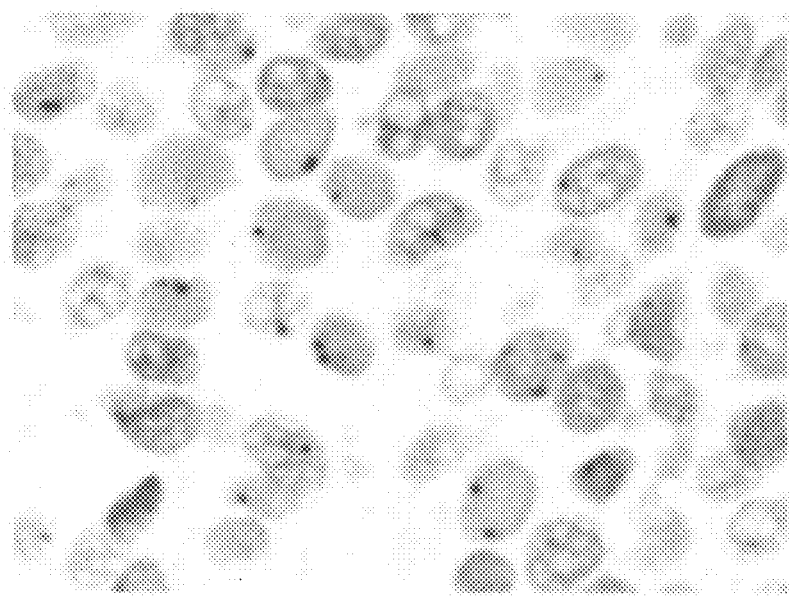
FIG. 20 is a photograph illustrating staining of HPV on xenographed tissue by silver detection (40× magnification) using a polyacrylamide hydrazide biotinylated goat anti-rabbit antibody on SiHa cells (1-2 copies).
Figure 21:
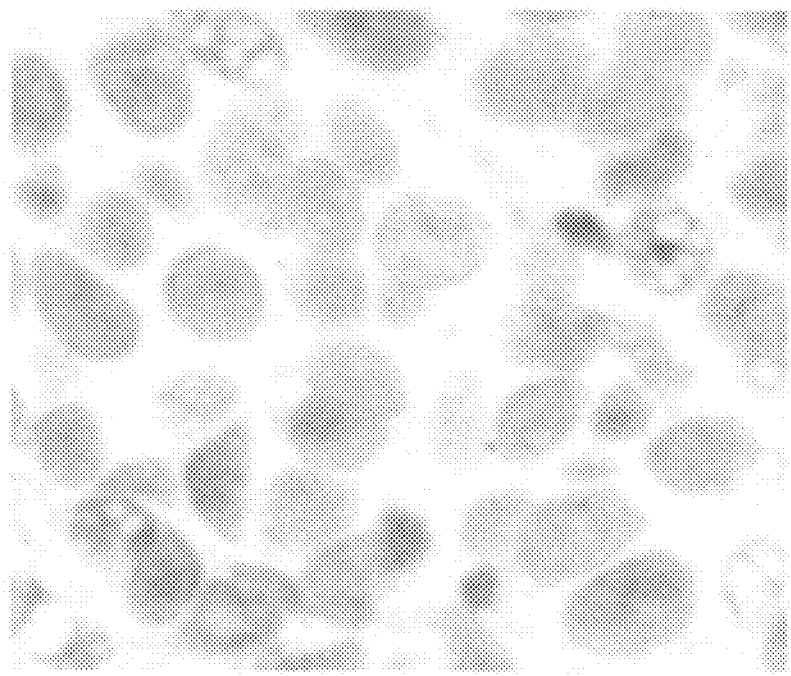
FIG. 21 is a photograph illustrating staining of HPV on xenographed tissue by silver detection (40× magnification) using a polyacrylamide hydrazide biotinylated goat anti-rabbit antibody on C33 cells (0 copies, negative control).

This example concerns evaluating horseradish peroxidase-antibody multimeric conjugates, particularly evaluation of HPV in different tissues using Fc-conjugated biotin-hydrazide or biotinylated polyacrylamide hydrazide for SISH detection as depicted in FIG. 13. The following is an adapted procedure from the Ventana Benchmark Instrument: the paraffin coated tissue on the slide was heated to 75° C. for 4 minutes and treated twice with EZPrep volume adjust (VMS 1) at 75° C. before application of the liquid cover slip (VMSI) with EZPrep volume adjust. After 4 minutes at 75° C., the slide was rinsed and EZPrep volume adjust was added along with liquid cover slip to deparaffin the tissue at 76° C. for 4 minutes. Cell Conditioner #2 (VMSI) was added, the slide warmed to 90° C., and incubated for 8 minutes. This was followed by another application of Cell Conditioner #2 and incubation at 90° C. for 12 minutes. The slide was rinsed with Reaction Buffer (VMSI), cooled to 37° C. and ISH-Protease 3 (100 µL, VMSI) was added. After an incubation of 4 minutes, the slide was rinsed three times before the application of iView+HybReady (100 µL, VMSI) which was incubated for 4 minutes. Addition of HPV HR Probe (200 µL VMSI) was followed by an incubation of 4 minutes at 37° C., 12 minutes at 95° C. and 124 minutes at 52° C. The slide was then rinsed twice and warmed to 72° C. This last step was repeated two more times before cooling the slide down to 37° C. and adding iView+Anti-DNP (100 µL, VMSI). The primary antibody was incubated for 20 minutes and the slide was then rinsed twice before the manual addition of the polyacrylamide hydrazide-biotinylated secondary (goat anti-rabbit, 100 µL, 10 µg/ml). Incubation of the secondary occurred for 8 minutes and the slide twice. The rabbit anti-biotin antibody was then applied (100 µL) and incubation occurred for another 20 minutes. After two more rinse steps, the HRP multimer was applied (100 µL, 10 µg/ml) and incubated for 8 minutes. Four more rinse steps were followed by the application of the SISH Chromagen A (100 µL VMSI) with a 4 minute incubation, SISH Chromagen B (100 µL, VMSI) with a 4 minute incubation, and SISH Chromagen C (100 µL, VMSI) with a 4 minute incubation. The slide was rinsed three times, and Hematoxylin II (100 µL, VMSI) was added. After incubation with the counterstain for 4 minutes, the slide was rinsed and Bluing Reagent (100 µL, VMSI) was applied and incubated for 4 minutes. The slide was then rinsed three more times and taken off of the instrument. The slide was treated to a detergent wash before dehydration with ethanol, acetone and xylene and subsequent application of a cover slip to the slide, after which the slide was viewed through a microscope. FIGS. 14-21 illustrate staining results obtained according to this example.

Example 13

Figure 22:
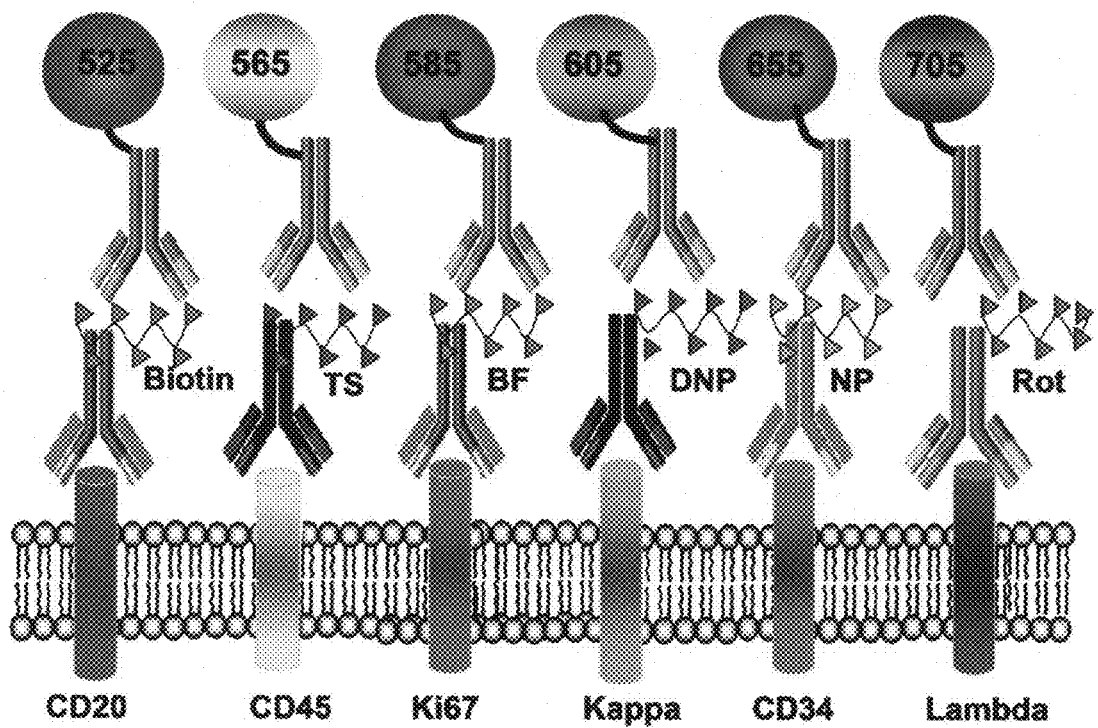
FIG. 22 illustrates one embodiment of a staining protocol for multiplex IHC detection with quantum dots.
Figure 23:
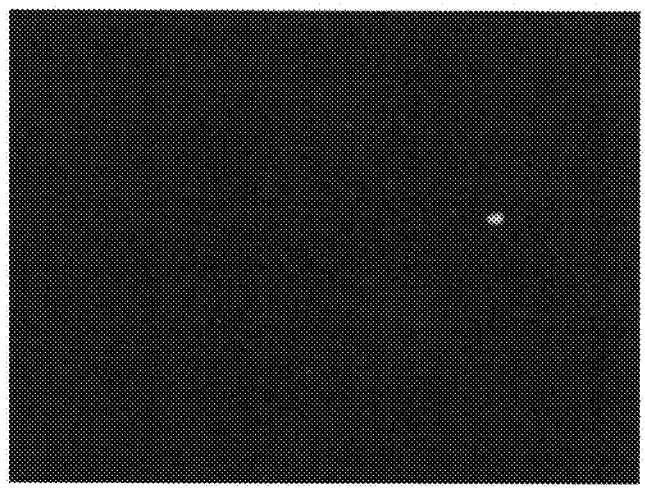
FIG. 23 is a photograph illustrating staining of tonsil tissue (Long Pass filter, Omega Optical XFO5-2; 40× magnification) using an anti-nitropyrazole-quantum dot 655 conjugate with an anti-CD34 polyacrylamide hydrazide nitropyrazole conjugate.
Figure 24:
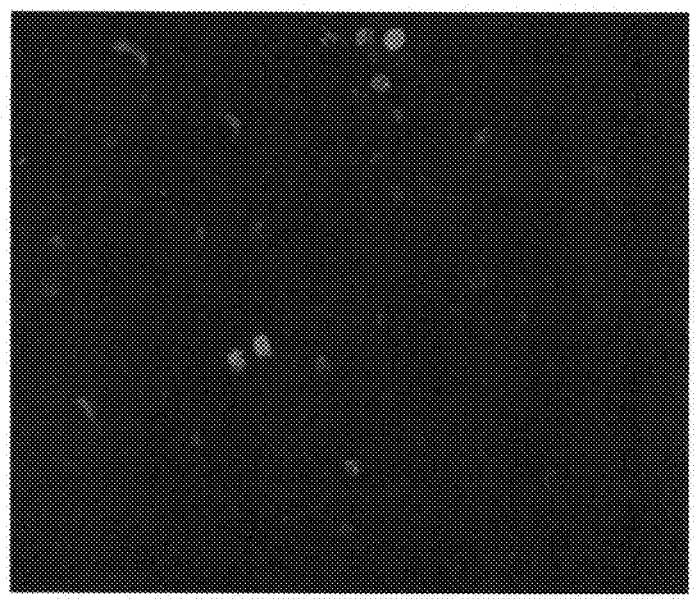
FIG. 24 is a photograph illustrating staining of tonsil tissue (Long Pass filter, Omega Optical XFO5-2; 40× magnification) using an anti-benzofurazan-quantum dot 585 conjugate with an anti-Ki67 polyacrylamide hydrazide benzofurazan conjugate.
Figure 25:
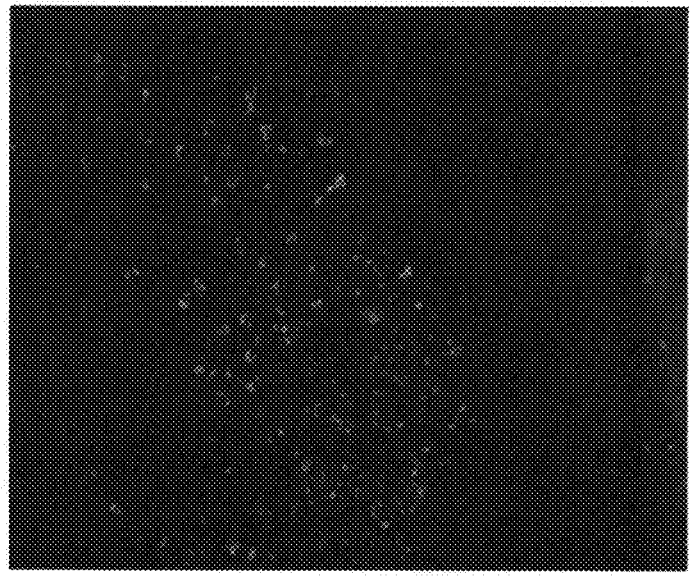
FIG. 25 is a photograph illustrating staining of tonsil tissue (Long Pass filter, Omega Optical XFO5-2; 40× magnification) using an anti-dinitrophenyl-quantum dot 605 conjugate with an anti-kappa polyacrylamide hydrazide dinitrophenyl conjugate.
Figure 26:
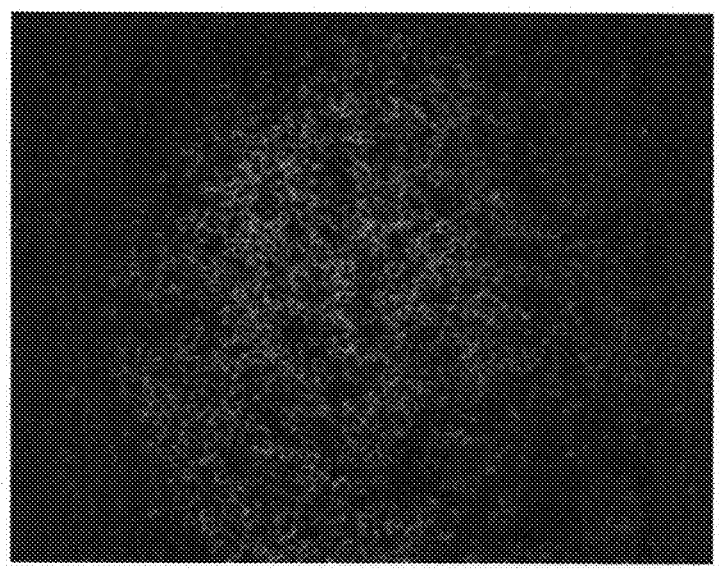
FIG. 26 is a photograph illustrating staining of tonsil tissue (Long Pass filter, Omega Optical XFO5-2; 40× magnification) using an anti-thiazolesulfonamide-quantum dot 565 conjugate with an anti-CD45 polyacrylamide hydrazide thiazolesulfonamide conjugate.

This example illustrates the multiplexed detection of anti-Kappa, CD34, CD45 and Ki-67 on tonsil with quantum dots as depicted generally in FIG. 22. The procedure is an adaptation the automated staining protocol from the Ventana Benchmark Instrument. The paraffin coated tissue on the slide was heated to 75° C. for 8 minutes and treated twice with EZPrep (VMSI), volume adjusted at 75° C. before application of the liquid cover slip (VMSI). After two 8 minute incubation times at 75° C., the slide was rinsed and EZPrep volume adjusted, followed with liquid coverslip to deparaffinize the tissue. The slide was cooled to 37° C., incubated for 2 minutes and rinsed once with reaction buffer. The slide was then treated with cell conditioner twice, followed by liquid coverslip. The slide is heated to 95° C. for 8 minutes, followed by coverslip, then is heated to 100° C. for 4 minutes, followed by coverslip. "Apply cell conditioner, incubate for 4 minutes, apply coverslip", this incubation process with cell conditioner was repeated 9 times at 100° C. Slide was cooled down for 8 minutes, rinsed with reaction buffer, volume adjust, followed by liquid coverslip. The slide is heated to 37° C. for 2 minutes and rinsed two times before the addition of the primary conjugates (anti-Kappa-PAH-dPEG$_8$-dinitrophenyl, —CD34-PAH-dPEG$_8$-nitropyrazole, —CD45-PAH-dPEG$_8$-thiosulfonamide and Ki-67-PAH-dPEG$_8$-benzofuran, 100 µL of each, VMSI) followed by liquid cover slip and incubation at 37° C. for 32 minutes. The slide was rinsed twice with reaction buffer and the appropriate cocktail of anti-hapten Ab-Quantum Dot conjugates (100 µL each, 20-50 nmol) followed by the application of liquid cover slip and incubated at 37° C. for 32 minutes. The slide was rinsed two times with buffer followed by liquid coverslip. The slide is removed from the instrument and treated with a detergent wash before manual application of a cover slip. The slide image was captured by using a CRI Imaging camera on a fluorescent microscope with a long-pass filter and image enhancement software (Acquity). FIGS. 23-26 illustrate staining results obtained according to this example.

Example 14

This example concerns the synthesis of dextran hydrazide, dextran hydrazines, dextran amines, and dextran guanidines. DextranAldehydes (Pierce) average MW 10,000, 20,000 or 40,000 containing between 10 to 200 aldehydes are dissolved in phosphate buffer pH 7.0.

Corresponding bis-PEG$_x$-amine, bis-hydrazide PEG$_x$-hydrazide, bis-PEG$_x$-hydrazine or guanidine-containing linker e.g. aminoguanidine (Aldrich), are added as a buffered pH 7.0 solution in very large molar excess (100× with the aldehyde content the limiting reagent on the dextran carrier).

The reaction is stirred at room temperature for 1-3 hours. A large excess (300× of the reducing agent e.g. sodium cyanoborohydride, Aldrich) is added as an aqueous solution from an addition funnel, over a period of 2 hours.

Reaction solutions are stirred overnight and then dialyzed against water several times, utilizing an appropriate dialysis tubing which will allow diffusion of the smaller MW molecules and retaining the large derivatized carrier.

The dialyzed solutions of the carriers are lyophilized and stored at 2-8° C. as desiccated powders. The number of amines, hydrazines, guanidines or hydrazides may be quantitated according to the methods described in the literature.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

Example 15

This example describes one embodiment of a method for making polyvinylpyrrolidone hydrazide (PVPH). Polyvinylpyrrolidone (1 mmol, 20 mL, 50 wt % solution, Sigma-Aldrich) was mixed with hydrazine monohydrate (50 mL, 1.0 mol, Sigma-Aldrich) in a 100 mL round-bottom flask fitted with a condenser. The reaction mixture was microwaved in a CEM Discovery unit for 60 minutes at 120° C. at various powers (100 W, 200 W, 300 W). The reaction was reduced in vacuo to an off-white foam. The residue was taken up in a minimal amount of DI water and mixed with a large volume of tetrahydrofuran (THF) to induce precipitation. The resulting mixture was centrifuged and decanted. The residue was taken up in a minimal amount of deionized water, and the precipitation process with THF repeated for a total of three times. The final residue was dissolved in deionized water and lyophilized to give a fine, off-white hygroscopic powder.

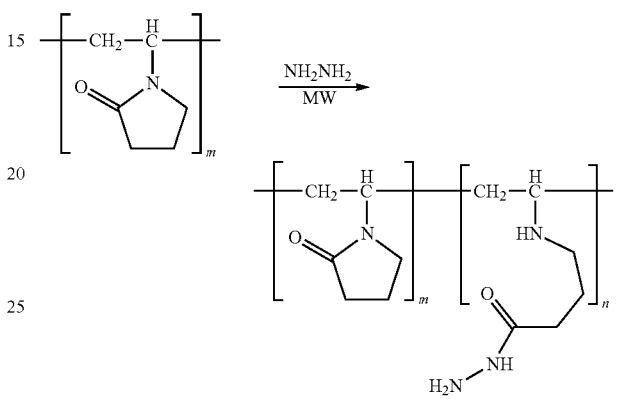

Example 16

This example describes one embodiment of a method for making polyisobuytlene-co-maleic hydrazide (PIBMH). Polyisobutylene-co-maleic anhydride (7.1 mmol, 1.09 g, Sigma-Aldrich) was mixed with hydrazine monohydrate (7.0 mL, 144 mmol, Sigma-Aldrich) in a 10 mL CEM microwave tube. The reaction mixture was microwaved in a CEM Discovery unit for 60 minutes at 120° C. at 300 W. The reaction was reduced in vacuo to an off-white foam. The residue was taken up in a minimal amount of DI water and mixed with a large volume of ethanol to induce precipitation. The resulting mixture was centrifuged and decanted. The residue was taken up in a minimal amount of deionized water, and the precipitation process with ethanol repeated for a total of three times. The final residue was dissolved in deionized water and lyophilized to give a fine, off-white hygroscopic powder.

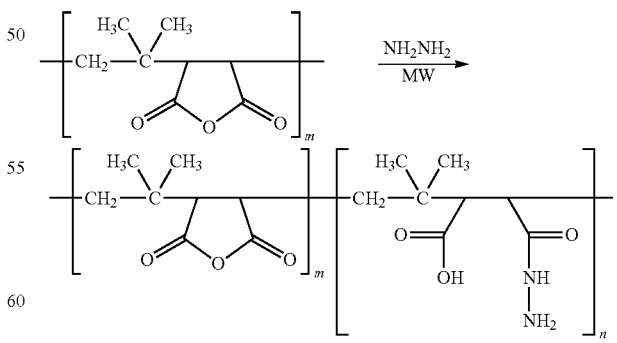

Example 17

This example describes one embodiment of a method for making polyacrylic acid hydrazide (PAAH). Polyacrylic acid (9.57 mmol, 2.00 g, 45% wt solution in water, Sigma-Aldrich) was diluted with 40 mL DI water and reacted with t-butyl carbazate (9.57 mmol, 1.24 g, Sigma-Aldrich) and EDAC (19.1 mmol, 3.66 g) at room temperature for 14 hours. The reaction mixture pH was adjusted to <3 by dropwise addition of 1M HCl to induce precipitation of the polymer. The polymer precipitate was filtered, washed with DI water and vacuum dried to produce 846 mg of material. The BOC-protected polymer was stirred in trifluoroacetic acid (8 mL) until completely dissolved over one hour and the TFA removed in vacuo. The residual TFA was removed by azeotropic distillation with toluene, followed by methylene chloride, and further dried under reduced pressure to give 720 mg of a white solid.

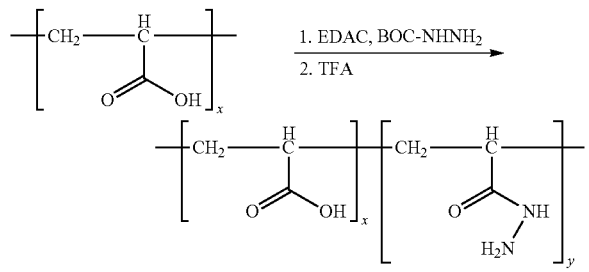

Example 18

This example describes the method for determining the molar equivalents of reactive hydrazide groups per polymer by fluorescence. A standard curve was generated by reacting six concentrations (0.1 to 0.8 mM) of acetylhydrazide with fluorescamine in PBS, pH 7.5 and plotting the fluorescence (A360/E460) vs. concentration. The $R^2$ value was 0.994 for the standard curve.

Polyacrylamide, polyisobutylene-co-maleic anhydride, polyvinylpyrrolidone, and polyacrylic acid were used as negative controls for hydrazide incorporation in polyacrylamide hydrazide, polyvinylpyrrolidone hydrazide, polyisobutylene-co-maleic hydrazide and polyacrylic acid hydrazide as synthesized from Examples 1, 15, 16 and 17, respectively. Each polymer was dissolved in PBS, pH 7.5 to a known concentration, reacted with fluorescamine, and the fluorescence measured at 460 nm. The number of reactive hydrazides was calculated compared to the standard curve and adjusted for the average molecular weight of the individual polymers.

Hydrazide incorporation was highest for polyacrylamide, but polyisobutylene-co-maleic anhydride and polyvinylpyrrolidone produced functionalized polymer. Using additional microwave energy did not appear to significantly increase hydrazide functionalization as demonstrated in Table 2. The non-microwave-mediated incorporation of hydrazine in polyacrylic acid produced higher hydrazide incorporation than either polyisobutylene-co-maleic anhydride or polyvinylpyrrolidone, but lesser incorporation than polyacrylamide.

TABLE 1

Polymer Hydrazide Incorporation

| Polymer | Molar Equivalents of Hydrazides |
| --- | --- |
| Polyacrylamide | 0.0 |
| Polyacrylamide hydrazide | 76 |

TABLE 1-continued

Polymer Hydrazide Incorporation

| Polymer | Molar Equivalents of Hydrazides |
| --- | --- |
| Polyisobutylene-co-maleic anhydride | 0.0 |
| Polyisobutylene-co-maleic hydrazide | 38 |
| Polyvinylpyrrolidone | 4.7 |
| Polyvinylpyrrolidone hydrazide | 30 |
| Polyacrylic acid | 0.0 |
| Polyacrylic acid hydrazide | 53 |

TABLE 2

Polymer Hydrazide Incorporation by Microwave Power

| Polymer | Molar Equivalents of Hydrazides |
| --- | --- |
| Polyvinylpyrrolidone | 4.7 |
| Polyvinylpyrrolidone hydrazide (100 W) | 33 |
| Polyvinylpyrrolidone hydrazide (200 W) | 34 |
| Polyvinylpyrrolidone hydrazide (300 W) | 30 |

Example 19

This example describes one embodiment of a method for synthesizing a chemoselective Fc-specific polyvinylpyrrolidone hydrazide-antibody (PVPH-Ab) conjugate as illustrated generally in FIG. 2. A solution of a polyclonal antibody (0.8 mL of 1.0 mg/mL) was incubated with a 100 mM aqueous solution of sodium periodate (0.2 ml) for two hours at room temperature. The solution was buffer exchanged by passing through a column of G-25 (GE Lifesciences, PD-10 column) using ABS (0.10 M acetate, 0.15M NaCl, pH 5.5). PVPH was added to the oxidized Ab using a 50-fold molar excess to the Ab and incubated at room temperature overnight. The PVPH-Ab was purified on a size exclusion column using ABS (0.10 M acetate, 0.15M NaCl, pH 5.5). The NHS-dPEG$_8$-DNP (50× molar excess) was added and the reaction was incubated for a period of 18 hours. SEC (0.1 M phosphate, 0.15 M NaCl, pH=7.5) resulted in the purified polyhaptenylated antibody. The number of haptens per antibody was calculated using UV-Vis measurements.

Example 20

This example describes one embodiment of a method for synthesizing a chemoselective Fc-specific polyisobutylene-co-maleic hydrazide-antibody (PIBM-Ab) conjugate as illustrated generally in FIG. 2. A solution of a polyclonal antibody (0.8 mL of 1.0 mg/mL) was incubated with a 100 mM aqueous solution of sodium periodate (0.2 ml) for two hours at room temperature. The solution was buffer exchanged by passing through a column of G-25 (GE Lifesciences, PD-10 column) using ABS (0.10 M acetate, 0.15M NaCl, pH 5.5). PVPH was added to the oxidized Ab using a 50-fold molar excess to the Ab and incubated at room temperature overnight. The PIBMH-Ab was purified on a size exclusion column using ABS (0.10 M acetate, 0.15M NaCl, pH 5.5). The NHS-dPEG$_8$-DNP (50× molar excess) was added and the reaction was incubated for a period of 18 hours. SEC (0.1 M phosphate, 0.15 M NaCl, pH=7.5) resulted in the purified polyhaptenylated antibody. The number of haptens per antibody was calculated using UV-Vis measurements.

Example 21

This example describes one embodiment of a method for synthesizing a chemoselective Fc-specific polyacrylic acid hydrazide-antibody (PAAH-Ab) conjugate as illustrated generally in FIG. 2. A solution of a polyclonal antibody (0.8 mL of 1.0 mg/mL) was incubated with a 100 mM aqueous solution of sodium periodate (0.2 ml) for two hours at room temperature. The solution was buffer exchanged by passing through a column of G-25 (GE Lifesciences, PD-10 column) using ABS (0.10 M acetate, 0.15M NaCl, pH 5.5). PAAH was added to the oxidized Ab using a 50-fold molar excess to the Ab and incubated at room temperature overnight. The PAAH-Ab was purified on a size exclusion column using ABS (0.10 M acetate, 0.15M NaCl, pH 5.5). The NHS-dPEG$_8$-DNP (50× molar excess) was added and the reaction was incubated for a period of 18 hours. SEC (0.1 M phosphate, 0.15 M NaCl, pH=7.5) resulted in the purified polyhaptenylated antibody. The number of haptens per antibody was calculated using UV-Vis measurements.

Example 22

Figure 27:
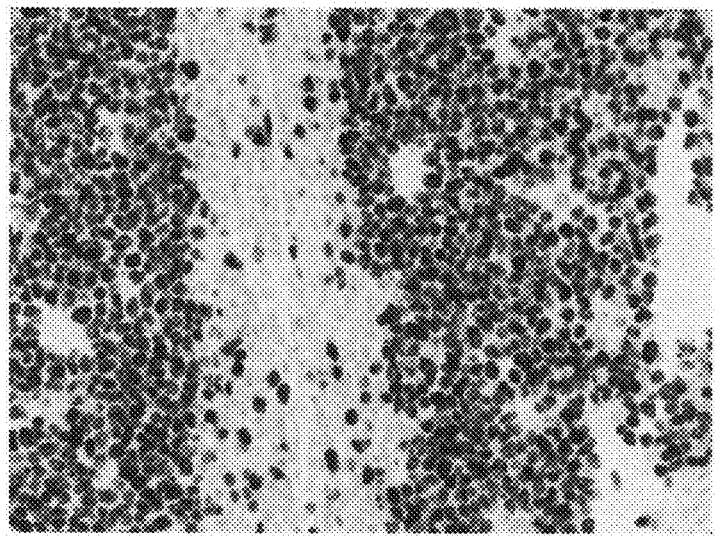
FIG. 27 is a photograph illustrating staining of tonsil tissue (Olympus DP71; UPlanSApo; 40× magnification) using an anti-dinitrophenyl-HRP conjugate/DAB with an anti-kappa polyvinylpyrrolidone hydrazide dinitrophenyl conjugate.
Figure 28:
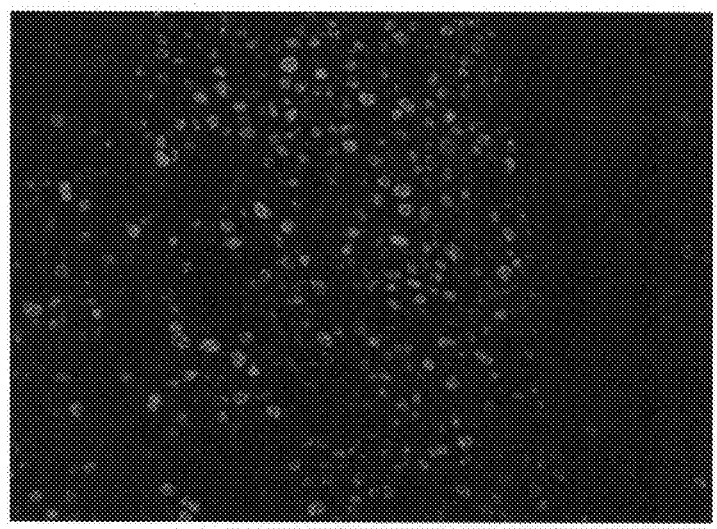
FIG. 28 is a photograph illustrating staining of tonsil tissue (Long Pass filter, Omega Optical XFO5-2; 40× magnification) using an anti-dinitrophenyl-quantum dot 655 conjugate with an anti-kappa polyvinylpyrrolidone hydrazide dinitrophenyl conjugate.

This example concerns detecting tissue epitopes, particularly Ki-67 on tonsil, using either chromogenic staining (i.e. HRP-mediated deposition of DAB) or quantum dots to recognize an antibody conjugated with a polyhaptenylated polymer. The following is the adapted procedure from the Ventana Benchmark Instrument. The paraffin-coated tissue on the slide was heated to 75° C. for 4 minutes and treated twice with EZPrep volume adjust (VMSI) at 75° C. before application of the liquid cover slip (VMSI) with EZPrep volume adjust. After 4 minutes at 75° C., the slide was rinsed and EZPrep volume adjust was added along with liquid cover slip to deparaffin the tissue at 76° C. for 4 minutes. The slide was cooled to 40° C. and rinsed three times before the addition of a mouse anti-Ki67 (100 μL, VMSI) antibody followed by liquid cover slip and incubation at 40° C. for 16 minutes. After rinsing the slide, the tissue was treated with a goat anti-mouse-PVPH-DNP antibody (100 μL) followed by liquid cover slip and incubation at 40° C. for 8 minutes. The slide was rinsed twice with buffer followed by the application of liquid cover slip and the addition of 655 nm QDot:anti-DNP MAb conjugate (100 μL, 20 nmol) and incubation at 37° C. for 16 minutes. The slide was rinsed three times with buffer and treated to a detergent wash before manual application of a cover slip to the slide, after which the slide was viewed through a microscope. FIGS. 27 and 28 illustrate staining results obtained according to this example.

Example 23

Figure 29:
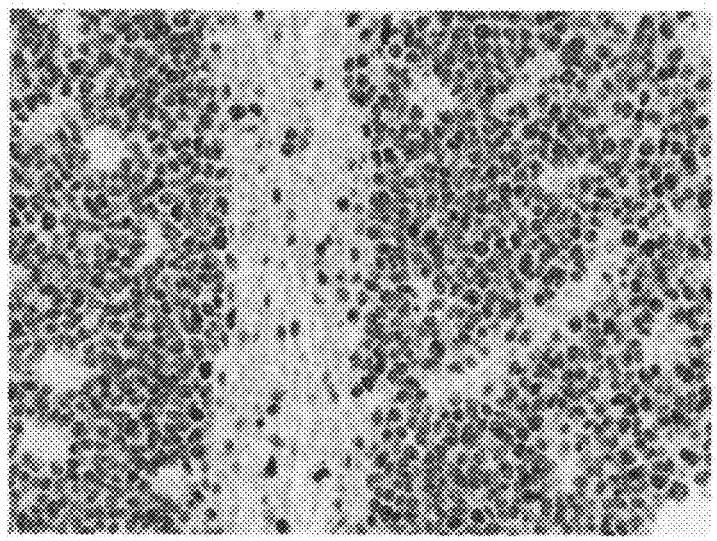
FIG. 29 is a photograph illustrating staining of tonsil tissue (Olympus DP71; UPlanSApo; 40× magnification) using an anti-dinitrophenyl-HRP conjugate/DAB with an anti-kappa polyisobutylene-co-maleic hydrazide dinitrophenyl conjugate.
Figure 30:
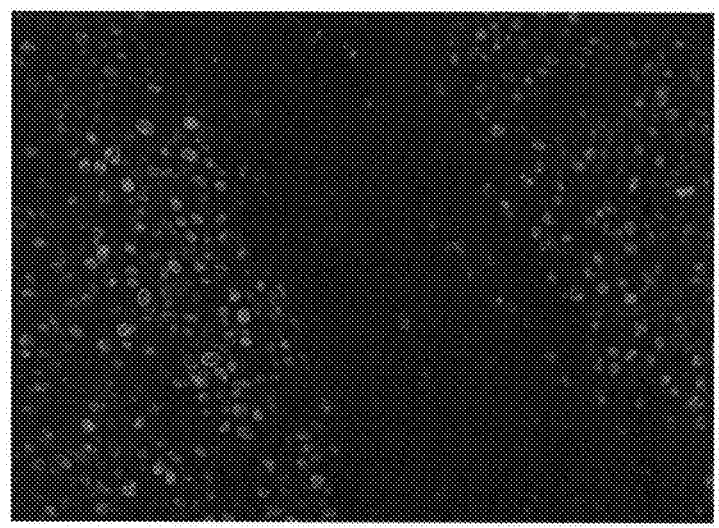
FIG. 30 is a photograph illustrating staining of tonsil tissue (Long Pass filter, Omega Optical XFO5-2; 40× magnification) using an anti-dinitrophenyl-quantum dot 655 conjugate with an anti-kappa polyisobutylene-co-maleic hydrazide dinitrophenyl conjugate.

This example concerns detecting tissue epitopes, particularly Ki-67 on tonsil, using either chromogenic staining (i.e. HRP-mediated deposition of DAB) or quantum dots to recognize an antibody conjugated with a polyhaptenylated polymer. The following is the adapted procedure from the Ventana Benchmark Instrument. The paraffin-coated tissue on the slide was heated to 75° C. for 4 minutes and treated twice with EZPrep volume adjust (VMSI) at 75° C. before application of the liquid cover slip (VMSI) with EZPrep volume adjust. After 4 minutes at 75° C., the slide was rinsed and EZPrep volume adjust was added along with liquid cover slip to deparaffin the tissue at 76° C. for 4 minutes. The slide was cooled to 40° C. and rinsed three times before the addition of a mouse anti-Ki67 (100 μL, VMSI) antibody followed by liquid cover slip and incubation at 40° C. for 16 minutes. After rinsing the slide, the tissue was treated with a goat anti-mouse-PIBMH-DNP antibody (100 μL) followed by liquid cover slip and incubation at 40° C. for 8 minutes. The slide was rinsed twice with buffer followed by the application of liquid cover slip and the addition of 655 nm QDot:anti-DNP MAb conjugate (100 μL, 20 nmol) and incubation at 37° C. for 16 minutes. The slide was rinsed three times with buffer and treated to a detergent wash before manual application of a cover slip to the slide, after which the slide was viewed through a microscope. FIGS. 29 and 30 illustrate staining results obtained according to this example.

Example 24

Figure 31:
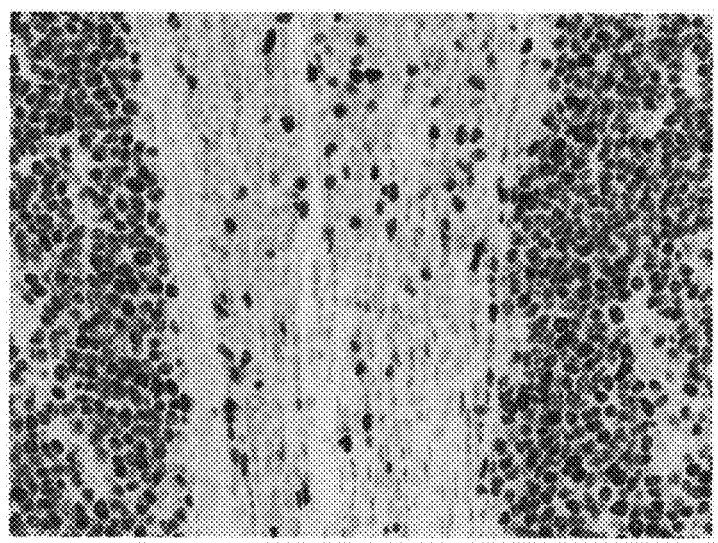
FIG. 31 is a photograph illustrating staining of tonsil tissue (Olympus DP71; UPlanSApo; 40× magnification) using an anti-dinitrophenyl-HRP conjugate/DAB with an anti-kappa polyacrylic acid hydrazide dinitrophenyl conjugate.
Figure 32:
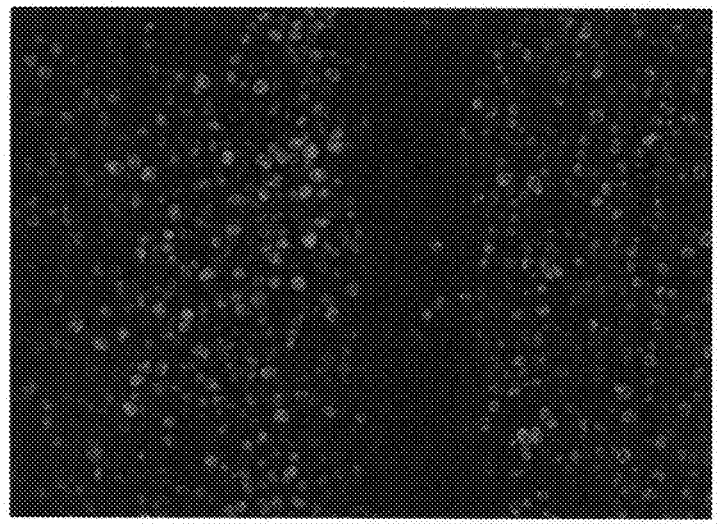
FIG. 32 is a photograph illustrating staining of tonsil tissue (Long Pass filter, Omega Optical XFO5-2; 40× magnification) using an anti-dinitrophenyl-quantum dot 655 conjugate with an anti-kappa polyacrylic acid hydrazide dinitrophenyl conjugate.

This example concerns detecting tissue epitopes, particularly Ki-67 on tonsil, using either chromogenic staining (i.e. HRP-mediated deposition of DAB) or quantum dots to recognize an antibody conjugated with a polyhaptenylated polymer. The following is the adapted procedure from the Ventana Benchmark Instrument. The paraffin-coated tissue on the slide was heated to 75° C. for 4 minutes and treated twice with EZPrep volume adjust (VMSI) at 75° C. before application of the liquid cover slip (VMSI) with EZPrep volume adjust. After 4 minutes at 75° C., the slide was rinsed and EZPrep volume adjust was added along with liquid cover slip to deparaffin the tissue at 76° C. for 4 minutes. The slide was cooled to 40° C. and rinsed three times before the addition of a mouse anti-Ki67 (100 μL, VMSI) antibody followed by liquid cover slip and incubation at 40° C. for 16 minutes. After rinsing the slide, the tissue was treated with a goat anti-mouse-PAAH-DNP antibody (100 μL) followed by liquid cover slip and incubation at 40° C. for 8 minutes. The slide was rinsed twice with buffer followed by the application of liquid cover slip and the addition of 655 nm QDot:anti-DNP MAb conjugate (100 μL, 20 nmol) and incubation at 37° C. for 16 minutes. The slide was rinsed three times with buffer and treated to a detergent wash before manual application of a cover slip to the slide, after which the slide was viewed through a microscope. FIGS. 31 and 32 illustrate staining results obtained according to this example.

The present application has been described with reference to certain particular embodiments. A person of ordinary skill in the art will appreciate that the scope of the invention is not limited to those particular embodiments.

We claim:

1. A conjugate, comprising:
   an antibody covalently bonded to a detectable label molecule through a reactive functional group provided by a polymeric carrier other than a polyacrylamide hydrazide thiol, the polymeric carrier comprising plural reactive functional groups selected from hydrazines, hydrazides, hydrazine derivatives, hydrazide derivatives, guanidines, aminoguanidines, hydroxyl amines, or combinations thereof, wherein the polymeric carrier is directly coupled to an oxidized Fc portion of the antibody; and
   a molecule, other than the antibody and the detectable label molecule, bonded to the polymeric carrier through at least one reactive functional group.

2. The conjugate according to claim 1 where the polymeric carrier comprises a polymeric portion selected from polyacrylamide, polyacrylamide-N-hydroxysuccinimides, polyacrylic acids, polyethyleneimines, polysaccharides, polyethylene-alt-maleic acids, polyamino acids or polyvinylpyrrolidones, the polymeric portion including plural reactive functional groups selected from hydrazines, hydrazides, hydrazine derivatives, hydrazide derivatives, guanidines, aminoguanidines, hydroxyl amines, or combinations thereof.

3. The conjugate according to claim 1 where the polymeric carrier comprises a polyacrylamide or polyvinylpyrrolidone portion.

4. The conjugate according to claim 1 where the polymeric carrier is a PEG-based hydrazide linker.

5. The conjugate according to claim 1 where the detectable label molecule is an enzyme, a fluorophore, a luminophore, a hapten, a fluorescent nanoparticle, or combinations thereof.

6. The conjugate according to claim 1 where the detectable label molecule is a hapten selected from di-nitrophenyl, biotin, digoxigenin, fluorescein, rhodamine, bromodeoxyuridine, mouse immunoglobulin, or combinations thereof.

7. The conjugate according to claim 1 where the detectable label molecule is a hapten selected from oxazoles, pyrazoles, thiazoles, benzofurazans, triterpenes, ureas, thioureas, nitroaryls other than dinitrophenyl, rotenoids, coumarins, cyclolignans, heterobiaryls, azoaryls, benzodiazepines, or combinations thereof.

8. The conjugate according to claim 1 where the polymeric carrier is a polyacrylamide hydrazide, having plural hydrazide functional groups, that is coupled to the oxidized Fc portion of the antibody and to at least one detectable label molecule through hydrazide groups.

9. The conjugate according to claim 1 comprising plural hapten molecules coupled to the polymeric carrier.

10. The conjugate according to claim 2 where the polysaccharide is selected from carbohydrates, cellulose, carboxymethylcellulose, dextran, amido dextrans, hydrazide dextrans, hydrazine dextrans, glycogen, polyhyaluronic acid, starch, or combinations thereof.

11. The conjugate according to claim 2 where the polyamino acid is selected from poly(aspargine), poly(aspartic acid), poly(glutamic acid), poly(glutamine), poly(lysine), poly(guanidines), or combinations thereof.

12. A method for forming a molecular conjugate, comprising reacting a polymeric carrier comprising plural reactive functional groups selected from hydrazines, hydrazides, hydrazine derivatives, hydrazide derivatives, guanidines, aminoguanidines, hydroxyl amines, or combinations thereof, with an antibody, a detectable label molecule, and a molecule, other than the antibody or the detectable label molecule, wherein the polymeric carrier is other than a polyacrylamide hydrazide thiol and is directly coupled to an oxidized Fc portion of the antibody through at least one reactive functional group.

13. The method according to claim 12 where the polymeric carrier comprises a polymeric portion selected from polyacrylamide, polyacrylamide-N-hydroxysuccinimides, polyacrylic acids, polyethyleneimines, polysaccharides, polyethylene-alt-maleic acids, polyamino acids or polyvinylpyrrolidones.

14. The method according to claim 12 where the polymeric carrier is polyacrylamide hydrazide or polyvinylpyrrolidone hydrazide.

15. The method according to claim 12 where the polymeric carrier is a polyacrylamide hydrazide having an average molecular weight of 10,000 or less.

16. The method according to claim 12, comprising:
forming a first compound by coupling the antibody to at least one of the plural reactive functional groups; and
coupling at least one remaining reactive functional group of the first compound to the detectable label molecule.

17. The method according to claim 12, comprising:
forming a first compound by coupling the detectable label molecule to at least one of the plural reactive functional groups; and
coupling at least one remaining reactive functional group of the first compound to the antibody.

18. The method according to claim 17 comprising coupling the polymeric carrier to the Fc portion of the antibody through reactive hydrazide functional groups.

19. The method according to claim 17 further comprising activating the antibody for reaction with the at least one remaining reactive functional group.

20. The method according to claim 19 comprising chemically modifying a glycosylated portion of the antibody.

21. The method according to claim 12 where the detectable label molecule is an enzyme, a fluorophore, a luminophore, a hapten, a fluorescent nanoparticle, or combinations thereof.

22. The method according to claim 12 where the detectable label molecule is a hapten selected from di-nitrophenyl, biotin, digoxigenin, fluorescein, rhodamine, bromodeoxyuridine, mouse immunoglobulin, or combinations thereof.

23. The method according to claim 12 where the detectable label molecule is a hapten selected from an oxazole, a pyrazole, a thiazole, a benzofurazan, a triterpene, a urea, a thiourea, a nitroaryl other than dinitrophenyl, a rotenoid, a coumarin, a cyclolignan, a heterobiaryl, an azoaryl, a benzodiazepine, or combinations thereof.

24. The method according to claim 12 where the detectable label molecule is a hapten coupled to the antibody through the reactive functional groups using an NHS-PEG linker.

25. The method according to claim 12 where plural different haptens are coupled to the polymeric carrier.

26. The method according to claim 12, comprising:
oxidizing an Fc portion of the antibody to form the oxidized Fc portion;
coupling the polymeric carrier to the oxidized Fc portion of the antibody through at least one reactive hydrazide functional group to form a first compound; and
coupling the first compound to at least one hapten through a reactive hydrazide functional group to form a second compound.

27. The method according to claim 26 where the hapten is coupled to the antibody through reactive hydrazide functional groups using an NHS-PEG linker.

28. The method according to claim 26 comprising coupling the first compound to plural haptens.

29. The method according to claim 13 where the polysaccharide is selected from carbohydrates, cellulose, carboxymethylcellulose, dextran, amido dextrans, hydrazide dextrans, hydrazine dextrans, glycogen, polyhyaluronic acid, starch, or combinations thereof.

30. The method according to claim 13 where the polyamino acid is selected from poly(aspargine), poly(aspartic acid), poly(glutamic acid), poly(glutamine), poly(lysine), poly(guanidines), or combinations thereof.

31. The method according to claim 12 where the molecular conjugate is a polyhaptenylated conjugate.

32. The conjugate of claim 1 wherein the molecule is selected from a biological molecule, a detectable label molecule, or combinations thereof.

33. The conjugate of claim 32 wherein the molecule is selected from a peptide, a protein, an enzyme, a sugar, a polysaccharide, a lipid, a glycoprotein, a lipoprotein, a hapten, or combinations thereof.

34. The method of claim 12 wherein the molecule is selected from a biological molecule, a detectable label molecule, or combinations thereof.

35. The method of claim 34 wherein the biological molecule is selected from a peptide, a protein, an enzyme, a sugar, a polysaccharide, a lipid, a glycoprotein, a lipoprotein, a hapten, or combinations thereof.

36. A conjugate, comprising:

a polymeric carrier, other than a polyacrylamide hydrazide thiol, the polymeric carrier comprising plural reactive functional groups selected from hydrazines, hydrazides, hydrazine derivatives, hydrazide derivatives, guanidines, aminoguanidines, hydroxyl amines, or combinations thereof;

an antibody covalently bonded to a hapten molecule through at least one reactive functional group provided by the polymeric carrier, wherein the polymeric carrier is directly coupled to an oxidized Fc portion of the antibody; and a molecule, other than the antibody or the hapten molecule, selected from a peptide, a protein, an enzyme, a sugar, a polysaccharide, a lipid, a glycoprotein, a lipoprotein, or a hapten bonded to the polymeric carrier through at least one reactive functional group.

37. A method for forming a molecular conjugate, comprising reacting a polymeric carrier comprising plural reactive functional groups selected from hydrazines, hydrazides, hydrazine derivatives, hydrazide derivatives, guanidines, aminoguanidines, hydroxyl amines, or combinations thereof, with an antibody, a hapten molecule, and a molecule, other than the antibody or the hapten molecule, selected from a peptide, a protein, an enzyme, a sugar, a polysaccharide, a lipid, a glycoprotein, a lipoprotein, or a hapten, wherein the polymeric carrier is other than a polyacrylamide hydrazide thiol and is directly coupled to an oxidized Fc portion of the antibody through at least one reactive functional group.

\* \* \* \* \*